United States Patent
Giannoukos et al.

(10) Patent No.: US 12,110,545 B2
(45) Date of Patent: Oct. 8, 2024

(54) METHODS OF ASSESSING NUCLEASE CLEAVAGE

(71) Applicant: Editas Medicine, Inc., Cambridge, MA (US)

(72) Inventors: Georgia Giannoukos, Cambridge, MA (US); Christopher Wilson, Cambridge, MA (US); Dawn Ciulla, Cambridge, MA (US)

(73) Assignee: Editas Medicine, Inc., Cambridge, MA (US)

( * ) Notice: Subject to any disclaimer, the term of this patent is extended or adjusted under 35 U.S.C. 154(b) by 1058 days.

(21) Appl. No.: 16/475,862

(22) PCT Filed: Jan. 5, 2018

(86) PCT No.: PCT/US2018/012652
§ 371 (c)(1),
(2) Date: Jul. 3, 2019

(87) PCT Pub. No.: WO2018/129368
PCT Pub. Date: Jul. 12, 2018

(65) Prior Publication Data
US 2020/0232022 A1    Jul. 23, 2020

Related U.S. Application Data

(60) Provisional application No. 62/443,212, filed on Jan. 6, 2017, provisional application No. 62/502,434, filed on May 5, 2017, provisional application No. 62/570,300, filed on Oct. 10, 2017.

(51) Int. Cl.
*C12Q 1/6869*    (2018.01)
*G16B 20/50*    (2019.01)
*G16B 30/10*    (2019.01)

(52) U.S. Cl.
CPC ........... *C12Q 1/6869* (2013.01); *G16B 20/50* (2019.02); *G16B 30/10* (2019.02)

(58) Field of Classification Search
CPC ....... C12Q 1/6869; G16B 20/50; G16B 30/10
See application file for complete search history.

(56) References Cited

U.S. PATENT DOCUMENTS

| 5,409,818 A | 4/1995 | Davey et al. |
| 5,523,204 A | 6/1996 | Singer et al. |
| 5,536,649 A | 7/1996 | Fraiser et al. |
| 5,591,609 A | 1/1997 | Auerbach |

(Continued)

FOREIGN PATENT DOCUMENTS

| EP | 1167524 A1 | 1/2002 |
| EP | 1312682 A1 | 5/2003 |

(Continued)

OTHER PUBLICATIONS

US 10,077,445 B2, 09/2018, Dounda et al. (withdrawn)

(Continued)

*Primary Examiner* — Jana A Hines
(74) *Attorney, Agent, or Firm* — Choate, Hall & Stewart LLP; Rolando Medina; Meaghan E. Bychowski

(57) ABSTRACT

The present disclosure relates to methods of analyzing activity of nucleases, such as ZFNs, TALENs or CRISPR-associated nucleases, in particular their cutting at "off-target" loci.

11 Claims, 24 Drawing Sheets

Specification includes a Sequence Listing.

(56) References Cited

U.S. PATENT DOCUMENTS

| | | |
|---|---|---|
| 5,614,389 A | 3/1997 | Auerbach |
| 5,624,825 A | 4/1997 | Walker et al. |
| 5,631,147 A | 5/1997 | Lohman et al. |
| 5,648,211 A | 7/1997 | Fraiser et al. |
| 5,733,752 A | 3/1998 | Lohman et al. |
| 5,744,311 A | 4/1998 | Fraiser et al. |
| 5,756,702 A | 5/1998 | Lohman et al. |
| 5,773,733 A | 6/1998 | Tuan et al. |
| 5,786,183 A | 7/1998 | Ryder et al. |
| 5,834,202 A | 11/1998 | Auerbach |
| 5,849,547 A | 12/1998 | Cleuziat et al. |
| 5,874,260 A | 2/1999 | Cleuziat et al. |
| 5,916,779 A | 6/1999 | Pearson et al. |
| 6,063,604 A | 5/2000 | Wick et al. |
| 6,087,133 A | 7/2000 | Dattagupta et al. |
| 6,124,120 A | 9/2000 | Lizardi |
| 6,214,587 B1 | 4/2001 | Dattagupta et al. |
| 6,218,151 B1 | 4/2001 | Cleuziat et al. |
| 6,238,868 B1 | 5/2001 | Carrino et al. |
| 6,251,639 B1 | 6/2001 | Kurn |
| 6,280,949 B1 | 8/2001 | Lizardi |
| 6,309,833 B1 | 10/2001 | Edman et al. |
| 6,326,173 B1 | 12/2001 | Edman et al. |
| 6,410,278 B1 | 6/2002 | Notomi et al. |
| 6,448,017 B1 | 9/2002 | Auerbach |
| 6,593,113 B1 * | 7/2003 | Tenkanen ............. C12Q 1/6869 435/6.16 |
| 7,413,857 B2 | 8/2008 | Dahl et al. |
| 8,546,553 B2 | 10/2013 | Terns et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,023,649 B2 | 5/2015 | Mali et al. |
| 9,074,199 B1 | 7/2015 | Chavez et al. |
| 9,080,211 B2 | 7/2015 | Grunenwald et al. |
| 9,163,284 B2 | 10/2015 | Liu et al. |
| 9,234,213 B2 | 1/2016 | Wu |
| 9,260,723 B2 | 2/2016 | Mali et al. |
| 9,260,752 B1 | 2/2016 | May et al. |
| 9,267,135 B2 | 2/2016 | Church et al. |
| 9,322,037 B2 | 4/2016 | Liu et al. |
| 9,388,430 B2 | 7/2016 | Liu et al. |
| 9,404,098 B2 | 8/2016 | Terns et al. |
| 9,410,198 B2 | 8/2016 | May et al. |
| 9,422,553 B2 | 8/2016 | Terns et al. |
| 9,512,446 B1 | 12/2016 | Joung et al. |
| 9,567,603 B2 | 2/2017 | Joung et al. |
| 9,567,604 B2 | 2/2017 | Joung et al. |
| 9,587,252 B2 | 3/2017 | Church et al. |
| 9,637,739 B2 | 5/2017 | Siksnys et al. |
| 9,663,782 B2 | 5/2017 | Yu et al. |
| 9,688,971 B2 | 6/2017 | Doudna et al. |
| 9,725,714 B2 | 8/2017 | May et al. |
| 9,738,908 B2 | 8/2017 | Wu |
| 9,752,132 B2 | 9/2017 | Joung et al. |
| 9,790,490 B2 | 10/2017 | Zhang et al. |
| 9,803,194 B2 | 10/2017 | May et al. |
| 9,809,814 B1 | 11/2017 | May et al. |
| 9,809,839 B2 | 11/2017 | Kim et al. |
| 9,822,370 B2 | 11/2017 | Musunuru et al. |
| 9,822,372 B2 | 11/2017 | Zhang et al. |
| 9,822,407 B2 | 11/2017 | Joung et al. |
| 9,840,713 B2 | 12/2017 | Zhang |
| 9,850,484 B2 | 12/2017 | Joung et al. |
| 9,873,894 B2 | 1/2018 | Conway et al. |
| 9,879,269 B2 | 1/2018 | Barrangou et al. |
| 9,885,026 B2 | 2/2018 | Brouns et al. |
| 9,902,974 B2 | 2/2018 | Conway et al. |
| 9,909,122 B2 | 3/2018 | May et al. |
| 9,926,545 B2 | 3/2018 | Joung et al. |
| 9,926,546 B2 | 3/2018 | Joung et al. |
| 9,944,912 B2 | 4/2018 | Joung et al. |
| 9,963,689 B2 | 5/2018 | Doudna et al. |
| 9,970,001 B2 | 5/2018 | Miller |
| 9,970,024 B2 | 5/2018 | Church et al. |
| 9,970,030 B2 | 5/2018 | Cameron et al. |
| 9,988,674 B2 | 6/2018 | Joung et al. |
| 10,066,233 B2 | 9/2018 | Barrangou et al. |
| 10,077,453 B2 | 9/2018 | Liu et al. |
| 10,093,910 B2 | 10/2018 | Joung et al. |
| 10,100,291 B2 | 10/2018 | Chavez et al. |
| 10,113,167 B2 | 10/2018 | Doudna et al. |
| 10,113,179 B2 | 10/2018 | Begemann et al. |
| 10,113,207 B2 | 10/2018 | Wang |
| 10,119,133 B2 | 11/2018 | Joung et al. |
| 10,125,361 B2 | 11/2018 | May et al. |
| 10,202,589 B2 | 2/2019 | Joung et al. |
| 10,202,619 B2 | 2/2019 | Wu |
| 10,227,611 B2 | 3/2019 | Doudna et al. |
| 10,266,850 B2 | 4/2019 | Doudna et al. |
| 10,301,651 B2 | 5/2019 | Doudna et al. |
| 10,308,961 B2 | 6/2019 | Doudna et al. |
| 10,329,587 B2 | 6/2019 | Church et al. |
| 10,351,878 B2 | 7/2019 | Doudna et al. |
| 10,358,658 B2 | 7/2019 | Doudna et al. |
| 10,358,659 B2 | 7/2019 | Doudna et al. |
| 10,377,998 B2 | 8/2019 | Zhang et al. |
| 10,378,027 B2 | 8/2019 | Joung et al. |
| 10,385,360 B2 | 8/2019 | Doudna et al. |
| 10,392,607 B2 | 8/2019 | Sternberg et al. |
| 10,400,253 B2 | 9/2019 | Doudna et al. |
| 10,407,697 B2 | 9/2019 | Doudna et al. |
| 10,415,059 B2 | 9/2019 | Joung et al. |
| 10,415,061 B2 | 9/2019 | Doudna et al. |
| 10,421,980 B2 | 9/2019 | Doudna et al. |
| 10,428,319 B2 | 10/2019 | Steinberg et al. |
| 10,428,352 B2 | 10/2019 | Doudna et al. |
| 10,435,679 B2 | 10/2019 | Chavez et al. |
| 10,435,708 B2 | 10/2019 | Mali et al. |
| 10,443,076 B2 | 10/2019 | Doudna et al. |
| 2005/0153333 A1 | 7/2005 | Sooknanan |
| 2010/0076057 A1 | 3/2010 | Sontheimer et al. |
| 2010/0093617 A1 | 4/2010 | Barrangou et al. |
| 2010/0120098 A1 | 5/2010 | Grunenwald et al. |
| 2013/0011828 A1 | 1/2013 | Barrangou et al. |
| 2014/0068797 A1 | 3/2014 | Doudna et al. |
| 2014/0093941 A1 | 4/2014 | Terns et al. |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0199767 A1 | 7/2014 | Barrangou et al. |
| 2014/0242664 A1 | 8/2014 | Zhang et al. |
| 2014/0242699 A1 | 8/2014 | Zhang |
| 2014/0256046 A1 | 9/2014 | Zhang et al. |
| 2014/0273037 A1 | 9/2014 | Wu |
| 2014/0273226 A1 | 9/2014 | Wu |
| 2014/0273230 A1 | 9/2014 | Chen et al. |
| 2014/0273233 A1 | 9/2014 | Chen et al. |
| 2014/0287938 A1 | 9/2014 | Zhang et al. |
| 2014/0294773 A1 | 10/2014 | Brouns et al. |
| 2014/0302563 A1 | 10/2014 | Doudna et al. |
| 2014/0310830 A1 | 10/2014 | Zhang et al. |
| 2014/0315985 A1 | 10/2014 | May et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0356956 A1 | 12/2014 | Church et al. |
| 2014/0357523 A1 | 12/2014 | Zeiner et al. |
| 2014/0357530 A1 | 12/2014 | Zhang et al. |
| 2014/0377868 A1 | 12/2014 | Joung et al. |
| 2015/0020223 A1 | 1/2015 | Zhang et al. |
| 2015/0024499 A1 | 1/2015 | Brouns et al. |

(56) References Cited

U.S. PATENT DOCUMENTS

| | | |
|---|---|---|
| 2015/0024500 A1 | 1/2015 | Yu et al. |
| 2015/0031132 A1 | 1/2015 | Church et al. |
| 2015/0031133 A1 | 1/2015 | Church et al. |
| 2015/0031134 A1 | 1/2015 | Zhang et al. |
| 2015/0044191 A1 | 2/2015 | Liu et al. |
| 2015/0044192 A1 | 2/2015 | Liu et al. |
| 2015/0044772 A1 | 2/2015 | Zhao |
| 2015/0045546 A1 | 2/2015 | Siksnys et al. |
| 2015/0050699 A1 | 2/2015 | Siksnys et al. |
| 2015/0056705 A1 | 2/2015 | Conway et al. |
| 2015/0071889 A1 | 3/2015 | Musunuru et al. |
| 2015/0071898 A1 | 3/2015 | Liu et al. |
| 2015/0071899 A1 | 3/2015 | Liu et al. |
| 2015/0079681 A1 | 3/2015 | Zhang |
| 2015/0132821 A1 | 5/2015 | Fine et al. |
| 2015/0176013 A1 | 6/2015 | Musunuru et al. |
| 2015/0184139 A1 | 7/2015 | Zhang et al. |
| 2015/0203872 A1 | 7/2015 | Zhang |
| 2015/0232833 A1 | 8/2015 | Mali et al. |
| 2015/0232882 A1 | 8/2015 | Zhang et al. |
| 2015/0240261 A1 | 8/2015 | Siksnys et al. |
| 2015/0247150 A1 | 9/2015 | Zhang et al. |
| 2015/0259684 A1 | 9/2015 | Church et al. |
| 2015/0259704 A1 | 9/2015 | Church et al. |
| 2015/0284727 A1 | 10/2015 | Kim et al. |
| 2015/0291961 A1 | 10/2015 | Siksnys et al. |
| 2015/0291965 A1 | 10/2015 | Zhang et al. |
| 2015/0291966 A1 | 10/2015 | Zhang et al. |
| 2015/0322457 A1 | 11/2015 | Kim et al. |
| 2015/0344912 A1 | 12/2015 | Kim et al. |
| 2015/0353905 A1 | 12/2015 | Weiss et al. |
| 2015/0353917 A1 | 12/2015 | Miller |
| 2015/0356239 A1 | 12/2015 | Zhang et al. |
| 2015/0368638 A1 | 12/2015 | Steemers et al. |
| 2016/0002670 A1 | 1/2016 | Church et al. |
| 2016/0010076 A1 | 1/2016 | Joung et al. |
| 2016/0010154 A1 | 1/2016 | Laganiere et al. |
| 2016/0017366 A1 | 1/2016 | Chen et al. |
| 2016/0017396 A1* | 1/2016 | Cann ............. C12P 19/34 506/26 |
| 2016/0024523 A1 | 1/2016 | Joung et al. |
| 2016/0024524 A1 | 1/2016 | Joung et al. |
| 2016/0032274 A1 | 2/2016 | Church et al. |
| 2016/0046949 A1 | 2/2016 | May et al. |
| 2016/0046961 A1 | 2/2016 | Jinek et al. |
| 2016/0046962 A1 | 2/2016 | May et al. |
| 2016/0046963 A1 | 2/2016 | May et al. |
| 2016/0046978 A1 | 2/2016 | May et al. |
| 2016/0060653 A1 | 3/2016 | Doudna et al. |
| 2016/0060654 A1 | 3/2016 | Doudna et al. |
| 2016/0068864 A1 | 3/2016 | Doudna et al. |
| 2016/0068887 A1 | 3/2016 | May et al. |
| 2016/0076020 A1 | 3/2016 | May et al. |
| 2016/0090607 A1 | 3/2016 | Conway et al. |
| 2016/0090622 A1 | 3/2016 | Liu et al. |
| 2016/0102324 A1 | 4/2016 | Duchateau et al. |
| 2016/0108470 A1 | 4/2016 | May et al. |
| 2016/0115488 A1 | 4/2016 | Zhang et al. |
| 2016/0115489 A1 | 4/2016 | Zhang et al. |
| 2016/0122774 A1 | 5/2016 | Duchateau et al. |
| 2016/0130608 A1 | 5/2016 | Doudna et al. |
| 2016/0130609 A1 | 5/2016 | Doudna et al. |
| 2016/0138008 A1 | 5/2016 | Doudna et al. |
| 2016/0138046 A1 | 5/2016 | Wu |
| 2016/0145646 A1 | 5/2016 | Frendewey et al. |
| 2016/0153003 A1 | 6/2016 | Joung et al. |
| 2016/0153004 A1 | 6/2016 | Zhang et al. |
| 2016/0153006 A1 | 6/2016 | Zhang et al. |
| 2016/0160210 A1 | 6/2016 | Mali et al. |
| 2016/0168592 A1 | 6/2016 | Church et al. |
| 2016/0175462 A1 | 6/2016 | Zhang et al. |
| 2016/0184362 A1 | 6/2016 | Duchateau et al. |
| 2016/0186152 A1 | 6/2016 | Brouns et al. |
| 2016/0186213 A1 | 6/2016 | Zhang et al. |
| 2016/0186214 A1 | 6/2016 | Brouns et al. |
| 2016/0201089 A1 | 7/2016 | Gersbach et al. |
| 2016/0208243 A1 | 7/2016 | Zhang et al. |
| 2016/0215276 A1 | 7/2016 | Liu et al. |
| 2016/0222416 A1 | 8/2016 | Church et al. |
| 2016/0237455 A1 | 8/2016 | Glucksmann et al. |
| 2016/0237456 A1 | 8/2016 | Church et al. |
| 2016/0251640 A1 | 9/2016 | May et al. |
| 2016/0257973 A1 | 9/2016 | Cameron et al. |
| 2016/0272965 A1 | 9/2016 | Zhang et al. |
| 2016/0281072 A1 | 9/2016 | Zhang |
| 2016/0298097 A1 | 10/2016 | Chavez et al. |
| 2016/0298125 A1 | 10/2016 | Chen et al. |
| 2016/0298132 A1 | 10/2016 | Chen et al. |
| 2016/0298133 A1 | 10/2016 | Chen et al. |
| 2016/0298134 A1 | 10/2016 | Chen et al. |
| 2016/0298135 A1 | 10/2016 | Chen et al. |
| 2016/0298136 A1 | 10/2016 | Chen et al. |
| 2016/0298137 A1 | 10/2016 | Chen et al. |
| 2016/0298138 A1 | 10/2016 | Chen et al. |
| 2016/0304907 A1 | 10/2016 | Mali et al. |
| 2016/0304950 A1 | 10/2016 | Joung et al. |
| 2016/0312198 A1 | 10/2016 | Joung et al. |
| 2016/0312199 A1 | 10/2016 | Joung et al. |
| 2016/0312280 A1 | 10/2016 | May et al. |
| 2016/0319260 A1 | 11/2016 | Joung et al. |
| 2016/0319261 A1 | 11/2016 | Joung et al. |
| 2016/0319281 A1 | 11/2016 | Tsai et al. |
| 2016/0319349 A1 | 11/2016 | May et al. |
| 2016/0333389 A1 | 11/2016 | Liu et al. |
| 2016/0340662 A1 | 11/2016 | Zhang et al. |
| 2016/0355796 A1 | 12/2016 | Davidson et al. |
| 2016/0355797 A1 | 12/2016 | Konermann et al. |
| 2016/0355816 A1 | 12/2016 | Terns et al. |
| 2017/0037416 A1 | 2/2017 | Barrangou et al. |
| 2017/0044569 A9 | 2/2017 | Church et al. |
| 2017/0051276 A1 | 2/2017 | May et al. |
| 2017/0051310 A1 | 2/2017 | Doudna et al. |
| 2017/0051312 A1 | 2/2017 | Jinek et al. |
| 2017/0053062 A1 | 2/2017 | Cradick et al. |
| 2017/0058271 A1 | 3/2017 | Joung et al. |
| 2017/0073705 A1 | 3/2017 | Chen et al. |
| 2017/0073747 A1 | 3/2017 | Joung et al. |
| 2017/0076039 A1 | 3/2017 | Kim et al. |
| 2017/0081650 A1 | 3/2017 | Joung et al. |
| 2017/0088833 A1 | 3/2017 | Joung et al. |
| 2017/0107536 A1 | 4/2017 | Zhang et al. |
| 2017/0152508 A1 | 6/2017 | Joung et al. |
| 2017/0152528 A1 | 6/2017 | Zhang |
| 2017/0166893 A1 | 6/2017 | Doudna et al. |
| 2017/0166903 A1 | 6/2017 | Zhang et al. |
| 2017/0175142 A1 | 6/2017 | Zhang et al. |
| 2017/0175144 A1 | 6/2017 | Zhang et al. |
| 2017/0191078 A1 | 7/2017 | Zhang et al. |
| 2017/0191082 A1 | 7/2017 | Chen et al. |
| 2017/0198269 A1 | 7/2017 | Zhang et al. |
| 2017/0211142 A1 | 7/2017 | Smargon et al. |
| 2017/0233703 A1 | 8/2017 | Xie et al. |
| 2017/0247671 A1 | 8/2017 | Yung et al. |
| 2017/0268022 A1 | 9/2017 | Liu et al. |
| 2017/0298330 A1 | 10/2017 | Sato et al. |
| 2017/0306307 A1 | 10/2017 | Zhang et al. |
| 2017/0306335 A1 | 10/2017 | Zhang et al. |
| 2017/0327805 A1 | 11/2017 | Joung et al. |
| 2017/0327806 A1 | 11/2017 | Joung et al. |
| 2017/0327820 A1 | 11/2017 | May et al. |
| 2017/0349915 A1 | 12/2017 | May et al. |
| 2018/0002682 A1 | 1/2018 | Sternberg et al. |
| 2018/0016572 A1 | 1/2018 | Tang |
| 2018/0030425 A1 | 2/2018 | Joung et al. |
| 2018/0066242 A1 | 3/2018 | Zhang et al. |
| 2018/0073002 A1 | 3/2018 | Deiters et al. |
| 2018/0080051 A1 | 3/2018 | Sheikh et al. |
| 2018/0087104 A1 | 3/2018 | Joung et al. |
| 2018/0100148 A1 | 4/2018 | Vakulskas et al. |
| 2018/0119121 A1 | 5/2018 | Brouns et al. |
| 2018/0119175 A1 | 5/2018 | Conway et al. |
| 2018/0127780 A1 | 5/2018 | Liu et al. |
| 2018/0135073 A1 | 5/2018 | Chen et al. |
| 2018/0148735 A1 | 5/2018 | Begemann et al. |

(56) References Cited

U.S. PATENT DOCUMENTS

| | | |
|---|---|---|
| 2018/0155708 A1 | 6/2018 | Church et al. |
| 2018/0155716 A1 | 6/2018 | Zhang et al. |
| 2018/0163188 A1 | 6/2018 | Xie et al. |
| 2018/0163213 A1 | 6/2018 | Aneja et al. |
| 2018/0163265 A1 | 6/2018 | Zhang et al. |
| 2018/0187176 A1 | 7/2018 | Behlke et al. |
| 2018/0187195 A1 | 7/2018 | Siksnys et al. |
| 2018/0208931 A1 | 7/2018 | Doudna et al. |
| 2018/0216088 A1 | 8/2018 | Joung et al. |
| 2018/0230495 A1 | 8/2018 | Doudna et al. |
| 2018/0230496 A1 | 8/2018 | Doudna et al. |
| 2018/0230497 A1 | 8/2018 | Doudna et al. |
| 2018/0237801 A1 | 8/2018 | Doudna et al. |
| 2018/0245100 A1 | 8/2018 | Doudna et al. |
| 2018/0245101 A1 | 8/2018 | Doudna et al. |
| 2018/0251791 A1 | 9/2018 | Doudna et al. |
| 2018/0251793 A1 | 9/2018 | Doudna et al. |
| 2018/0251794 A1 | 9/2018 | Doudna et al. |
| 2018/0251795 A1 | 9/2018 | Charpentier et al. |
| 2018/0265864 A1 | 9/2018 | Li et al. |
| 2018/0273981 A1 | 9/2018 | Doudna et al. |
| 2018/0282713 A1 | 10/2018 | Van Der Oost |
| 2018/0282714 A1 | 10/2018 | Joung et al. |
| 2018/0282764 A1 | 10/2018 | Jinek et al. |
| 2018/0291383 A1 | 10/2018 | Musunuru et al. |
| 2018/0298360 A1 | 10/2018 | Sternberg et al. |
| 2018/0298406 A1 | 10/2018 | Doudna et al. |
| 2018/0298407 A1 | 10/2018 | Doudna et al. |
| 2018/0312824 A1 | 11/2018 | Zhang et al. |
| 2018/0312874 A1 | 11/2018 | Doudna et al. |
| 2018/0312875 A1 | 11/2018 | Doudna et al. |
| 2018/0312876 A1 | 11/2018 | Doudna et al. |
| 2018/0320163 A1 | 11/2018 | Koonin et al. |
| 2018/0320197 A1 | 11/2018 | Gersbach et al. |
| 2018/0320201 A1 | 11/2018 | Vakulskas et al. |
| 2018/0327761 A1 | 11/2018 | Duchateau et al. |
| 2018/0346927 A1 | 12/2018 | Doudna et al. |
| 2018/0355332 A1 | 12/2018 | Steinberg et al. |
| 2019/0002889 A1 | 1/2019 | Cheng et al. |
| 2019/0002921 A1 | 1/2019 | Doudna et al. |
| 2019/0002922 A1 | 1/2019 | Doudna et al. |
| 2019/0002923 A1 | 1/2019 | Doudna et al. |
| 2019/0010471 A1 | 1/2019 | Zhang et al. |
| 2019/0010481 A1 | 1/2019 | Joung et al. |
| 2019/0010520 A1 | 1/2019 | Doudna et al. |
| 2019/0048340 A1 | 2/2019 | Charpentier et al. |
| 2019/0062790 A1 | 2/2019 | Doudna et al. |
| 2019/0071688 A1 | 3/2019 | Begemann et al. |
| 2019/0083656 A1 | 3/2019 | Khalili et al. |
| 2019/0085329 A1 | 3/2019 | Siksnys et al. |
| 2019/0093129 A1 | 3/2019 | Doudna et al. |
| 2019/0106687 A1 | 4/2019 | Joung et al. |
| 2019/0106711 A1 | 4/2019 | Doudna et al. |
| 2019/0106712 A1 | 4/2019 | Doudna et al. |
| 2019/0106713 A1 | 4/2019 | Doudna et al. |
| 2019/0106714 A1 | 4/2019 | Doudna et al. |
| 2019/0106715 A1 | 4/2019 | Doudna et al. |
| 2019/0218602 A1 | 7/2019 | Zhang et al. |
| 2019/0264186 A1 | 8/2019 | Yamano et al. |
| 2019/0284583 A1 | 9/2019 | Doudna et al. |

FOREIGN PATENT DOCUMENTS

| | | |
|---|---|---|
| JP | 2001/510055 A | 7/2001 |
| WO | WO-95/23875 A1 | 9/1995 |
| WO | WO-99/04035 A1 | 1/1999 |
| WO | WO-00/28082 A1 | 5/2000 |
| WO | WO-00/56877 A1 | 9/2000 |
| WO | WO-02/16639 A1 | 2/2002 |
| WO | WO-2007/025097 A2 | 3/2007 |
| WO | WO-2010/011961 A2 | 1/2010 |
| WO | WO-2013/098244 A1 | 7/2013 |
| WO | WO-2013/141680 A1 | 9/2013 |
| WO | WO-2013/142578 A1 | 9/2013 |
| WO | WO-2013/169398 A2 | 11/2013 |
| WO | WO-2013/176772 A1 | 11/2013 |
| WO | WO-2014/018423 A2 | 1/2014 |
| WO | WO-2014/065596 A1 | 5/2014 |
| WO | WO-2014/089290 A1 | 6/2014 |
| WO | WO-2014/093479 A1 | 6/2014 |
| WO | WO-2014/093595 A1 | 6/2014 |
| WO | WO-2014/093622 A2 | 6/2014 |
| WO | WO-2014/093635 A1 | 6/2014 |
| WO | WO-2014/093655 A2 | 6/2014 |
| WO | WO-2014/093661 A2 | 6/2014 |
| WO | WO-2014/093694 A1 | 6/2014 |
| WO | WO-2014/093701 A1 | 6/2014 |
| WO | WO-2014/093709 A1 | 6/2014 |
| WO | WO-2014/093712 A1 | 6/2014 |
| WO | WO-2014/093718 A1 | 6/2014 |
| WO | WO-2014/099744 A1 | 6/2014 |
| WO | WO-2014/099750 A2 | 6/2014 |
| WO | WO-2014/113493 A1 | 7/2014 |
| WO | WO-2014/144288 A1 | 9/2014 |
| WO | WO-2014/144592 A2 | 9/2014 |
| WO | WO-2014/144761 A2 | 9/2014 |
| WO | WO-2014/145599 A2 | 9/2014 |
| WO | WO-2014/150624 A1 | 9/2014 |
| WO | WO-2014/152432 A2 | 9/2014 |
| WO | WO-2014/165825 A2 | 10/2014 |
| WO | WO-2014/186585 A2 | 11/2014 |
| WO | WO-2014/191518 A1 | 12/2014 |
| WO | WO-2014/191521 A2 | 12/2014 |
| WO | WO-2014/197568 A2 | 12/2014 |
| WO | WO-2014/197748 A2 | 12/2014 |
| WO | WO-2014/204578 A1 | 12/2014 |
| WO | WO-2014/204724 A1 | 12/2014 |
| WO | WO-2014/204725 A1 | 12/2014 |
| WO | WO-2014/204727 A1 | 12/2014 |
| WO | WO-2014/204728 A1 | 12/2014 |
| WO | WO-2014/204729 A1 | 12/2014 |
| WO | WO-2015/006290 A1 | 1/2015 |
| WO | WO-2015/006294 A2 | 1/2015 |
| WO | WO-2015/010114 A1 | 1/2015 |
| WO | WO-2015/013583 A2 | 1/2015 |
| WO | WO-2015/021353 A1 | 2/2015 |
| WO | WO-2015/021426 A1 | 2/2015 |
| WO | WO-2015/035162 A2 | 3/2015 |
| WO | WO-2015/048577 A2 | 4/2015 |
| WO | WO-2015/077318 A1 | 5/2015 |
| WO | WO-2015/089351 A1 | 6/2015 |
| WO | WO-2015/089354 A1 | 6/2015 |
| WO | WO-2015/089427 A1 | 6/2015 |
| WO | WO-2015/089486 A2 | 6/2015 |
| WO | WO-2015/113063 A1 | 7/2015 |
| WO | WO-2015/163733 A1 | 10/2015 |
| WO | WO-2015/188056 A1 | 12/2015 |
| WO | WO-2015/188065 A1 | 12/2015 |
| WO | WO-2015/200378 A1 | 12/2015 |
| WO | WO-2016/022363 A2 | 2/2016 |
| WO | WO-2016/028682 A1 | 2/2016 |
| WO | WO-2016/033246 A1 | 3/2016 |
| WO | WO-2016/057821 A2 | 4/2016 |
| WO | WO-2016/073990 A2 | 5/2016 |
| WO | WO-2016/076672 A1 | 5/2016 |
| WO | WO-2016/081798 A1 | 5/2016 |
| WO | WO-2016/081923 A2 | 5/2016 |
| WO | WO-2016/100974 A1 | 6/2016 |
| WO | WO-2016/106236 A1 | 6/2016 |
| WO | WO-2016/106244 A1 | 6/2016 |
| WO | WO-2016/112242 A1 | 7/2016 |
| WO | WO-2016/114972 A1 | 7/2016 |
| WO | WO-2016/141224 A1 | 9/2016 |
| WO | WO-2016/161207 A1 | 10/2016 |
| WO | WO-2016/164797 A1 | 10/2016 |
| WO | WO-2016/166340 A1 | 10/2016 |
| WO | WO-2016/167300 A1 | 10/2016 |
| WO | WO-2016/196655 A1 | 12/2016 |
| WO | WO-2016/205613 A1 | 12/2016 |
| WO | WO-2016/205711 A1 | 12/2016 |
| WO | WO-2016/205749 A1 | 12/2016 |
| WO | WO-2016/205759 A1 | 12/2016 |
| WO | WO-2017/015015 A1 | 1/2017 |
| WO | WO-2017/035416 A2 | 3/2017 |

(56) References Cited

FOREIGN PATENT DOCUMENTS

| | | |
|---|---|---|
| WO | WO-2017/040348 A1 | 3/2017 |
| WO | WO-2017/044843 A1 | 3/2017 |
| WO | WO-2017/048969 A1 | 3/2017 |
| WO | WO-2017/049129 A2 | 3/2017 |
| WO | WO-2017/059313 A1 | 4/2017 |
| WO | WO-2017/064546 A1 | 4/2017 |
| WO | WO-2017/066588 A2 | 4/2017 |
| WO | WO-2017/070633 A2 | 4/2017 |
| WO | WO-2017/083766 A1 | 5/2017 |
| WO | WO-2017/099494 A1 | 6/2017 |
| WO | WO-2017/127807 A1 | 7/2017 |
| WO | WO-2017/136335 A1 | 8/2017 |
| WO | WO-2017/151444 A1 | 9/2017 |
| WO | WO-2017/161068 A1 | 9/2017 |
| WO | WO-2017/181107 A2 | 10/2017 |
| WO | WO-2017/184768 A1 | 10/2017 |
| WO | WO-2017/188797 A1 | 11/2017 |
| WO | WO-2017/189308 A1 | 11/2017 |
| WO | WO-2017/197238 A1 | 11/2017 |
| WO | WO-2017/217768 A1 | 12/2017 |
| WO | WO-2017/219027 A1 | 12/2017 |
| WO | WO-2017/219033 A1 | 12/2017 |
| WO | WO-2017/222773 A1 | 12/2017 |
| WO | WO-2018/013558 A1 | 1/2018 |
| WO | WO-2018/022634 A1 | 2/2018 |
| WO | WO-2018/035387 A1 | 2/2018 |
| WO | WO-2018/035388 A1 | 2/2018 |
| WO | WO-2018/049073 A1 | 3/2018 |
| WO | WO-2018/049077 A1 | 3/2018 |
| WO | WO-2018/049079 A1 | 3/2018 |
| WO | WO-2018/052247 A1 | 3/2018 |
| WO | WO-2018/053053 A1 | 3/2018 |
| WO | WO-2018/053070 A1 | 3/2018 |
| WO | WO-2018/064352 A1 | 4/2018 |
| WO | WO-2018/064371 A1 | 4/2018 |
| WO | WO-2018/067447 A1 | 4/2018 |
| WO | WO-2018/068053 A2 | 4/2018 |
| WO | WO-2018/069474 A1 | 4/2018 |
| WO | WO-2018/071868 A1 | 4/2018 |
| WO | WO-2018/071892 A1 | 4/2018 |
| WO | WO-2018/074979 A1 | 4/2018 |
| WO | WO-2018/089664 A1 | 5/2018 |
| WO | WO-2018/097657 A1 | 5/2018 |
| WO | WO-2018/098383 A1 | 5/2018 |
| WO | WO-2018/108272 A1 | 6/2018 |
| WO | WO-2018/108338 A1 | 6/2018 |
| WO | WO-2018/108339 A1 | 6/2018 |
| WO | WO-2018/109101 A1 | 6/2018 |
| WO | WO-2018/112451 A1 | 6/2018 |
| WO | WO-2018/129368 A2 | 7/2018 |
| WO | WO-2018/149888 A1 | 8/2018 |
| WO | WO-2018/170015 A1 | 9/2018 |
| WO | WO-2018/172556 A1 | 9/2018 |
| WO | WO-2018/188571 A1 | 10/2018 |
| WO | WO-2018/191715 A2 | 10/2018 |
| WO | WO-2018/195540 A1 | 10/2018 |
| WO | WO-2018/195545 A2 | 10/2018 |
| WO | WO-2018/197495 A1 | 11/2018 |
| WO | WO-2018/209712 A1 | 11/2018 |
| WO | WO-2018/213351 A1 | 11/2018 |
| WO | WO-2018/221685 A1 | 12/2018 |
| WO | WO-2018/226855 A1 | 12/2018 |
| WO | WO-2018/227114 A1 | 12/2018 |
| WO | WO-2019/003193 A1 | 1/2019 |
| WO | WO-2019/006471 A2 | 1/2019 |
| WO | WO-2019/009682 A2 | 1/2019 |
| WO | WO-2019/018041 A1 | 1/2019 |
| WO | WO-2019/036513 A1 | 2/2019 |
| WO | WO-2019/040650 A1 | 2/2019 |
| WO | WO-2019/046540 A1 | 3/2019 |
| WO | WO-2019/049913 A1 | 3/2019 |
| WO | WO-2019/051419 A1 | 3/2019 |
| WO | WO-2019/060469 A2 | 3/2019 |
| WO | WO-2019/067322 A1 | 4/2019 |
| WO | WO-2019/072596 A1 | 4/2019 |
| WO | WO-2019/074542 A1 | 4/2019 |
| WO | WO-2019/089796 A1 | 5/2019 |
| WO | WO-2019/089804 A1 | 5/2019 |
| WO | WO-2019/089808 A1 | 5/2019 |
| WO | WO-2019/089820 A1 | 5/2019 |
| WO | WO-2019/090173 A1 | 5/2019 |
| WO | WO-2019/090174 A1 | 5/2019 |
| WO | WO-2019/090175 A1 | 5/2019 |
| WO | WO-2019/092042 A1 | 5/2019 |
| WO | WO-2019/099943 A1 | 5/2019 |
| WO | WO-2019/126709 A1 | 6/2019 |
| WO | WO-2019/126716 A1 | 6/2019 |
| WO | WO-2019/126762 A2 | 6/2019 |
| WO | WO-2019/126774 A1 | 6/2019 |
| WO | WO-2019/168953 A1 | 9/2019 |
| WO | WO-2019/178427 A1 | 9/2019 |
| WO | WO-2019/178428 A1 | 9/2019 |
| WO | WO-2019/183150 A1 | 9/2019 |

OTHER PUBLICATIONS

Adey, A. et al., Rapid, low-input, low-bias construction of shotgun fragment libraries by high-density in vitro transposition, Genome Biology, 11(12), R119 (2010).

Anders, C. et al., Structural basis of PAM-dependent target DNA recognition by the Cas9 endonuclease, Nature, 513(7519):569-73 (2014).

Atkins, M. et al. Minutes of Recombinant DNA Advisory Committee, 146th Meeting Jun. 21-22, 2016 in Bethseda, Maryland, RAC Review (2016).

Briner, A. E. et al. Guide RNA functional modules direct Cas9 activity and orthogonality Molecular Cell, 56(2), 333-339 (2014).

Brinkman, E. K. et al. Easy quantitative assessment of genome editing by sequence trace decomposition, Nucleic Acids Res., 42(22):e168 (2014).

Caruccio, N. et al, Nextera™ Technology for NGS DNA Library Preparation: Simultaneous Fragmentation and Tagging by In Vitro Transportation, Nextera™ Technology, 16: 4-6 (2009).

Chen, L. et al. DNA damage is a pervasive cause of sequencing errors, directly confounding variant identification, Science, 355:752-6 (2017). [With Supplemental Materials].

Chiarle, R. et al. Genome-wide translocation sequencing reveals mechanisms of chromosome breaks and rearrangements in B cells, Cell, 147: 107-119 (2011).

Cong, L. et al., Multiplex genome engineering using CRISPR/Cas systems, Science, 339(6121):819-23 (2013).

Costello, M. et al. Discovery and characterization of artifactual mutations in deep coverage targeted capture sequencing data due to oxidative DNA damage during sample preparation, Nucleic Acids Res., 41: 1-12 (2013).

Craig, N.L., Transposon Tn7, Curr. Top. Microbial. Immunol., 204: 27-48 (1996).

Craig, N.L., Unity in transposition reactions, Science, 270: 253-254 (1995).

Delmont et al, Metagenomic mining for microbiologists, ISME J., 5(12): 1837-43 (2011).

Devine, S.E. and Boeke, J. D., Efficient integration of artificial transposons into plasmid targets in vitro: a useful tool for DNA mapping, sequencing and genetic analysis, Nucleic Acids Research, 22(18): 3765-3772 (1994).

Esvelt, K. M. and Wang, H.H., Genome-scale engineering for systems and synthetic biology, Molecular Systems Biology, 9:641 (2013).

Frock et al., Genome-wide detection of DNA double-stranded breaks induced by engineered nucleases, Nat. Biotechnol., 33: 179-186 (2015).

Ghezraoui, H. et al. Chromosomal translocations in human cells are generated by canonical nonhomologous end-joining, Mol. Cell., 55:829-42 (2014). [With Supplemental Materials].

Giannoukos, G. et al, UDiTas™, a genome editing detection method for indels and genome rearrangements, BMC Genomics, 19(212): 10 pages (2018).

(56) References Cited

OTHER PUBLICATIONS

Giannoukos, G. et al, UDiTaS™, a streamlined genome editing detection method for on and off-target edits, large deletions, and translocations, NASDAQ OMX's New Release Distribution Channel, poster, retrieved from http://www.editasmedicine.com/data/documents/myers_asgct_2017_poster_final_1494608479_1497467603.pdf, Apr. 23, 2018.

Hendel, A. et al. Quantifying on- and off-target genome editing, Trends Biotechol., 33:132-140 (2015).

Hsu, P.D. et al., DNA targeting specificity of RNA-guided Cas9 nucleases, Nat Biotechnol, 31(9): 827-832 (2013).

Hu, J. et al. Detecting DNA double-stranded breaks in mammalian genomes by linear amplification-mediated high-throughput genome-wide translocation sequencing, Nat. Protocol., 11 :853-871 (2016).

Ichikawa and Ohtsubo, In vitro transposition of transposon Tn3, J. Biol. Chem., 265(31): 18829-32 (1990).

International Search Report for PCT/US2018/012652 (Methods of Assessing Nuclease Cleavage, filed Jan. 5, 2018), issued by ISA/EPO, 10 pages (Jul. 2, 2018).

Jiang, W. et al. RNA-guided editing of bacterial genomes using CRISPR-Cas systems, Nat Biotechnol., 31(3): 233-239 (2013).

Jiang, W. et al., Induction of site-specific chromosomal translocations in embryonic stem cells by CRISPR/Cas9, Sci. Rep., 6:21918 (2016).

Jinek, M. et al., A programmable dual-RNA-guided DNA endonuclease in adaptive, bacterial immunity, Science, 337(6096): 816-821 (2012).

Jinek, M. et al., Structures of Cas9 endonucleases reveal RNA-mediated conformational activation, Science, 343(6176), 1247997 (2014).

Kaufman, P.D. and Rio, D.C., P element transposition in vitro proceeds by a cut-and-paste mechanism and uses GTP as a cofactor, Cell, 69(1): 27-39 (1992).

Kleckner, N. et al. Tn10 and IS10 transposition and chromosome rearrangements: mechanism and regulation in vivo and in vitro, Curr. Top. Microbial. Immunol., 204: 49-82 (1996).

Lampe et al., A purified mariner transposase is sufficient to mediate transposition in vitro, EMBO J., 15(19): 5470-5479 (1996).

Langmead, B. and Salzberg, S.L., Fast gapped-read alignment with Bowtie 2, Nat. Methods, 9:357-9 (2012).

Li, H. et al., The Sequence Alignment/Map format and SAMtools, Bioinformatics, 25:2078-9 (2009).

Mali, P. et al., RNA-guided human genome engineering via Cas9, Science, 339(6121): 823-826 (2013).

Martin, M., Cutadapt Removes Adapter Sequences From High-Throughput Sequencing Reads, EMBnet.Journal, 17: 10-12 (2011).

Mashal, R.D. et al. Detection of mutations by cleavage of DNA heteroduplexes with bacteriophage resolvases, Nat. Genet., 9:177-183 (1995).

Nishimasu, H. et al., Crystal structure of Cas9 in complex with guide RNA and target DNA. Cell, 156: 935-949 (2014).

Nishimasu, H. et al., Crystal Structure of *Staphylococcus aureus* Cas9, Cell, 162:1113-1126 (2015).

Ohtsubo and Sekine, Bacterial insertion sequences, Curr. Top. Microbial. Immunol., 204: 1-26 (1996).

Park et al., In Vitro Transposition of Tn5, J. Korean Soc. Microbiol. 27:381-389 (1992).

Ran, F. A. et al., Double nicking by RNA-guided CRISPR Cas9 for enhanced genome editing specificity, Cell 154(6), 1380-1389 (2013).

Robinson, J. T. et al., Integrative genomics viewer, Nat. Biotechnol., 29:24-26 (2011).

Shmakov, S. et al., Discovery and Functional Characterization of Diverse Class 2 CRISPR-Cas Systems, Molecular Cell, 60: 385-397 (2015).

Thorvaldsdottir, H. et al. Integrative Genomics Viewer (IGV): high-performance genomics data visualization and exploration, Brief Bioinform., 14: 178-192 (2013).

Tsai, S.Q. et al. Guide-seq enables genome-wide profiling of off-target cleavage by CRISPR-Cas nucleases, Nat. Biotechnol., 33:187-197 (2014).

Tykco, J. et al. Methods for Optimizing CRISPR-Cas9 Genome Editing Specificity, Mol. Cell., 63:355-370 (2016).

Vos, J.C. et al., Transposase is the only nematode protein required for in vitro transposition of Tc1, Genes Dev., 10(6): 755-61 (1996).

Vouillot, L. et al. Comparison of T7E1 and surveyor mismatch cleavage assays to detect mutations triggered by engineered nucleases, G3 (Bethesda), 5:407-415 (2015).

Wang et al., A novel genetic system based on zinc finger nucleases for the identification of interactions between proteins in vivo, PLoS One, 8(12):e85650 (2013).

Written Opinion for PCT/US2018012652 (Methods of Assessing Nuclease Cleavage, filed Jan. 5, 2018), issued by ISA/EPO, 13 pages (Jul. 2, 2018).

Yamano, T. et al. Crystal Structure of Cpf1 in Complex with Guide RNA and Target DNA, Cell, 165(4): 949-962 (2016).

Yee, J.-K., Off-target effects of engineered nucleases, The FEBS Journal, 283: 3239-3248 (2016).

Zetsche et al., Cpf1 is a single RNA-guided endonuclease of a class 2 CRISPR-Cas system, Cell 163, 759-771 (2015).

Zheng et al., Anchored multiplex PCR for targeted next-generation sequencing, Nat Med., 20(12): 1479-84 (2014).

\* cited by examiner

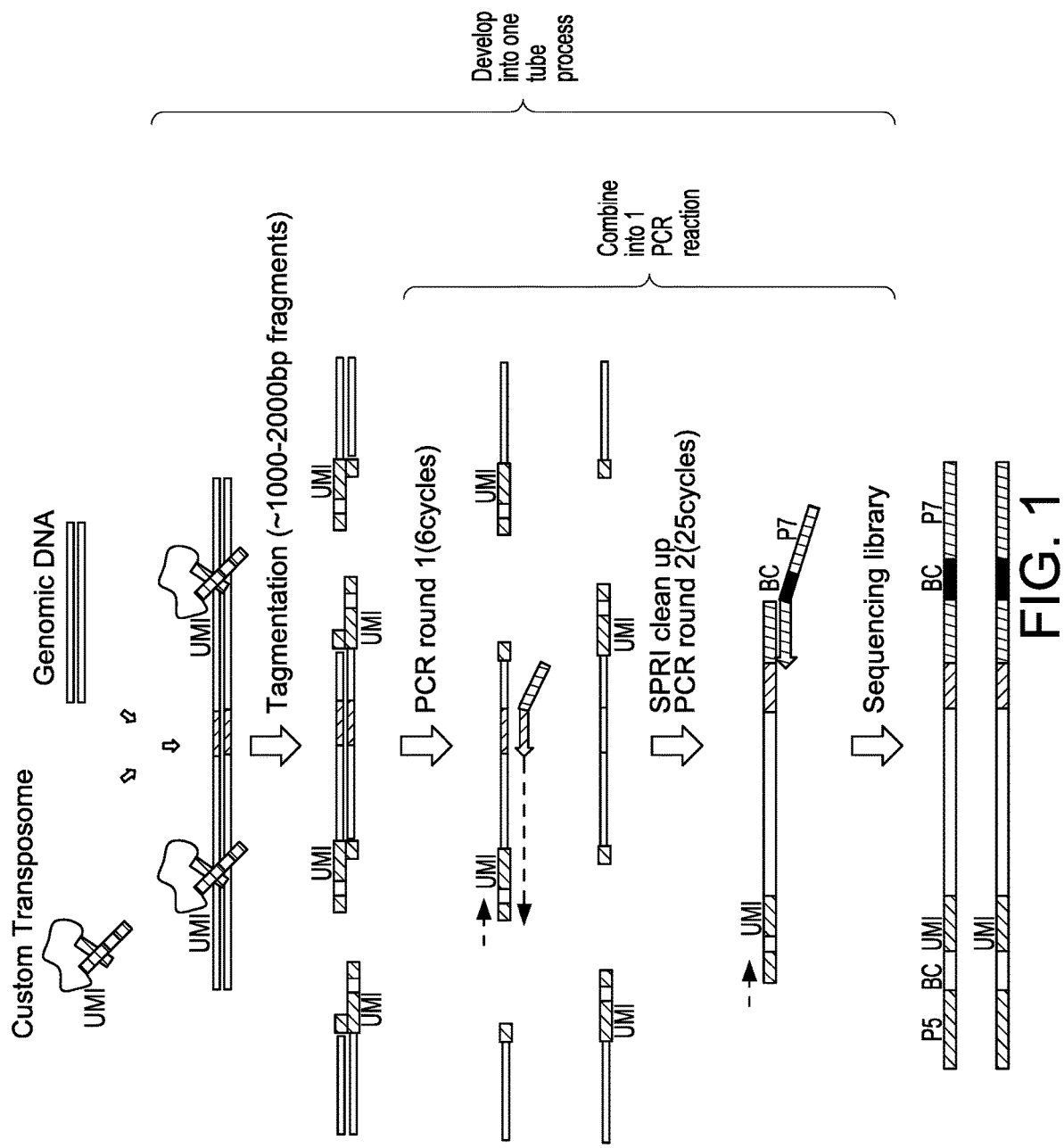

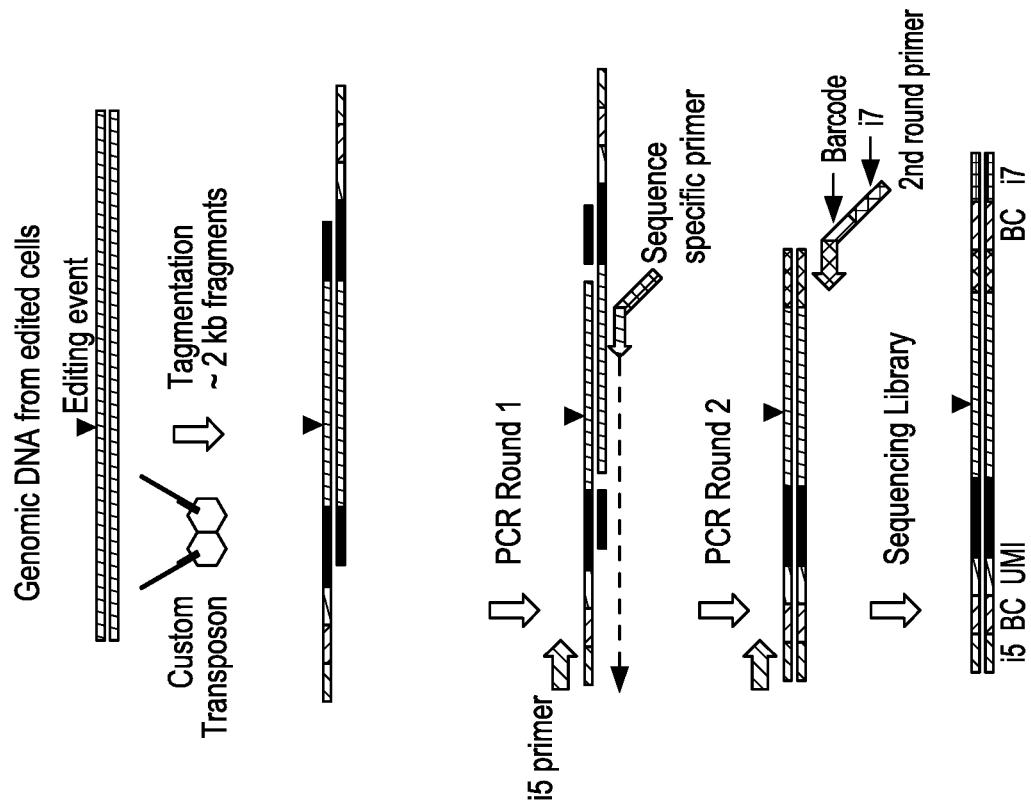
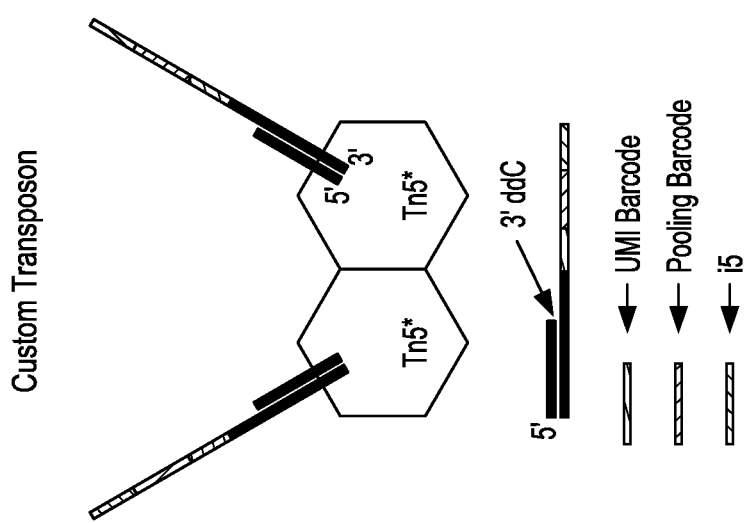
FIG. 2A
FIG. 2B

FIG. 4 CONTD.

FIG. 4 CONTD.

78%-93% alignment of MiSeq reads to correct target

| SAMPLE ID | | genomicDNA name | guideRNA name | total_R1R2_reads | total_target_reads | %_on_target | target |
|---|---|---|---|---|---|---|---|
| NGS_req-097_ | A_1_amp_01_5249836 | JHED046_1 | .9 | 101512 | 83565 | 82 | |
| NGS_req-097_ | A_2_amp_02_5249836 | JHED046_2 | .34 | 91628 | 79697 | 87 | |
| NGS_req-097_ | A_3_amp_03_5249836 | JHED046_3 | .35 | 118184 | 94552 | 80 | |
| NGS_req-097_ | A_4_amp_04_5249836 | JHED046_4 | .36 | 82818 | 69476 | 84 | |
| NGS_req-097_ | A_5_amp_05_5249836 | JHED046_5 | .37 | 76414 | 63341 | 83 | G1 |
| NGS_req-097_ | A_6_amp_06_5249836 | JHED046_6 | .38 | 104338 | 81211 | 78 | |
| NGS_req-097_ | A_7_amp_07_5249836 | JHED046_8 | .41 | 119076 | 99933 | 84 | |
| NGS_req-097_ | A_8_amp_08_5249836 | JHED046_9 | .43 | 118350 | 90221 | 76 | |
| NGS_req-097_ | A_9_amp_09_5249836 | JHED046_10 | neg cntrl | 196818 | 173567 | 88 | |
| NGS_req-097_ | A_1_amp_10_5254760 | JHED046_1 | .9 | 173060 | 147982 | 86 | |
| NGS_req-097_ | A_2_amp_11_5254760 | JHED046_2 | .34 | 136770 | 125339 | 92 | |
| NGS_req-097_ | A_3_amp_12_5254760 | JHED046_3 | .35 | 220634 | 203468 | 92 | |
| NGS_req-097_ | A_4_amp_13_5254760 | JHED046_4 | .36 | 171376 | 157285 | 92 | |
| NGS_req-097_ | A_5_amp_14_5254760 | JHED046_5 | .37 | 141088 | 128307 | 91 | G2 |
| NGS_req-097_ | A_6_amp_15_5254760 | JHED046_6 | .38 | 133158 | 118597 | 89 | |
| NGS_req-097_ | A_7_amp_16_5254760 | JHED046_8 | .41 | 187056 | 173777 | 93 | |
| NGS_req-097_ | A_8_amp_17_5254760 | JHED046_9 | .43 | 152182 | 130977 | 86 | |
| NGS_req-097_ | A_9_amp_18_5254760 | JHED046_10 | neg cntrl | 211478 | 196876 | 93 | |

FIG. 5

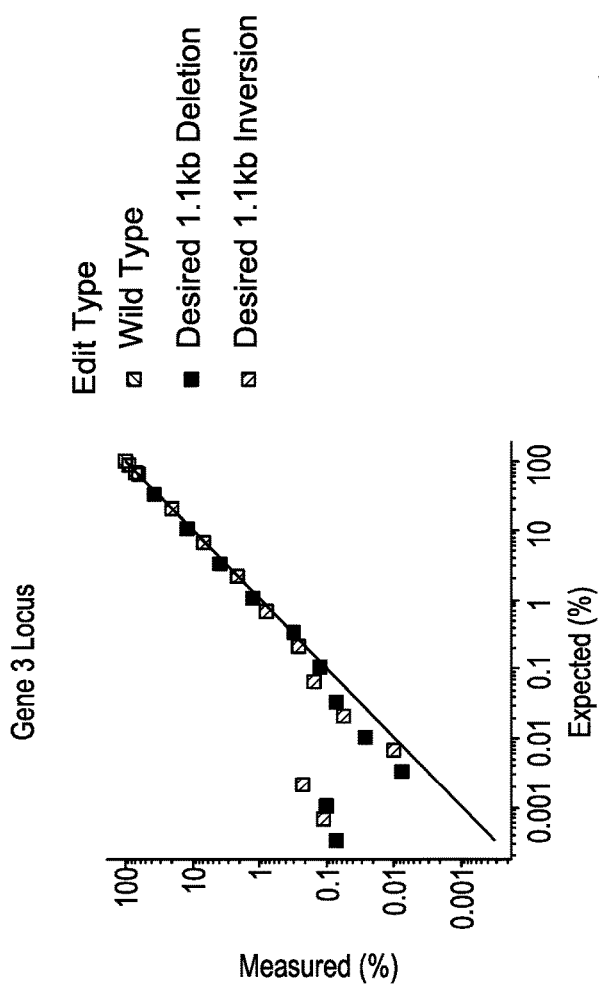
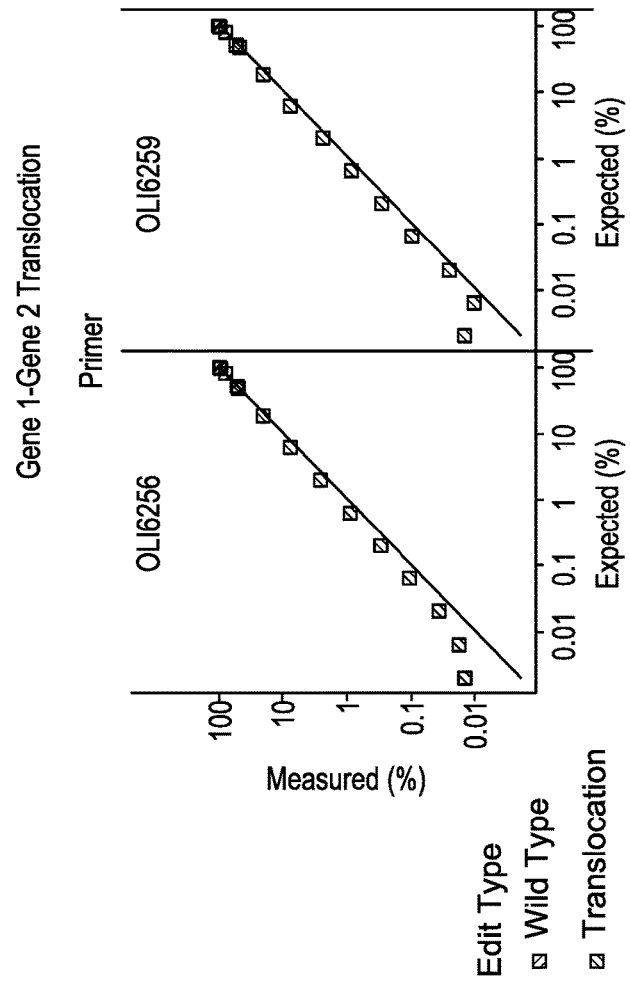
FIG. 19A
FIG. 19B

SEQUENCE LISTING

```
<160> NUMBER OF SEQ ID NOS: 94

<210> SEQ ID NO 1
<211> LENGTH: 65
<212> TYPE: DNA
<213> ORGANISM: Artificial Sequence
<220> FEATURE:
<223> OTHER INFORMATION: Synthetic primer

<400> SEQUENCE: 1
caccgctagc taatacgact cactataggc cacggagcga gacatctgtt ttagagctag    60
aaata                                                                65

<210> SEQ ID NO 2
<211> LENGTH: 65
<212> TYPE: DNA
<213> ORGANISM: Artificial Sequence
<220> FEATURE:
<223> OTHER INFORMATION: Synthetic primer

<400> SEQUENCE: 2
caccgctagc taatacgact cactatagct ggtacacggc agggtcagtt ttagagctag    60
aaata                                                                65

<210> SEQ ID NO 3
<211> LENGTH: 53
<212> TYPE: DNA
<213> ORGANISM: Artificial Sequence
<220> FEATURE:
<223> OTHER INFORMATION: Synthetic primer

<400> SEQUENCE: 3
tttttttttt tttttttttt gcaccgactc ggtgccactt ttcaagttg ata            53

<210> SEQ ID NO 4
<211> LENGTH: 64
<212> TYPE: DNA
<213> ORGANISM: Artificial Sequence
<220> FEATURE:
```

<223> OTHER INFORMATION: Synthetic primer

<400> SEQUENCE: 4
gtgactggag ttcagacgtg tgctcttccg atctggacca tggatgcact ctgtaaattc    60
tcat    64

<210> SEQ ID NO 5
<211> LENGTH: 65
<212> TYPE: DNA
<213> ORGANISM: Artificial Sequence
<220> FEATURE:
<223> OTHER INFORMATION: Synthetic primer

<400> SEQUENCE: 5
gtgactggag ttcagacgtg tgctcttccg atctgcatgc cttcttaaac atcacgagac    60
tctaa    65

<210> SEQ ID NO 6
<211> LENGTH: 64
<212> TYPE: DNA
<213> ORGANISM: Artificial Sequence
<220> FEATURE:
<223> OTHER INFORMATION: Synthetic primer

<400> SEQUENCE: 6
gtgactggag ttcagacgtg tgctcttccg atctgcactg ttgctcttga agtccataga    60
cctc    64

<210> SEQ ID NO 7
<211> LENGTH: 80
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (38)..(47)
<223> OTHER INFORMATION: a, c, t, g, unknown or other
<220> FEATURE:
<221> NAME/KEY: misc_feature
<222> LOCATION: (38)..(47)
<223> OTHER INFORMATION: n is a, c, g, or t

<400> SEQUENCE: 7
aatgatacgg cgaccaccga gatctacact agatcgcnnn nnnnnnntcg tcggcagcgt    60
cagatgtgta taagagacag    80

<210> SEQ ID NO 8
<211> LENGTH: 80
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (38)..(47)
<223> OTHER INFORMATION: a, c, t, g, unknown or other
<220> FEATURE:
<221> NAME/KEY: misc_feature
<222> LOCATION: (38)..(47)
<223> OTHER INFORMATION: n is a, c, g, or t

<400> SEQUENCE: 8
aatgatacgg cgaccaccga gatctacacc tctctatnnn nnnnnntcg tcggcagcgt    60 cagatgtgta taagagacag    80

-continued

```
<210> SEQ ID NO 9
<211> LENGTH: 80
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (38)..(47)
<223> OTHER INFORMATION: a, c, t, g, unknown or other
<220> FEATURE:
<221> NAME/KEY: misc_feature
<222> LOCATION: (38)..(47)
<223> OTHER INFORMATION: n is a, c, g, or t

<400> SEQUENCE: 9
aatgatacgg cgaccaccga gatctacact atcctctnnn nnnnnnntcg tcggcagcgt    60
cagatgtgta taagagacag                                                80

<210> SEQ ID NO 10
<211> LENGTH: 80
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (38)..(47)
<223> OTHER INFORMATION: a, c, t, g, unknown or other
<220> FEATURE:
<221> NAME/KEY: misc_feature
<222> LOCATION: (38)..(47)
<223> OTHER INFORMATION: n is a, c, g, or t

<400> SEQUENCE: 10
aatgatacgg cgaccaccga gatctacaca gagtagannn nnnnnnntcg tcggcagcgt    60
cagatgtgta taagagacag                                                80

<210> SEQ ID NO 11
<211> LENGTH: 80
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (38)..(47)
<223> OTHER INFORMATION: a, c, t, g, unknown or other
<220> FEATURE:
<221> NAME/KEY: misc_feature
<222> LOCATION: (38)..(47)
<223> OTHER INFORMATION: n is a, c, g, or t

<400> SEQUENCE: 11
aatgatacgg cgaccaccga gatctacacg taaggagnnn nnnnnnntcg tcggcagcgt    60
cagatgtgta taagagacag                                                80

<210> SEQ ID NO 12
<211> LENGTH: 80
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (38)..(47)
<223> OTHER INFORMATION: a, c, t, g, unknown or other
<220> FEATURE:
```

```
<221> NAME/KEY: misc_feature
<222> LOCATION: (38)..(47)
<223> OTHER INFORMATION: n is a, c, g, or t

<400> SEQUENCE: 12
aatgatacgg cgaccaccga gatctacaca ctgcatannn nnnnnnntcg tcggcagcgt    60
cagatgtgta taagagacag                                                80

<210> SEQ ID NO 13
<211> LENGTH: 80
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (38)..(47)
<223> OTHER INFORMATION: a, c, t, g, unknown or other
<220> FEATURE:
<221> NAME/KEY: misc_feature
<222> LOCATION: (38)..(47)
<223> OTHER INFORMATION: n is a, c, g, or t

<400> SEQUENCE: 13
aatgatacgg cgaccaccga gatctacaca aggagtannn nnnnnnntcg tcggcagcgt    60
cagatgtgta taagagacag                                                80

<210> SEQ ID NO 14
<211> LENGTH: 80
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (38)..(47)
<223> OTHER INFORMATION: a, c, t, g, unknown or other
<220> FEATURE:
<221> NAME/KEY: misc_feature
<222> LOCATION: (38)..(47)
<223> OTHER INFORMATION: n is a, c, g, or t

<400> SEQUENCE: 14
aatgatacgg cgaccaccga gatctacacc taagcctnnn nnnnnnntcg tcggcagcgt    60
cagatgtgta taagagacag                                                80

<210> SEQ ID NO 15
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 15
ctgtctctta tacac                                                     15

<210> SEQ ID NO 16
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 16
aatgatacgg cgaccaccga gatctacac                                      29
```

```
<210> SEQ ID NO 17
<211> LENGTH: 53
<212> TYPE: DNA
<213> ORGANISM: Artificial Sequence
<220> FEATURE:
<223> OTHER INFORMATION: Synthetic primer

<400> SEQUENCE: 17
caagcagaag acggcatacg agatagcgga atgtgactgg agttcagacg tgt              53

<210> SEQ ID NO 18
<211> LENGTH: 53
<212> TYPE: DNA
<213> ORGANISM: Artificial Sequence
<220> FEATURE:
<223> OTHER INFORMATION: Synthetic primer

<400> SEQUENCE: 18
caagcagaag acggcatacg agatgatcat gcgtgactgg agttcagacg tgt              53

<210> SEQ ID NO 19
<211> LENGTH: 53
<212> TYPE: DNA
<213> ORGANISM: Artificial Sequence
<220> FEATURE:
<223> OTHER INFORMATION: Synthetic primer

<400> SEQUENCE: 19
caagcagaag acggcatacg agataagacg gagtgactgg agttcagacg tgt              53

<210> SEQ ID NO 20
<211> LENGTH: 53
<212> TYPE: DNA
<213> ORGANISM: Artificial Sequence
<220> FEATURE:
<223> OTHER INFORMATION: Synthetic primer

<400> SEQUENCE: 20
caagcagaag acggcatacg agatcgagtc ctgtgactgg agttcagacg tgt              53

<210> SEQ ID NO 21
<211> LENGTH: 53
<212> TYPE: DNA
<213> ORGANISM: Artificial Sequence
<220> FEATURE:
<223> OTHER INFORMATION: Synthetic primer

<400> SEQUENCE: 21
caagcagaag acggcatacg agattcctca gggtgactgg agttcagacg tgt              53

<210> SEQ ID NO 22
<211> LENGTH: 53
<212> TYPE: DNA
<213> ORGANISM: Artificial Sequence
<220> FEATURE:
<223> OTHER INFORMATION: Synthetic primer

<400> SEQUENCE: 22
caagcagaag acggcatacg agatgtacgg atgtgactgg agttcagacg tgt              53

<210> SEQ ID NO 23
<211> LENGTH: 53
<212> TYPE: DNA
<213> ORGANISM: Artificial Sequence
<220> FEATURE:
<223> OTHER INFORMATION: Synthetic primer
```

<400> SEQUENCE: 23
caagcagaag acggcatacg agatcatctc tcgtgactgg agttcagacg tgt             53

<210> SEQ ID NO 24
<211> LENGTH: 53
<212> TYPE: DNA
<213> ORGANISM: Artificial Sequence
<220> FEATURE:
<223> OTHER INFORMATION: Synthetic primer

<400> SEQUENCE: 24
caagcagaag acggcatacg agatgtcgga gcgtgactgg agttcagacg tgt             53

<210> SEQ ID NO 25
<211> LENGTH: 53
<212> TYPE: DNA
<213> ORGANISM: Artificial Sequence
<220> FEATURE:
<223> OTHER INFORMATION: Synthetic primer

<400> SEQUENCE: 25
caagcagaag acggcatacg agatacggag aagtgactgg agttcagacg tgt             53

<210> SEQ ID NO 26
<211> LENGTH: 53
<212> TYPE: DNA
<213> ORGANISM: Artificial Sequence
<220> FEATURE:
<223> OTHER INFORMATION: Synthetic primer

<400> SEQUENCE: 26
caagcagaag acggcatacg agataggaga tggtgactgg agttcagacg tgt             53

<210> SEQ ID NO 27
<211> LENGTH: 53
<212> TYPE: DNA
<213> ORGANISM: Artificial Sequence
<220> FEATURE:
<223> OTHER INFORMATION: Synthetic primer

<400> SEQUENCE: 27
caagcagaag acggcatacg agatagtact cggtgactgg agttcagacg tgt             53

<210> SEQ ID NO 28
<211> LENGTH: 53
<212> TYPE: DNA
<213> ORGANISM: Artificial Sequence
<220> FEATURE:
<223> OTHER INFORMATION: Synthetic primer

<400> SEQUENCE: 28
caagcagaag acggcatacg agatggactc tagtgactgg agttcagacg tgt             53

<210> SEQ ID NO 29
<211> LENGTH: 78
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: misc_feature
<222> LOCATION: (38)..(39)
<223> OTHER INFORMATION: n is a, c, g, or t

```
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: misc_feature
<222> LOCATION: (44)..(45)
<223> OTHER INFORMATION: n is a, c, g, or t

<400> SEQUENCE: 29
aatgatacgg cgaccaccga gatctacaca ctgcatannw nnwnnacact ctttccctac      60
acgacgctct tccgatct                                                   78

<210> SEQ ID NO 30
<211> LENGTH: 78
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: misc_feature
<222> LOCATION: (44)..(45)
<223> OTHER INFORMATION: n is a, c, g, or t

<400> SEQUENCE: 30
aatgatacgg cgaccaccga gatctacaca aggagtannw nnwnnacact ctttccctac      60
acgacgctct tccgatct                                                   78

<210> SEQ ID NO 31
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 31
gatcggaaga gcca                                                       14

<210> SEQ ID NO 32
<211> LENGTH: 15
<212> TYPE: DNA
<213> ORGANISM: Artificial Sequence
<220> FEATURE:
```

<223> OTHER INFORMATION: Synthetic oligonucleotide

<400> SEQUENCE: 32
ctgtctctta tacac                                                         15

<210> SEQ ID NO 33
<211> LENGTH: 80
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (38)..(47)
<223> OTHER INFORMATION: a, c, t, g, unknown or other
<220> FEATURE:
<221> NAME/KEY: misc_feature
<222> LOCATION: (38)..(47)
<223> OTHER INFORMATION: n is a, c, g, or t

<400> SEQUENCE: 33
aatgatacgg cgaccaccga gatctacact agatcgcnnn nnnnnnntcg tcggcagcgt         60
cagatgtgta taagagacag                                                    80

<210> SEQ ID NO 34
<211> LENGTH: 80
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (38)..(47)
<223> OTHER INFORMATION: a, c, t, g, unknown or other
<220> FEATURE:
<221> NAME/KEY: misc_feature
<222> LOCATION: (38)..(47)
<223> OTHER INFORMATION: n is a, c, g, or t

<400> SEQUENCE: 34
aatgatacgg cgaccaccga gatctacacc tctctatnnn nnnnnnntcg tcggcagcgt         60
cagatgtgta taagagacag                                                    80

<210> SEQ ID NO 35
<211> LENGTH: 80
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (38)..(47)
<223> OTHER INFORMATION: a, c, t, g, unknown or other
<220> FEATURE:
<221> NAME/KEY: misc_feature
<222> LOCATION: (38)..(47)
<223> OTHER INFORMATION: n is a, c, g, or t

<400> SEQUENCE: 35
aatgatacgg cgaccaccga gatctacact atcctctnnn nnnnnnntcg tcggcagcgt         60
cagatgtgta taagagacag                                                    80

<210> SEQ ID NO 36
<211> LENGTH: 80
<212> TYPE: DNA
<213> ORGANISM: Artificial Sequence
<220> FEATURE:
<223> OTHER INFORMATION: Synthetic oligonucleotide

```
<220> FEATURE:
<221> NAME/KEY: modified_base
<222> LOCATION: (38)..(47)
<223> OTHER INFORMATION: a, c, t, g, unknown or other
<220> FEATURE:
<221> NAME/KEY: misc_feature
<222> LOCATION: (38)..(47)
<223> OTHER INFORMATION: n is a, c, g, or t

<400> SEQUENCE: 36
aatgatacgg cgaccaccga gatctacaca gagtagannn nnnnnnntcg tcggcagcgt    60
cagatgtgta taagagacag                                               80

<210> SEQ ID NO 37
<211> LENGTH: 80
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (38)..(47)
<223> OTHER INFORMATION: a, c, t, g, unknown or other
<220> FEATURE:
<221> NAME/KEY: misc_feature
<222> LOCATION: (38)..(47)
<223> OTHER INFORMATION: n is a, c, g, or t

<400> SEQUENCE: 37
aatgatacgg cgaccaccga gatctacacg taaggagnnn nnnnnntcg tcggcagcgt    60 cagatgtgta taagagacag                                               80

<210> SEQ ID NO 38
<211> LENGTH: 80
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (38)..(47)
<223> OTHER INFORMATION: a, c, t, g, unknown or other
<220> FEATURE:
<221> NAME/KEY: misc_feature
<222> LOCATION: (38)..(47)
<223> OTHER INFORMATION: n is a, c, g, or t

<400> SEQUENCE: 38
aatgatacgg cgaccaccga gatctacaca ctgcatannn nnnnnntcg tcggcagcgt    60 cagatgtgta taagagacag                                               80

<210> SEQ ID NO 39
<211> LENGTH: 80
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (38)..(47)
<223> OTHER INFORMATION: a, c, t, g, unknown or other
<220> FEATURE:
<221> NAME/KEY: misc_feature
<222> LOCATION: (38)..(47)
<223> OTHER INFORMATION: n is a, c, g, or t

<400> SEQUENCE: 39
aatgatacgg cgaccaccga gatctacaca aggagtannn nnnnnntcg tcggcagcgt    60
```
cagatgtgta taagagacag                                                     80

<210> SEQ ID NO 40
<211> LENGTH: 80
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (38)..(47)
<223> OTHER INFORMATION: a, c, t, g, unknown or other
<220> FEATURE:
<221> NAME/KEY: misc_feature
<222> LOCATION: (38)..(47)
<223> OTHER INFORMATION: n is a, c, g, or t

<400> SEQUENCE: 40
aatgatacgg cgaccaccga gatctacacc taagcctnnn nnnnnnntcg tcggcagcgt    60
cagatgtgta taagagacag                                                 80

<210> SEQ ID NO 41
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 41
tagatcgctt tttttttt                                                    18

<210> SEQ ID NO 42
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 42
ctctctattt tttttttt                                                    18

<210> SEQ ID NO 43
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 43
tatcctcttt tttttttt                                                    18

<210> SEQ ID NO 44
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 44
agagtagatt tttttttt                                                    18

<210> SEQ ID NO 45
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 45
gtaaggagtt tttttttt                                            18

<210> SEQ ID NO 46
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 46
actgcatatt tttttttt                                            18

<210> SEQ ID NO 47
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 47
aaggagtatt tttttttt                                            18

<210> SEQ ID NO 48
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 48
ctaagccttt tttttttt                                            18

<210> SEQ ID NO 49
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 49
aatgatacgg cgaccaccga gatctacac                                29

<210> SEQ ID NO 50
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 50
caagcagaag acggcatacg agatagcgga atgtgactgg agttcagacg tgt      53

<210> SEQ ID NO 51
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 51
caagcagaag acggcatacg agatgatcat gcgtgactgg agttcagacg tgt      53

<210> SEQ ID NO 52

```
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 52
caagcagaag acggcatacg agataagacg gagtgactgg agttcagacg tgt            53

<210> SEQ ID NO 53
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 53
caagcagaag acggcatacg agatcgagtc ctgtgactgg agttcagacg tgt            53

<210> SEQ ID NO 54
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 54
caagcagaag acggcatacg agattcctca gggtgactgg agttcagacg tgt            53

<210> SEQ ID NO 55
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 55
caagcagaag acggcatacg agatgtacgg atgtgactgg agttcagacg tgt            53

<210> SEQ ID NO 56
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 56
caagcagaag acggcatacg agatcatctc tcgtgactgg agttcagacg tgt            53

<210> SEQ ID NO 57
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 57
caagcagaag acggcatacg agatgtcgga gcgtgactgg agttcagacg tgt            53

<210> SEQ ID NO 58
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 58
```
caagcagaag acggcatacg agatacggag aagtgactgg agttcagacg tgt        53

<210> SEQ ID NO 59
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 59
caagcagaag acggcatacg agataggaga tggtgactgg agttcagacg tgt        53

<210> SEQ ID NO 60
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 60
caagcagaag acggcatacg agatagtact cggtgactgg agttcagacg tgt        53

<210> SEQ ID NO 61
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 61
caagcagaag acggcatacg agatggactc tagtgactgg agttcagacg tgt        53

<210> SEQ ID NO 62
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 62 agcggaat                                                           8

<210> SEQ ID NO 63
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 63 gatcatgc                                                           8

<210> SEQ ID NO 64
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 64 aagacgga                                                           8

<210> SEQ ID NO 65
<211> LENGTH: 8
<212> TYPE: DNA

```
<213> ORGANISM: Artificial Sequence
<220> FEATURE:
<223> OTHER INFORMATION: Synthetic oligonucleotide

<400> SEQUENCE: 65 cgagtcct                                                                  8

<210> SEQ ID NO 66
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 66 tcctcagg                                                                  8

<210> SEQ ID NO 67
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 67 gtacggat                                                                  8

<210> SEQ ID NO 68
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 68 catctctc                                                                  8

<210> SEQ ID NO 69
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 69 gtcggagc                                                                  8

<210> SEQ ID NO 70
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 70 acggagaa                                                                  8

<210> SEQ ID NO 71
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 71 aggagatg                                                                  8
```

```
<210> SEQ ID NO 72
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 72 agtactcg                                                                 8

<210> SEQ ID NO 73
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 73 ggactcta                                                                 8

<210> SEQ ID NO 74
<211> LENGTH: 8
<212> TYPE: DNA
<213> ORGANISM: Artificial Sequence
<220> FEATURE:
<223> OTHER INFORMATION: Synthetic primer

<400> SEQUENCE: 74 attccgct                                                                 8

<210> SEQ ID NO 75
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 75 gcatgatg                                                                 8

<210> SEQ ID NO 76
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 76 tccgtctt                                                                 8

<210> SEQ ID NO 77
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 77 aggactcg                                                                 8

<210> SEQ ID NO 78
<211> LENGTH: 8
<212> TYPE: DNA
<213> ORGANISM: Artificial Sequence
<220> FEATURE:
```

<223> OTHER INFORMATION: Synthetic oligonucleotide

<400> SEQUENCE: 78 cctgagga                                                                   8

<210> SEQ ID NO 79
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 79 atccgtac                                                                   8

<210> SEQ ID NO 80
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 80 gagagatg                                                                   8

<210> SEQ ID NO 81
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 81 gctccgac                                                                   8

<210> SEQ ID NO 82
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 82 ttctccgt                                                                   8

<210> SEQ ID NO 83
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 83 catctcct                                                                   8

<210> SEQ ID NO 84
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 84 cgagtact                                                                   8

```
<210> SEQ ID NO 85
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 85 tagagtcc                                                                 8

<210> SEQ ID NO 86
<211> LENGTH: 37
<212> TYPE: DNA
<213> ORGANISM: Artificial Sequence
<220> FEATURE:
<223> OTHER INFORMATION: Synthetic primer

<400> SEQUENCE: 86
ccttagaaac cactgctaac tgaaagagac taagatt                                37

<210> SEQ ID NO 87
<211> LENGTH: 37
<212> TYPE: DNA
<213> ORGANISM: Artificial Sequence
<220> FEATURE:
<223> OTHER INFORMATION: Synthetic primer

<400> SEQUENCE: 87
atttggaaac caatgcttac taaatgagac taagacg                                37

<210> SEQ ID NO 88
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 88
gtgactggag ttcagacgtg tgctcttccg atctccttag aaaccactgc taactgaaag       60
agactaagat t                                                            71

<210> SEQ ID NO 89
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 89
gtgactggag ttcagacgtg tgctcttccg atctatttgg aaaccaatgc ttactaaatg       60
agactaagac g                                                            71

<210> SEQ ID NO 90
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 90
tttttttttt                                                              10

<210> SEQ ID NO 91
<211> LENGTH: 184
<212> TYPE: DNA
```

```
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (6)..(7)
<223> OTHER INFORMATION: a, c, t, g, unknown or other
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: modified_base
<222> LOCATION: (46)..(46)
<223> OTHER INFORMATION: a, c, t, g, unknown or other
<220> FEATURE:
<221> NAME/KEY: misc_feature
<222> LOCATION: (46)..(46)
<223> OTHER INFORMATION: n is a, c, g, or t

<400> SEQUENCE: 91
tagranntnt tttcactrca ctawtgagaa mttaagagat aatggncwaa arycacarag      60
agtatattca aarakaagta tagcacttyt tmyttrgaaa ccamtgctwa ctraawgaga     120
ctaagayktg tcccrtcaaa aatcctggac ctatgcctaa aacacatttc acaatccctg    180
aact                                                                 184

<210> SEQ ID NO 92
<211> LENGTH: 183
<212> TYPE: DNA
<213> ORGANISM: Unknown
<220> FEATURE:
<223> OTHER INFORMATION: HGB1 sequence

<400> SEQUENCE: 92
tagaaattgt tttcactgca ctattgagaa attaagagat aatggcaaaa gtcacaaaga     60
gtatattcaa aaagaagtat agcactttttt ccttagaaac cactgctaac tgaaagagac   120
taagatttgt cccgtcaaaa atcctggacc tatgcctaaa acacatttca caatccctga    180
act                                                                  183

<210> SEQ ID NO 93
<211> LENGTH: 181
<212> TYPE: DNA
<213> ORGANISM: Unknown
<220> FEATURE:
<223> OTHER INFORMATION: HBG2 sequence

<400> SEQUENCE: 93
taggattttt cactacacta atgagaactt aagagataat ggcctaaaac cacagagagt     60
atattcaaag ataagtatag cacttcttat ttggaaacca atgcttacta aatgagacta   120
agacgtgtcc catcaaaaat cctggaccta tgcctaaaac acatttcaca atccctgaac   180
t                                                                    181

<210> SEQ ID NO 94
<211> LENGTH: 40
<212> TYPE: DNA
<213> ORGANISM: Artificial Sequence
```

```
<220> FEATURE:
<223> OTHER INFORMATION: Synthetic oligonucleotide

<400> SEQUENCE: 94
cagccacttg aactctatac gtatagagtt caagtggctg                              40
```

METHODS OF ASSESSING NUCLEASE CLEAVAGE

CROSS-REFERENCE TO RELATED APPLICATIONS

This application is a U.S. National Entry claiming priority to International Application PCT/US2018/012652 filed on Jan. 5, 2018, which claims the benefit of U.S. Provisional Application Nos. 62/570,300, filed Oct. 10, 2017, 62/502,434, filed May 5, 2017 and 62/443,212, filed Jan. 6, 2017, the contents of each of which are hereby incorporated herein by reference in their entirety.

SEQUENCE LISTING

In accordance with 37 CFR 1.52(e)(5), a Sequence Listing in the form of an ASCII text file (entitled "2011271-0106_SL.txt," created on Oct. 7, 2019, and 25,457 bytes in size) is incorporated herein by reference in its entirety.

BACKGROUND

Nucleases such as zinc finger nucleases (ZFNs), transcription activator-like effector nucleases (TALENs), and clustered regularly-interspersed short palindromic repeat (CRISPR)-associated nucleases have become increasingly used because of their ability to be targeted to particular DNA sequences. The value of nucleases such as these as a tool for the treatment of inherited diseases is widely recognized. For example, the U.S. Food and Drug Administration (FDA) held a Science Board Meeting on Nov. 15, 2016 addressing the use of such systems and potential regulatory considerations raised by them. In that meeting, the FDA noted that while Cas9/guide RNA (gRNA) ribonucleoprotein (RNP) complexes may be customized to generate precise edits at a locus of interest, the complexes may also interact with, and cut at, other "off-target" loci. The potential for off-target cuts ("off-targets"), in turn, raises at least a potential regulatory consideration with respect to the approval of therapeutics utilizing these nucleases.

Common methods for analyzing repair outcomes of genome editing involve PCR amplification of a targeted genomic region and subsequent analysis, either by endonuclease cleavage at base mismatches or sequencing (Mashal et al. Nat. Genet. 1995; 9:177-183; Vouillot et al. G3 2015; 5:407-415; Hendel et al. Trends Biotechnol. 2015:33:132-140; Tykco et al. Mol. Cell. 2016; 63:355-370; Brinkman et al. Nucleic Acids Res. 2014; 42:e168). However, PCR-mediated assays are fundamentally unable to measure structural changes to the genome (e.g., deletions larger than 100 bp, inversions and translocations), in conjunction with small indels. Unintended translocations, and other structural changes, have been specifically cited for study in genome editing therapies by the NIH Recombinant DNA Advisory Committee (RAC) and the FDA (Atkins et al. RAC Review 2016; Witten, Cell and Gene Meeting on the Mesa, La Jolla, CA, 2016). Measuring structural changes has recently become more feasible using a method referred to as AMP-Seq (Anchored Multiplex PCR sequencing) that is intended for clinical detection of oncogenic translocations, and similar methods referred to as HTGTS (High Throughput, Genome-wide Translocation Sequencing) or LAM-HTGTS (Linear Amplification-Mediated-HTGTS) (Zheng et al. Nat. Med. 2014; 20:1479-1484; Chiarle et al. Cell 2011; 147: 107-119; Hu et al. Nat. Protocol. 2016; 11:853-871). GUIDE-seq, a modification of AMP-seq, is a powerful tool to capture de novo off-target editing by CRISPR RNA-guided nucleases (Tsai et al. Nat. Biotechnol. 2014; 33:187-197). All these methods utilize a target specific primer, in addition to an adapter ligated universal priming site on sheared DNA, to achieve "uni-directional" amplification, and sequencing. However, DNA shearing is a cumbersome step in library preparation used in all these methods. DNA shearing requires specialized equipment and it is not readily amenable to studies of large numbers of samples. Consequently, DNA shearing has not been broadly applied in the gene editing field. In addition, shearing DNA has been shown to induce DNA damage that results in base miscalling, which may be problematic when assessing gene editing frequencies at low levels (e.g.: less than 1%) (Chen et al. Science 2017; 355:752-6; Costello et al. Nucleic Acids Res. 2013; 41:1-12).

SUMMARY

The present disclosure provides, among other things, methods and systems for characterization of nuclease activity by fragmenting and tagging DNA using transposon compositions. In one aspect, the disclosure features a method comprising: (a) contacting a genomic DNA sample, obtained from a cell or tissue contacted with a site specific nuclease, with a transposon comprising a first detection sequence at the 5' end of the transposon, under conditions whereby the transposon is inserted into the genomic DNA and the genomic DNA is fragmented into a plurality of tagmented double-stranded nucleic acid fragments comprising the transposon attached to the 5' end of the nucleic acid fragments; (b) amplifying the tagmented nucleic acid fragments using (i) a first fixed primer comprising a nucleotide sequence complementary to a predetermined location in the genomic DNA and comprising a second detection sequence at its 5' end, and (ii) a second selective primer comprising a nucleotide sequence complementary to at least a portion of the first detection sequence, to form amplified nucleic acid fragments comprising the first detection sequence, the transposon attached to the 5' end of the nucleic acid fragments, and the second detection sequence; and (c) sequencing the amplified nucleic acid fragments.

In some embodiments, the first detection sequence comprises a first sequencing tag. In some embodiments, step (c) comprises contacting the amplified nucleic acid fragments with a first sequencing primer that hybridizes to the first sequencing tag. In some embodiments, the second detection sequence comprises a second sequencing tag. In some embodiments, step (c) comprises contacting the amplified nucleic acid fragments with a second sequencing primer that hybridizes to the second sequencing tag.

In some embodiments, the genomic DNA sample is obtained from a single cell.

In some embodiments, step (b) comprises using a plurality of first fixed primers, wherein each comprises a nucleotide sequence complementary to a different predetermined location in the genomic DNA. In some embodiments, step (b) comprises performing a plurality of amplification reactions, each reaction using a different first fixed primer. In some embodiments, each of the plurality of first fixed primers comprises a detection sequence comprising (i) the same sequencing tag and (ii) a unique barcode. In some embodiments, the plurality of first fixed primers are used in a multiplexing assay.

In some embodiments, the double-stranded nucleic acid fragments comprise about 500 to about 5000 bps, e.g., about 100 to about 4000 bps, e.g., about 500 to about 3000 bp.

In some embodiments, the site-specific nuclease is Cas9.

In another aspect, the disclosure features a method comprising: (a) contacting a genomic DNA sample obtained from a cell or tissue contacted with an RNA-guided nuclease under conditions favorable for cleavage of the genomic DNA by the nuclease; (b) contacting the cleaved genomic DNA with a transposon comprising a first detection sequence at the 5' end of the transposon, under conditions whereby the transposon is inserted into the cleaved genomic DNA and the cleaved genomic DNA is fragmented into a plurality of tagmented double-stranded nucleic acid fragments comprising the transposon attached to the 5' end of the nucleic acid fragments; (c) amplifying the tagmented nucleic acid fragments using (i) a first fixed primer comprising a nucleotide sequence complementary to a predetermined location in the genomic DNA and comprising a second detection sequence at its 5' end, and (ii) a second selective primer comprising a nucleotide sequence complementary to at least a portion of the first detection sequence, to form amplified nucleic acid fragments comprising the first detection sequence, the transposon attached to the 5' end of the nucleic acid fragments, and the second detection sequence; and (d) sequencing the amplified nucleic acid fragments.

In some embodiments, the first detection sequence comprises a first sequencing tag. In some embodiments, step (d) comprises contacting the amplified nucleic acid fragments with a first sequencing primer that hybridizes to the first sequencing tag. In some embodiments, the second detection sequence comprises a second sequencing tag. In some embodiments, step (d) comprises contacting the amplified nucleic acid fragments with a second sequencing primer that hybridizes to the second sequencing tag.

In some embodiments, the genomic DNA sample is obtained from a single cell.

In some embodiments, step (c) comprises using a plurality of first fixed primers, wherein each comprises a nucleotide sequence complementary to a different predetermined location in the genomic DNA. In some embodiments, step (c) comprises performing a plurality of amplification reactions, each reaction using a different first fixed primer. In some embodiments, each of the plurality of first fixed primers comprises a detection sequence comprising (i) the same sequencing tag and (ii) a unique barcode. In some embodiments, the plurality of first fixed primers are used in a multiplexing assay.

In some embodiments, the double-stranded nucleic acid fragments comprise about 500 to about 5000 bps, e.g., about 100 to about 4000 bps, e.g., about 500 to about 3000 bp.

In some embodiments, the RNA-guided nuclease is Cas9.

In another aspect, the disclosure features a method comprising: (a) contacting a genomic DNA sample obtained from a cell or tissue with a transposon comprising a first detection sequence at the 5' end of the transposon, under conditions whereby the transposon is inserted into the genomic DNA and the genomic DNA is fragmented into a plurality of tagmented double-stranded nucleic acid fragments comprising the transposon attached to the 5' end of the nucleic acid fragments, wherein the genomic DNA comprises a double-stranded oligonucleotide integrated into at least one site cleaved by a site specific nuclease; (b) amplifying the tagmented nucleic acid fragments using (i) a first fixed primer comprising a nucleotide sequence complementary to at least a portion of the double-stranded oligonucleotide and comprising a second detection sequence at its 5' end, and (ii) a second selective primer comprising a nucleotide sequence complementary to at least a portion of the first detection sequence, to form amplified nucleic acid fragments comprising the first detection sequence, the transposon attached to the 5' end of the nucleic acid fragments, and the second detection sequence; and (c) sequencing the amplified nucleic acid fragments.

In some embodiments, the site-specific nuclease is Cas9.

In another aspect, the disclosure features a method comprising: (a) contacting a genomic DNA sample obtained from a cell or tissue with an RNA-guided nuclease and a double-stranded oligonucleotide under conditions favorable for cleavage of the genomic DNA by the nuclease and integration of the double-stranded oligonucleotide into at least one cleavage site, thereby generating tagged genomic DNA comprising the integrated double-stranded oligonucleotide; (b) contacting the tagged genomic DNA with a transposon comprising a first detection sequence at the 5' end of the transposon, under conditions whereby the transposon is inserted into the tagged genomic DNA and the tagged genomic DNA is fragmented into a plurality of tagmented double-stranded nucleic acid fragments comprising the transposon attached to the 5' end of the nucleic acid fragments; (c) amplifying the tagmented nucleic acid fragments using (i) a first fixed primer comprising a nucleotide sequence complementary to at least a portion of the double-stranded oligonucleotide and comprising a second detection sequence at its 5' end, and (ii) a second selective primer comprising a nucleotide sequence complementary to at least a portion of the first detection sequence, to form amplified nucleic acid fragments comprising the first detection sequence, the transposon attached to the 5' end of the nucleic acid fragments, and the second detection sequence; and (d) sequencing the amplified nucleic acid fragments.

In some embodiments, the RNA-guided nuclease is Cas9.

In some embodiments, both strands of the double-stranded oligonucleotide are orthologous to the genomic DNA.

In some embodiments, each 5' end of the double-stranded oligonucleotide comprises a phosphate group. In some embodiments, each 3' end of the double-stranded oligonucleotide comprises a phosphorothioate linkage. In some embodiments, each 5' end of the double-stranded oligonucleotide comprises a phosphorothioate linkage. In some embodiments, the double-stranded oligonucleotide comprises 30-35 nucleotides or 60-65 nucleotides. In some embodiments, the double-stranded oligonucleotide is blunt-ended. In some embodiments, the double-stranded oligonucleotide comprises a 5' end having 1, 2, 3, or 4 overhanging nucleotides.

In some embodiments, the first detection sequence comprises a first sequencing tag. In some embodiments, sequencing comprises contacting the amplified nucleic acid fragments with a first sequencing primer that hybridizes to the first sequencing tag. In some embodiments, the second detection sequence comprises a second sequencing tag. In some embodiments, sequencing comprises contacting the amplified nucleic acid fragments with a second sequencing primer that hybridizes to the second sequencing tag.

In some embodiments, the double-stranded nucleic acid fragments comprise about 500 to about 5000 bps.

In some embodiments, the sequenced nucleic acid fragments comprise a translocation relative to a reference genomic DNA sample. In some embodiments, the genomic DNA sample comprises a virally-transduced sequence.

In some embodiments, methods further comprise a step of transducing a sequence into the genomic DNA using a viral vector before contacting the genomic DNA, the cleaved genomic DNA, or the tagged genomic DNA with the transposon.

In some embodiments, methods further comprise a step of comparing the sequenced nucleic acid fragments to a reference genomic DNA sample.

In some embodiments, at least one sequenced nucleic acid comprises a translocation, relative to the reference genomic DNA sample. In some embodiments, less than 1% of the sequenced nucleic acids comprise a translocation relative to the reference genomic DNA sample.

In another aspect, the disclosure features a library of tagmented nucleic acid fragments described herein. In another aspect, the disclosure features a system for sequencing target nucleic acid, e.g., DNA, e.g., genomic DNA, comprising transposase, primers, and/or capture probes described herein.

At least part of the processes, methods, systems, and techniques described herein including, but not limited to, computer-implemented processes for assessing nuclease cleavage, may be implemented as a computer program product that includes instructions that are stored on one or more non-transitory machine-readable storage media, and that are executable on one or more processing devices. Examples of non-transitory machine-readable storage media include, e.g., read-only memory, an optical disk drive, memory disk drive, random access memory, and the like. At least part of the processes, methods, systems, and techniques described herein may be implemented as an apparatus, method, or system that includes one or more processing devices and memory storing instructions that are executable by the one or more processing devices to perform stated operations.

BRIEF DESCRIPTION OF THE DRAWINGS

FIG. 1 depicts a schematic showing steps of an exemplary sequencing method for nuclease-modified genomic DNA.

FIG. 2A depicts a schematic showing an exemplary custom hyperactive Tn5 enzyme (Tn5*) with Unique Molecular Index (UMI) barcode, pooling barcode, and i5 sequence tag.

FIG. 2B depicts a schematic showing steps of an exemplary sequencing method for nuclease-modified genomic DNA.

FIG. 4 depicts primers used in an exemplary method. Illumina tails are underlined.

FIG. 5 depicts results of MiSeq reads for G1 and G2 targets using UDiTaS.

FIG. 15A depicts small indels at the site of guide 2. FIG. 15B depicts a large 1.1 kb deletion junction using guides 1 and 2. FIG. 15C depicts a large 1.1 kb inversion junction using guides 1 and 2. FIG. 15D depict a homologous junction using guide 2.

FIGS. 19A and 19B depict exemplary UDiTaS characterization of plasmid standards without carrier DNA.

DEFINITIONS

Figure 3:
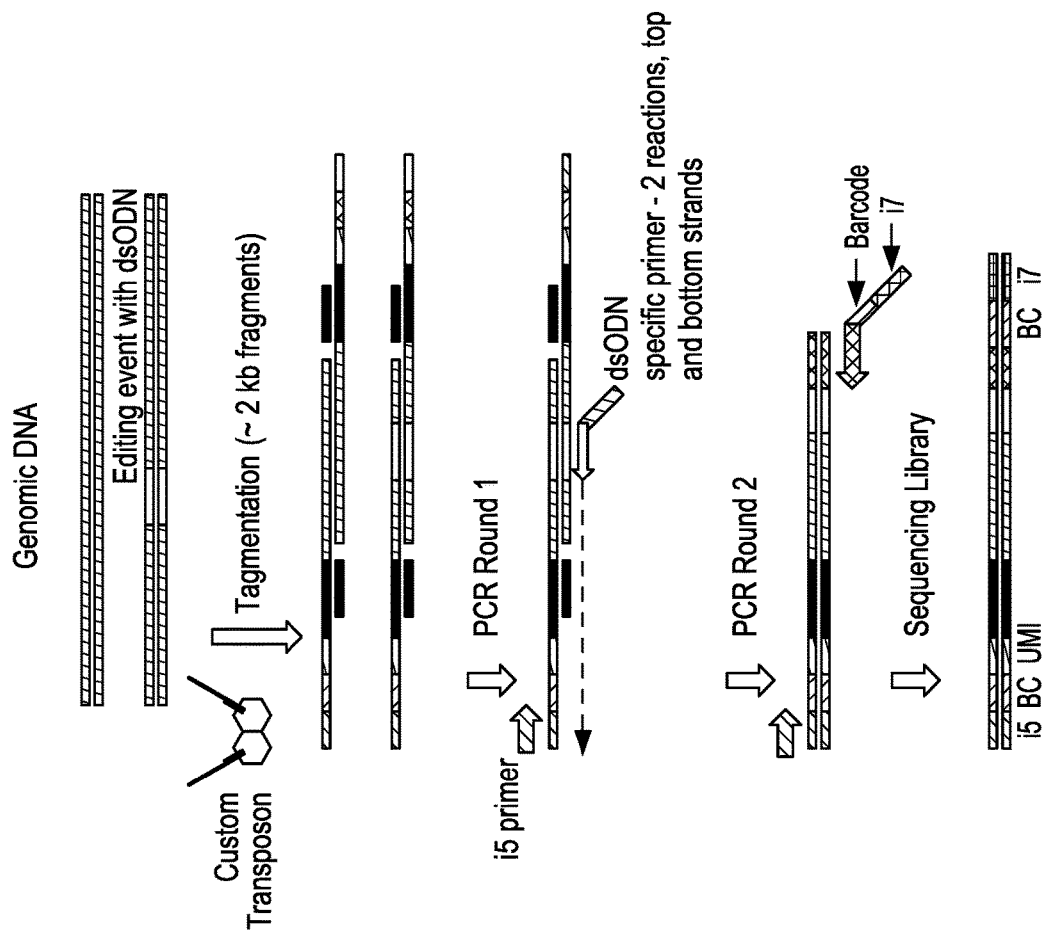
FIG. 3 depicts a schematic showing steps of an exemplary sequencing method using a primer complementary to a double stranded oligonucleotide insert (dsODN) to generate a sequencing library.

Throughout the specification, several terms are employed that are defined in the following paragraphs. Other definitions may also found within the body of the specification. In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

As used herein, the terms "about" and "approximately," in reference to a number, is used herein to include numbers that fall within a range of 20%, 10%, 5%, or 1% in either direction (greater than or less than) of the number unless otherwise stated or otherwise evident from the context (except where such number would exceed 100% of a possible value).

"Barcode," as used herein, refers to an oligonucleotide sequence. In some embodiments, random barcodes are not associated with any particular sequence and may be used, e.g., for quality control purposes. For example, in analyzing ligation products comprising a random barcode, the random barcode can be used to assess amplification bias of a particular ligation product. The over- or under-representation of a given random barcode among amplification products may indicate amplification bias. In some embodiments, data associated with such biased amplification products is excluded. Suitable sizes for the random barcode may vary depending on the embodiment. By way of non-limiting example, in some embodiments, the random barcode is 2, 3, 4, 5, 6, 7, 8, 9, 10, 11, or 12 nucleotides in length.

In some embodiments, a barcode is a Hamming code, i.e., an error-correcting barcodes. Hamming codes are sequences that can be used, for example, to identify a particular sample when samples are multiplexed. In some embodiments, there are collectively a defined number of possible Hamming codes, such as, by way of non-limiting example, up to 2, 3, 4, 5, 6, 7, 8, 9, 10, 11, 12, 13, 14, 15, 16, 17, 18, 19, or 20 possible Hamming codes.

In some embodiments, a barcode is a sample barcode. In some embodiments, a sample barcode is unique to a particular sample such that all members of a sequencing library derived from the particular sample comprise the same barcode. In some embodiments, a sample barcode is used to identify and/or classify results of sequence analysis, for example when multiple samples are analyzed together. In some embodiments, a sample barcode is referred to as a pooling barcode.

"Cleavage", as used herein, refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or cohesive ends.

As used herein, the term "degenerate," when used to refer to an oligonucleotide or nucleotide sequence, refers to one or more positions which may contain any of a plurality of different bases. Degenerate residues within an oligonucleotide or nucleotide sequence are denoted by standard IUPAC nucleic acid notation, as shown below:

| Character | Degenerate Bases |
| --- | --- |
| K | G or T/U |
| M | A or C |
| R | A or G |
| Y | C or T/U |
| S | C or G |
| W | A or T/U |
| B | C, G or T/U |
| V | A, C or G |
| H | A, C or T/U |
| D | A, G or T/U |
| N | A, C, G or T/U |

Unless otherwise specified, a degenerate residue does not imply a random or equal distribution of possible bases, e.g., an "N" residue does not denote an equal distribution of A, C, G and/or T/U residues.

As used herein, the term "detecting" a nucleic acid molecule or fragment thereof refers to determining the presence of the nucleic acid molecule, typically when the nucleic acid molecule or fragment thereof has been fully or partially separated from other components of a sample or composition, and also can include determining the charge-to-mass ratio, the mass, the amount, the absorbance, the fluorescence, or other property of the nucleic acid molecule or fragment thereof.

As used herein, the term "detectable label" refers to any element, molecule, functional group, compound, fragment or moiety that is detectable. In some embodiments, a detectable entity is provided or utilized alone. In some embodiments, a detectable entity is provided and/or utilized in association with (e.g., joined to) another agent. Examples of detectable entities include, but are not limited to: various ligands, radionuclides (e.g., $^3$H, $^{14}$C, $^{18}$F, $^{19}$F, $^{32}$P, $^{35}$S, $^{135}$I, $^{125}$I, $^{123}$I, $^{64}$Cu, $^{187}$Re, $^{111}$In, $^{90}$Y, $^{99m}$Tc, $^{177}$Lu, $^{89}$Zr etc.), fluorescent dyes (for specific exemplary fluorescent dyes, see below), chemiluminescent agents (such as, for example, acridinium esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold, and the like), biotin, dioxigenin, haptens, and proteins for which antisera or monoclonal antibodies are available.

As used herein, the terms "ligation", "ligating", and grammatical equivalents thereof refer to forming a covalent bond or linkage between the termini of two or more nucleic acids, e.g., oligonucleotides and/or polynucleotides, typically in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide. The term "ligation" also encompasses non-enzymatic formation of phosphodiester bonds, as well as the formation of non-phosphodiester covalent bonds between the ends of oligonucleotides, such as phosphorothioate bonds, disulfide bonds, and the like.

As used herein, the term "nuclease" refers to a polypeptide capable of cleaving the phosphodiester bonds between the nucleotide subunits of nucleic acids; the term "endonuclease" refers to a polypeptide capable of cleaving the phosphodiester bond within a polynucleotide chain.

As used herein, the terms "nucleic acid", "nucleic acid molecule" or "polynucleotide" are used herein interchangeably. They refer to a polymer of deoxyribonucleotides or ribonucleotides in either single- or double-stranded form, and unless otherwise stated, encompass known analogs of natural nucleotides that can function in a similar manner as naturally occurring nucleotides. The terms encompass nucleic acid-like structures with synthetic backbones, as well as amplification products. DNAs and RNAs are both polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

As used herein, the term "oligonucleotide" refers to a string of nucleotides or analogues thereof. Oligonucleotides may be obtained by a number of methods including, for example, chemical synthesis, restriction enzyme digestion or PCR. As will be appreciated by one skilled in the art, the length of an oligonucleotide (i.e., the number of nucleotides) can vary widely, often depending on the intended function or use of the oligonucleotide. Generally, oligonucleotides comprise between about 5 and about 300 nucleotides, for example, between about 15 and about 200 nucleotides, between about 15 and about 100 nucleotides, or between about 15 and about 50 nucleotides. Throughout the specification, whenever an oligonucleotide is represented by a sequence of letters (chosen from the four base letters: A, C, G, and T, which denote adenosine, cytidine, guanosine, and thymidine, respectively), the nucleotides are presented in the 5' to 3' order from the left to the right. In certain embodiments, the sequence of an oligonucleotide includes one or more degenerate residues described herein.

As used herein, the term "reference" describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

As used herein, the term "target site," refers to a nucleic acid sequence that defines a portion of a nucleic acid to which a binding molecule will bind, provided sufficient conditions for binding exist. In some embodiments, a target site is a nucleic acid sequence to which a nuclease described herein binds and/or that is cleaved by such nuclease. In some embodiments, a target site is a nucleic acid sequence to which a guide RNA described herein binds. A target site may be single-stranded or double-stranded. In the context of nucleases that dimerize, for example, nucleases comprising a FokI DNA cleavage domain, a target site typically comprises a left-half site (bound by one monomer of the nuclease), a right-half site (bound by the second monomer of the nuclease), and a spacer sequence between the half sites in which the cut is made. In some embodiments, the left-half site and/or the right-half site is between 10-18 nucleotides long. In some embodiments, either or both half-sites are shorter or longer. In some embodiments, the left and right half sites comprise different nucleic acid sequences. In the context of zinc finger nucleases, target sites may, in some embodiments, comprise two half-sites that are each 6-18 bp long flanking a non-specified spacer region that is 4-8 bp long. In the context of TALENs, target sites may, in some embodiments, comprise two half-sites sites that are each 10-23 bp long flanking a non-specified spacer region that is 10-30 bp long. In the context of RNA-guided (e.g., RNA-programmable) nucleases, a target site typically comprises a nucleotide sequence that is complementary to a guide RNA of the RNA-programmable nuclease, and a protospacer adjacent motif (PAM) at the 3' end or 5' end adjacent to the guide RNA-complementary sequence. For the RNA-guided nuclease Cas9, the target site may be, in some embodiments, 16-24 base pairs plus a 3-6 base pair PAM (e.g., NNN, wherein N represents any nucleotide). Exemplary target sites for RNA-guided nucleases, such as Cas9, are known to those of skill in the art and include, without limitation, NNG, NGN, NAG, and NGG, wherein N represents any nucleotide. In addition, Cas9 nucleases from different species (e.g., *S. thermophilus* instead of *S. pyogenes*) recognizes a PAM that comprises the sequence NGGNG. Additional PAM sequences are known, including, but not limited to NNA-GAAW and NAAR (see, e.g., Esvelt and Wang, Molecular Systems Biology, 9:641 (2013), the entire contents of which are incorporated herein by reference). For example, the target site of an RNA-guided nuclease, such as, e.g., Cas9, may comprise the structure [Nz]-[PAM], where each N is, independently, any nucleotide, and z is an integer between 1 and 50. In some embodiments, z is at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, or at least 50. In some embodiments, z is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, Z is 20.

As used herein, a "tag" refers to a non-target nucleic acid component, generally DNA, that provides a means of addressing a nucleic acid fragment to which it is joined. For example, in some embodiments, a tag is or comprises a nucleotide sequence that permits identification, recognition, and/or molecular or biochemical manipulation of the DNA to which the tag is attached (e.g., by providing a site for annealing an oligonucleotide, such as a primer for extension by a DNA polymerase, or an oligonucleotide for capture or for a ligation reaction). The process of joining a tag to a DNA molecule is sometimes referred to herein as "tagging" and DNA that undergoes tagging or that contains a tag is referred to as "tagged" (e.g., "tagged DNA").

As used herein, a "transposase" means an enzyme that is capable of forming a functional complex with a transposon-containing composition (e.g., transposons) and catalyzing insertion or transposition of the transposon into a double-stranded target nucleic acid, e.g., DNA, with which it is incubated in an in vitro transposition reaction.

As used herein, a "transposon" means a double-stranded nucleic acid, e.g., DNA, that includes nucleotide sequences (the "transposon sequences") that are necessary to form a complex with a transposase or integrase enzyme that is functional in an in vitro transposition reaction. A transposon forms a "complex" or a "synaptic complex" or a "transposome complex" or a "transposome composition" with a transposase or integrase that recognizes and binds to the transposon, and which complex is capable of inserting or transposing the transposon into target DNA with which it is incubated in an in vitro transposition reaction. A transposon exhibits two complementary sequences consisting of a "transferred transposon sequence" or "transferred strand" and a "nontransferred transposon sequence" or "nontransferred strand". The 3'-end of a transferred strand is joined or transferred to target DNA in an in vitro transposition reaction. The nontransferred strand, which exhibits a transposon sequence that is complementary to the transferred transposon sequence, is not joined or transferred to the target DNA in an in vitro transposition reaction. In some embodiments, a transposon comprises a detection sequence. In some embodiments, a detection sequence comprises additional sequences, for example, a UMI barcode, a pooling or sample barcode and/or a sequence tag.

As used herein, a "transposon joining end" means the end of a double stranded transposon DNA, which joins to a target DNA at an insertion site. The transposon joining end does not refer to the strand actually ligating to a target DNA. For example the 3' end of the transposon MuA joining end ligates to the 5' end of the target DNA leaving a gap between the 3' end of the target DNA and 5' end of transposon joining end.

As used herein, the term "transposase" means an enzyme capable of forming a functional complex with a transposon or transposons needed in a transposition reaction including integrases from retrotransposons and retroviruses.

As used herein, a "transposition reaction" is a reaction wherein a transposon inserts into a target DNA at random or at almost random sites. Essential components in a transposition reaction are a transposon and a transposase or an integrase enzyme or some other components needed to form a functional transposition complex. All transposition systems capable of inserting amplification primer sites in a random or in an almost random manner are useful in methods described herein (Craig, Science 270: 253-254, 1995). Examples of such systems are Ty1 (Devine and Boeke, Nucleic Acids Research, 1994, 22(18): 3765-3772, and International Patent Application WO 95/23875), Transposon Tn7 (Craig, Curr. Top. Microbiol. Immunol. 204: 27-48, 1996), $Tn_{10}$ and IS10 (Kleckner et al. Curr. Top. Microbiol. Immunol., 1996, 204: 49-82), Mariner transposase (Lampe et al., EMBO J., 1996, 15(19): 5470-5479), Tc1 (Vos et al., Genes Dev., 1996,10(6): 755-61), Tn5 (Park et al., J. Korean Soc. Microbiol. 27:381-389 (1992)), P element (Kaufman and Rio, Cell, 1992, 69(1): 27-39) and Tn3 (Ichikawa and Ohtsubo, J. Biol. Chem., 1990, 265(31): 18829-32), bacterial insertion sequences (Ohtsubo and Sekine, Curr. Top. Microbiol. Immunol., 1996,204: 1-26), retroviruses (Varmus Retroviruses. in Mobile DNA. Berg D. E. and Howe M. M. eds. American society for microbiology, Washington D.C. pp. 53-108 (1989)) and retrotransposon of yeast (Boeke, Berg D. E. and Howe M. M. eds. American society for microbiology, Washington D. C. pp. 335-374 (1989)).

As used herein, the term "sequencing tag" means a tag that is or comprises a sequence for the purposes of facilitating sequencing of a nucleic acid to which the tag is joined (e.g., to provide a priming site for sequencing by synthesis, or to provide annealing sites for sequencing by ligation, or to provide annealing sites for sequencing by hybridization). For example, in some embodiments, a sequencing tag provides a site for priming DNA synthesis of a DNA fragment or the complement of a DNA fragment. In some embodiments, a sequencing tag is a full-length Illumina forward adapter (i5). In some embodiments, a sequencing tag is a full-length Illumina reverse adapter (i7).

As used herein, the term "amplification tag" means a tag that is or comprises a sequence for the purpose of facilitating amplification of a nucleic acid to which said tag is appended. For example, in some embodiments, an amplification tag provides a priming site for a nucleic acid amplification reaction using a DNA polymerase (e.g., a PCR amplification reaction or a strand-displacement amplification reaction, or a rolling circle amplification reaction), or a ligation template for ligation of probes using a template-dependent ligase in a nucleic acid amplification reaction (e.g., a ligation chain reaction).

As used herein, the terms "amplify", "amplified", or "amplifying" as used in reference to a nucleic acid or nucleic acid reactions, refers to in vitro methods of making copies of a particular nucleic acid, such as a target nucleic acid, or a tagged nucleic acid produced, for example, by a method described herein. Numerous methods of amplifying nucleic acids are known in the art, and amplification reactions include polymerase chain reactions, ligase chain reactions, strand displacement amplification reactions, rolling circle amplification reactions, transcription-mediated amplification methods such as NASBA (e.g., U.S. Pat. No. 5,409, 818), loop mediated amplification methods (e.g., "LAMP" amplification using loop-forming sequences, e.g., as described in U.S. Pat. No. 6,410,278). A nucleic acid that is amplified can be DNA comprising, consisting of, or derived from DNA or RNA or a mixture of DNA and RNA, including modified DNA and/or RNA. The products resulting from amplification of a nucleic acid molecule or molecules (i.e., "amplification products"), whether the starting nucleic acid is DNA, RNA or both, can be either DNA or RNA, or a mixture of both DNA and RNA nucleosides or nucleotides, or they can comprise modified DNA or RNA nucleosides or nucleotides. A "copy" does not necessarily mean perfect sequence complementarity or identity to the target sequence. For example, copies can include nucleotide analogs such as deoxyinosine or deoxyuridine, intentional sequence alterations (such as sequence alterations introduced through a primer comprising a sequence that is hybridizable, but not complementary, to the target sequence), and/or sequence errors that occur during amplification.

As used herein, a "primer" is an oligonucleotide, generally with a free 3'-OH group, that can be extended by a nucleic acid polymerase. For a template-dependent polymerase, generally at least the 3'-portion of a primer is complementary to a portion of a template nucleic acid, to which the oligonucleotide "binds" (or "complexes", "anneals", or "hybridizes"), by hydrogen bonding and other molecular forces, to the template to give a primer/template complex for initiation of synthesis by a DNA polymerase, and which is extended (i.e., "primer extended") by the addition of covalently bonded bases linked at its 3'-end which are complementary to the template in the process of DNA synthesis. The result is a primer extension product. Template-dependent DNA polymerases (including reverse transcriptases) generally require complexing of an oligonucleotide primer to a single-stranded template to initiate DNA synthesis ("priming"), but RNA polymerases generally do not require a primer for synthesis of RNA that is complementary to a DNA template (transcription).

A "fixed primer" as used herein means a primer having a sequence complementary to a known sequence in a target or template nucleic acid, e.g., DNA.

A "selective primer" as used herein means a primer having a sequence complementary to a sequence of the transposon DNA (complementary to that strand having 5' end at the joining). A selective primer is in 5'->3' direction towards a target or template nucleic acid, e.g., DNA.

DETAILED DESCRIPTION

The present disclosure provides, among other things, methods and systems for characterization of nuclease activity by fragmenting and tagging DNA using transposon compositions. The methods, compositions, and kits described herein are useful for generating and amplifying nucleic acid fragments from target or template nucleic acids (e.g., DNA, e.g., genomic DNA), which have been subjected to cleavage with a nuclease described herein. In some embodiments, such amplified nucleic acid fragments can be sequenced, e.g., to characterize nuclease activity.

The methods, compositions, and kits described herein are particularly useful to assess large insertions, large deletions, inversions, and/or translocations within a target or template nucleic acid. For example, disclosed methods, compositions, and/or kits can detect chromosomal rearrangements (e.g., large insertions, large deletions, inversions, and/or translocations) that are present in abundances of less than 5%, less than 1%, less than 0.5%, less than 0.3%, less than 0.1%, less than 0.05%, and/or less than 0.01% of a sample (e.g., a genomic DNA sample). The methods of the disclosure are advantageous over known methods including, e.g., Anchored Multiplex PCR sequencing (AMP-seq) (see, e.g., Zheng et al., Nat Med. 2014 December; 20(12):1479-84; Adey et al., Genome Biology, 11(12), R119 (2010)).

In some embodiments, the disclosure provides Uni-Directional Targeted Sequencing ("UDiTaS"). In certain embodiments described herein, such method utilizes a single primer targeting approach, e.g., a single adapter complexed with a transposase, a unique molecular index (UMI) (e.g., a UMI barcode) on adapter and/or a pooling or sample barcode, labeling of DNA directly with UMI during tagmentation, and a PCR tagmented product. In some embodiments, a second round our PCR adds an adapter (e.g., a reverse Illumina adapter, e.g., i7) and an additional sample barcode. In certain embodiments, single primer extension through a target site to end of genomic DNA fragment can identify translocation events. Such methods are also adaptable to multiplexing as described herein.

The strategies, methods, and reagents provided herein can be utilized to analyze cleavage and/or repair events for any site-specific nuclease, for example, Zinc Finger Nucleases (ZFNs), Transcription Activator-Like Effector Nucleases (TALENs), homing endonucleases, organic compound nucleases, and enediyne antibiotics (e.g., dynemicin, neocarzinostatin, calicheamicin, esperamicin, bleomycin). Suitable nucleases in addition to the ones described herein will be apparent to those of skill in the art based on this disclosure.

Further, the methods, reagents, and strategies provided herein allow those of skill in the art to identify, design, and/or select nucleases with enhanced specificity and/or to minimize the off-target effects of any given nuclease (e.g., site-specific nucleases such as ZFNs, and TALENS as well as RNA-programmable nucleases, for example Cas9). While of particular relevance to DNA and DNA-cleaving nucleases, the inventive concepts, methods, strategies, and reagents provided herein are not limited in this respect, but can be applied to any nucleic acid:nuclease pair.

Uni-Directional Targeted Sequencing (UDiTaS)

In some aspects, the present disclosure provides methods of assessing nuclease and/or nuclease variants for ability to cleave a particular target site. In some embodiments, UDiTaS removes biases associated with variable-length PCR amplification, and measures structural changes in addition to small insertion and deletion events (indels), in a single reaction. In some embodiments, a UDiTaS method uses a custom designed Tn5 transposon comprising a full-length Illumina forward adapter (i5), a sample barcode and/or a unique molecular identifier (UMI) (FIG. 2A). In general, such methods comprise contacting a nucleic acid template (e.g., DNA, e.g., genomic DNA, e.g., genomic DNA that has been cleaved, modified, and/or edited using a nuclease described herein) with a transposon under conditions whereby the transposon is inserted into the nucleic acid template.

The conditions are sufficient for a transposition reaction to occur, e.g., in the presence of a transposase described herein. Such transposition reactions and conditions are known in the art (see, e.g., U.S. Pat. Nos. 6,593,113 and 9,080,211). In some embodiments, transposition conditions are selected with the desired fragment size in mind. The transposition reaction results in fragmentation of the nucleic acid template into a plurality of tagmented double-stranded nucleic acid fragments, where the 3' end of the transferred strand of the transposon is attached to the 5' end of the nucleic acid fragments. The transferred strand of the transposon comprises a first detection sequence at the 5' end of the transferred strand. In some embodiments, a first detection sequence comprises a UMI barcode, a pooling barcode and/or an adapter (full-length Illumina forward adapter (i5)).

Following the transposition reaction, the tagmented nucleic acid fragments are amplified, e.g., using PCR, using a set of primers. A first primer can be a fixed primer, comprising a nucleotide sequence complementary to a predetermined location in the genomic DNA. A first primer can also be a fixed primer, comprising a nucleotide sequence complementary to at least a portion of a double-stranded oligonucleotide as described herein. The first primer also includes a second detection sequence at its 5' end. A second primer is a selective primer, comprising a nucleotide sequence complementary to at least a portion of the first detection sequence. The amplification forms amplified nucleic acid fragments, which include (in 5' to 3' orientation): the first detection sequence, the transferred strand of the transposon attached to the 5' end of the nucleic acid fragments, and the second detection sequence.

In some embodiments, a second round of PCR is performed using a second selective primer comprising a nucleotide sequence complementary to at least a portion of the first detection sequence and a third selective primer comprising a nucleotide sequence complementary to at least a portion of the second detection sequence. In some embodiments, a third selective primer comprises a barcode (e.g., a pooling barcode) and/or a sequence tag (e.g., reverse Illumina adapter (i7)). Exemplary methods are depicted in FIGS. 1 and 2A-2C.

The amplified nucleic acid fragments can then be sequenced. For example, the first and second detection sequences can include sequencing tags described herein to facilitate sequencing. In some embodiments, the method can include a size separation step after tagmentation and before PCR.

In some embodiments, relative abundances of particular alleles (e.g., wild type having one or more indels and/or having one or more chromosomal rearrangements) in the genomic DNA sample are the same as relative abundances of those alleles in the amplified nucleic acid fragments.

In some embodiments, a plurality of tagmented double-stranded nucleic acid fragments can be a library of such fragments. In some embodiments, the library includes about $10^2$, $10^3$, $10^4$, $10^5$, $10^6$, $10^7$, $10^8$, $10^9$, $10^{10}$ or more nucleic acid fragments. In some embodiments, methods described herein can sequence 500 bp, 1000 bp, 1500 bp, 2000 bp, 2500 bp, 3000 bp, 3500 bp, 4000 bp, 5000 bp, 6000 bp, 7000 bp, 8000 bp, 9000 bp, 10000 bp, or more.

In some embodiments, the method comprises (a) contacting a nucleic acid template with a transposon comprising a first detection sequence at the 5' end of the transposon, under conditions whereby the transposon is inserted into the nucleic acid template and the nucleic acid template is fragmented into a plurality of tagmented double-stranded nucleic acid fragments comprising the transposon attached to the 5' end of the nucleic acid fragments; (b) amplifying the tagmented nucleic acid fragments using (i) a first fixed primer comprising a nucleotide sequence complementary to a predetermined location in the nucleic acid template and comprising a second detection sequence at its 5' end, and (ii) a second selective primer comprising a nucleotide sequence complementary to at least a portion of the first detection sequence, to form amplified nucleic acid fragments comprising the first detection sequence, the transposon attached to the 5' end of the nucleic acid fragments, and the second detection sequence; and (c) sequencing the amplified nucleic acid fragments, wherein the nucleic acid template has been modified using an RNA-guided nuclease.

In some embodiments, amplified nucleic acid fragments of step (b) are amplified using a second selective primer comprising a nucleotide sequence complementary to at least a portion of the first detection sequence and a third selective primer comprising a nucleotide sequence complementary to at least a portion of the second detection sequence. In some embodiments, a third selective primer comprises a barcode (e.g., a pooling barcode) and/or a sequence tag (e.g., reverse Illumina adapter (i7)).

In some embodiments, the method comprises (a) contacting a genomic DNA sample obtained from a cell or tissue with an RNA-guided nuclease and a double-stranded oligonucleotide (dsODN) under conditions favorable for cleavage of the genomic DNA by the nuclease and integration of the double-stranded oligonucleotide into at least one cleavage site, thereby generating tagged genomic DNA comprising the integrated double-stranded oligonucleotide; (b) contacting the tagged genomic DNA with a transposon comprising a first detection sequence at the 5' end of the transposon, under conditions whereby the transposon is inserted into the tagged genomic DNA and the tagged genomic DNA is fragmented into a plurality of tagmented double-stranded nucleic acid fragments comprising the transposon attached to the 5' end of the nucleic acid fragments; (c) amplifying the tagmented nucleic acid fragments using (i) a first fixed primer comprising a nucleotide sequence complementary to at least a portion of the double-stranded oligonucleotide and comprising a second detection sequence at its 5' end, and (ii) a second selective primer comprising a nucleotide sequence complementary to at least a portion of the first detection sequence, to form amplified nucleic acid fragments comprising the first detection sequence, the transposon attached to the 5' end of the nucleic acid fragments, and the second detection sequence; and (d) sequencing the amplified nucleic acid fragments.

In some embodiments, amplified nucleic acid fragments of step (c) are amplified using a second selective primer comprising a nucleotide sequence complementary to at least a portion of the first detection sequence and a third selective primer comprising a nucleotide sequence complementary to at least a portion of the second detection sequence. In some embodiments, a third selective primer comprises a barcode (e.g., a pooling barcode) and/or a sequence tag (e.g., reverse Illumina adapter (i7)). An exemplary method is depicted in FIG. 3.

In some embodiments, sequences obtained from the step of sequencing are compared to one or more sequences from a reference genomic DNA sample (e.g., a control sample).

For example, presently disclosed methods can be used as a diagnostic tool.

For example, a decision can be made based on sequence(s) obtained from the step of sequencing and/or based on a comparison of such sequence(s) to a sequence(s) from a reference genomic DNA sample.

In some embodiments, a nucleic acid template is contacted with a transposon under conditions and for sufficient time wherein multiple insertions into the target DNA occur, each of which results in joining of a first tag comprising or consisting of the transferred strand to the 5' end of a nucleotide in the target DNA, thereby fragmenting the target DNA and generating a population of annealed 5'-tagged DNA fragments, each of which has the first tag on the 5'-end.

In some embodiments, the amount of the transposase and the transposon or of the transposome composition used in the in vitro transposition reaction is between about 1 picomole and about 25 picomoles per 50 nanograms of target DNA per 50-microliter reaction. In some embodiments, the amount of the transposase and the transposon composition or of the transposome composition used in the in vitro transposition reaction is between about 5 picomoles and about 50 picomoles per 50 nanograms of target DNA per 50-microliter reaction. In some embodiments wherein the transposase is a hyperactive Tn5 transposase or MuA transposase, the final concentrations of the transposase and the transposon or of the transposome used in the in vitro transposition reaction is at least 250 nM; in some other embodiments, the final concentrations of hyperactive Tn5 transposase or MuA transposase and of their respective transposon end composition or transposome composition is at least 500 nM.

In some embodiments, the reaction time for the in vitro transposition reaction is two hours or less, one hour or less, 30 minutes or less, or 15 minutes or less. In some embodiments, the reaction time for the in vitro transposition reaction is 5 minutes or less. In some embodiments wherein the transposome composition comprises a hyperactive Tn5 transposase, the reaction time for the in vitro transposition reaction is 5 minutes or less.

The transposon can be labeled with a detectable label. Such a label may be useful, for example, to capture, purify, and/or enrich for nucleic acids containing the transposon. Any of a wide variety of detectable labels may be suitable for this purpose, including, for example, biotin, a fluorescent label, an antibody label, an antibody fragment label, and/or other detectable labels mentioned herein.

In some embodiments, sequencing tags are used for generation of templates for next-generation sequencing for a particular sequencing platform (e.g., sequencing tags for: a ROCHE 454A or 454B sequencing platform; for an ILLUMINA SOLEXA sequencing platform; for an APPLIED BIOSYSTEMS SOLID™ sequencing platform; for a PACIFIC BIOSCIENCES' SMRT™ sequencing platform; for a POLLONATOR POLONY sequencing platform; for a HELICOS sequencing platform; for a COMPLETE GENOMICS sequencing platform; for an INTELLIGENT BIOSYSTEMS sequencing platform; or for any other sequencing platform). In some embodiments, a sequencing tag is a full-length Illumina forward (i5) adapter. In some embodiments, a sequencing tag is a full-length Illumina reverse (i7) adapter.

A wide variety of enzymes and kits are available for performing an amplification reaction by PCR. For example, in some embodiments, a PCR amplification is performed using either the FAILSAFE™ PCR System or the MASTERAMP™ Extra-Long PCR System from EPICENTRE Biotechnologies, Madison, Wis., as described by the manufacturer. These systems permit rapid optimization of the PCR reaction conditions using a series of 2×PCR PreMixes provided with each system to identify the optimal PreMix for a particular template and primer pair. However, the disclosure is not limited to the use of those products or conditions for the amplification reaction and any suitable thermostable DNA polymerase and reaction mixture that permits amplification of the sequence between the primer that anneals to the target sequence and the primer that anneals to the transposon can be used. A non-strand displacing polymerase or a strand-displacing polymerase can be used in any of the methods described herein.

Protocols for amplification of nucleic acids are known in the art and can include, e.g., one round of amplification or multiple rounds of amplification. For example, a first amplification round can be followed by a second amplification round with or without one or more processing (e.g., cleanup, concentrating, etc.) steps in between the two rounds of amplification. Additional rounds of amplification may be used in some embodiments, with or without one or more processing steps in between.

The number of amplification cycles can be varied depending on the embodiment. For example, each round of amplification can comprise at least 8, 10, 12, 14, 16, 18, 20, 22, 24, 26, 28, 30, or 32 cycles. In embodiments involving more than one round of amplification, the number of amplification cycles used in each round can be the same or it can be different. In cases in which two rounds of amplification are used and the number of amplification cycles in the two rounds differ, the first round can comprise more cycles or it may comprise fewer cycles than the second round. As an example, a first round of amplification can comprise 12 cycles and a second round of amplification can comprise 15 cycles. As another example, a first round of amplification can comprise 10 cycles and a second round of amplification can comprise 12 cycles.

When more than one round of amplification is used, the same or different set of primers can be used. For example, a nested amplification scheme (e.g., nested PCR) can be used.

In some embodiments, involving two rounds of amplification, a forward primer in one round is used as a forward primer in another round, but the reverse primers in the two rounds differ. Alternatively, the forward and reverse primers can be different in the two rounds. Alternatively, a reverse primer in one round is used as a reverse primer in the other round, but the forward primers in the two rounds differ.

Final concentrations of primers in amplification reactions can vary depending on the embodiment. When two or more primers are used together, e.g., in a single-round amplification or in the same round of a multi-round amplification, the concentrations of the primers can differ or they can be the same. For example, primers can be present in an amplification reaction at concentrations ranging from between about 100 nM and about 500 nM, e.g., about 100 nM, about 150 nM, about 200 nM, about 250 nM, about 300 nM, about 350 nM, about 400 nM, about 450 nM, or about 400 nM.

In some embodiments, an excess of one primer relative to another primer present during the same round of amplification is used. In some embodiments, at least one primer in at least one round of amplification is present at a concentration greater than 500 nM, e.g., 1 µM, 2 µM, 3 µM, 4 µM, 5 µM etc.

In some embodiments, reactions are carried out in a buffer containing magnesium, e.g., $MgCl_2$. Examples of suitable concentrations of magnesium (e.g., $MgCl_2$) include, but are not limited to, about 1 mM, about 1.5 mM, about 2 mM, about 2.5 mM, about 3 mM, about 3.5 mM, about 4 mM, about 4.5 mM, or about 5 mM.

In some embodiments, a mix of dNTPs is used at a concentration ranging from about 0.2 mM to about 0.8 mM, e.g., about 0.2 mM, about 0.3 mM, about 0.4 mM, about 0.5 mM, about 0.6 mM, about 0.7 mM, or about 0.8 mM.

Total volumes of amplification reactions can vary depending on the embodiment. For example, reaction volumes between about 10 µL and about 200 µL, e.g., about 10 µL, about 15 µL, about 20 µL, about 25 µL, about 30 µL, about 35 µL, about 40 µL, about 45 µL, about 50 µL, about 55 µL, about 60 µL, about 65 µL, about 70 µL, about 75 µL, about 80 µL, about 85 µL, about 90 µL, about 95 µL, about 100 µL, about 110 µL, about 120 µL, about 130 µL, about 140 µL, about 150 µL, about 160 µL, about 170 µL, about 180 µL, about 190 µL, or about 200 µL can be used.

Generally, a cycle of amplification comprises a denaturation phase (during which strands of nucleic acids are separated), an annealing phase (during which primers anneal to nucleic acid templates), and an extension phase (during which an annealed primer is extended using a nucleic acid template).

Temperatures for each phase differ, with the temperature used during the denaturation phase tending to be higher than that of the extension phase, which tends to be higher than that used during annealing phase.

For example, suitable temperatures for the denaturation phase can range from about 90° C. to about 100° C., e.g., about 90° C., about 91° C., about 92° C., about 93° C., about 94° C., about 95° C., about 96° C., about 97° C., about 98° C., about 99° C., or about 100° C.

For example, suitable temperatures for the annealing phase can range from about 50° C. to about 65° C., e.g., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., or about 65° C.

For example, suitable temperatures for the extension phase can range from about 68° C. to about 80° C., e.g., about 68° C., about 69° C., about 70° C., about 71° C., about 72° C., about 73° C., about 74° C., about 75° C., about 76° C., about 77° C., about 78° C., about 79° C., or about 80° C.

The durations of each phase during a single cycle can vary. Generally, the durations of the annealing and extension phases can be longer than that of the denaturation phase.

For example, the denaturation phase can last between about 4 seconds and about 20 seconds, e.g., about 4 seconds, about 5 seconds, about 6 seconds, about 7 seconds, about 8 seconds, about 9 seconds, about 10 seconds, about 11 seconds, about 12 seconds, about 13 seconds, about 14 seconds, about 15 seconds, about 16 seconds, about 17 seconds, about 18 seconds, about 19 seconds, or about 20 seconds in each cycle.

The durations of the annealing and extension phases can be the same or different. For example, an annealing or an extension phase can last between about 20 seconds and about 2 minutes, e.g., about 20 seconds, about 25 seconds, about 30 seconds, about 35 seconds, about 40 seconds, about 45 seconds, about 50 seconds, about 55 seconds, about 60 seconds, about 65 seconds, about 70 seconds, about 75 seconds, about 80 seconds, about 85 seconds, about 90 seconds, about 95 seconds, about 100 seconds, about 105 seconds, about 110 seconds, or about 120 seconds in each cycle.

In embodiments in which more than one round of amplification is used, one or more processing steps can be used between rounds. For example, one or more cleanup and/or concentration steps can be used. Suitable cleanup steps include, but are not limited to, treatment with Proteinase K, treatment with chemical denaturants of proteins (e.g., urea), bead-based methods (e.g., using a Solid Phase Reversible Immobilization technique), on-column DNA cleanup methods, etc. DNA cleanup and/or concentrator kits are commercially available and include, for example, kits from Zymo Research, Thermo Fisher Scientific, Sigma Aldrich, etc.

For example, one or more steps to inactivate a component of the reaction can be used, e.g., inactivation of an enzyme such as a polymerase by heat, a change in pH, and/or a chemical.

The disclosure is also not limited to the use of PCR to amplify DNA fragments. Any suitable amplification method (e.g., rolling circle amplification, riboprimer amplification (e.g., U.S. Pat. No. 7,413,857), ICAN, UCAN, ribospia, terminal tagging (U.S. Patent Application No. 20050153333), Eberwine-type aRNA amplification or strand-displacement amplification) that amplifies the same sequence, and generates a suitable composition and amount of amplification product for the intended purpose can be used in embodiments of the present disclosure. For example, some strand displacement methods that can be used are described in PCT Patent Publication Nos. WO 02/16639; WO 00/56877; and AU 00/29742; of Takara Shuzo Company, Kyoto, Japan; U.S. Pat. Nos. 5,523,204; 5,536,649; 5,624,825; 5,631,147; 5,648,211; 5,733,752; 5,744,311; 5,756,702; and 5,916,779 of Becton Dickinson and Company; U.S. Pat. Nos. 6,238,868; 6,309,833; and 6,326,173 of Nanogen/Becton Dickinson Partnership; U.S. Pat. Nos. 5,849,547; 5,874,260; and 6,218,151 of Bio Merieux; U.S. Pat. Nos. 5,786,183; 6,087,133; and 6,214,587 of Gen-Probe, Inc.; U.S. Pat. No. 6,063,604 of Wick et al.; U.S. Pat. No. 6,251,639 of Kurn; U.S. Pat. No. 6,410,278; and PCT Publication No. WO 00/28082 of Eiken Kagaku Kabushiki Kaishi, Tokyo, Japan; U.S. Pat. Nos. 5,591,609; 5,614,389; 5,773,733; 5,834,202; and 6,448,017 of Auerbach; and U.S. Pat. Nos. 6,124,120; and 6,280,949 of Lizardi.

Genomic DNA

Genomic DNA samples used in methods disclosed herein can generally be obtained from any type of cell and/or tissue e.g., primary cells and/or tissues, cells or tissues cultured for at least a period of time, or a combination of primary and cultured cells and/or tissues.

In some embodiments, UDiTaS is performed on genomic DNA from a single cell. For example, genomic DNA from a single cell can be amplified before performing UDiTaS. Whole genome amplification methods are known in the art. Any of a variety of protocols and/or commercially available kits may be used. Examples of commercially available kits include, but are not limited to, the REPLI-g Single Cell Kit from QIAGEN, GENOMEPLEX® Single Cell Whole Genome Amplification Kit from Sigma Aldrich, Ampli1™ WGA Kit from Silicon Biosystems, and illustra Single Cell GenomiPhi DNA Amplification Kit from GE Healthcare Life Sciences. Thus, in some embodiments, even though UDiTaS is performed on genomic DNA from a single cell, it is still possible to perform a plurality of reactions on the genomic DNA, e.g., a plurality of reactions, each reaction using a different fixed primer, as described further herein.

Methods of the disclosure can also be performed using a genomic DNA sample comprising a virally-transduced sequence, and/or comprising a double-stranded oligonucleotide described herein. For example, methods of the disclosure can comprise a step of transducing a sequence into genomic DNA using a viral vector, and/or inserting a double-stranded oligonucleotide into genomic DNA as described herein. This step of transducing a sequence is generally performed before the step of contacting the genomic DNA with a transposon.

In some embodiments, genomic DNA samples are obtained from samples that do not contain live cells and/or tissues or contain cells and/or tissues in trace amounts. For example, methods of the present disclosure can be used on forensic DNA samples, such as, but not limited to, blood, bone, fingernail, hair, teeth, swab (such as, for example, buccal swab, genital swab, cervical swab, anal swab, etc.), and urine samples. Samples from used gauze or wound dressings can also be used.

Alternatively or additionally, methods disclosed herein can be used with genomic DNA samples from eukaryotic cells and/or tissues or from prokaryotic cells. For example, methods of the present disclosure can be performed using genomic DNA from microorganisms and/or from isolates from patients (e.g., patients receiving antibiotics). In some embodiments, genomic DNA from microbial communities and/or one or more microbiomes is used, e.g., for metagenomic mining. (See, for example, Delmont et al, "Metagenomic mining for microbiologists," ISME J. 2011 December; 5(12):1837-43.)

Genomic DNA can be prepared using any of a variety of suitable methods, including, for example, certain manipulations to cells and/or tissues described herein. Exemplary, non-limiting manipulations include contacting a cell and/or tissue with a nuclease (e.g., a site-specific nuclease and/or an RNA-guided nuclease) or a genome editing system comprising such a nuclease.

Detection Sequences

Detection sequences, as used herein, refer to sequence elements that may be present on a nucleic acid template, transposon, and/or primer described herein, and that facilitate recovery and/or detection of nucleic acids, or nucleic acid fragments, containing them. In some embodiments, one or more detection sequences facilitate or mediate capture by an oligonucleotide array and/or facilitate or mediate sequencing, e.g., sequencing of ligation products described herein.

In some embodiments, detection sequences facilitate amplification and/or sequencing. In some embodiments, detection sequences comprise one or more sequences that can be recognized by amplification and/or sequencing primers.

In some embodiments, a detection sequence comprises a UMI. In some embodiments, a detection sequence comprises a barcode. In some embodiments, a detection sequence comprises a sample barcode.

For example, in some embodiments, detection sequences comprise a sequence adapter for use in a sequencing method. In some embodiments, such sequence adapters comprise an amplification primer binding site and a sequencing primer binding site. In some embodiments, such sequence adapters comprising a primer binding site that serves as both an amplification and sequencing primer binding site. In some embodiments, the amplification primer binding site overlaps with the sequencing primer binding site.

In some embodiments, the amplification primer binding site is used for long-range amplification.

In some embodiments, sequence adapters further comprise a marker sequence that marks one end of the adapter.

In some embodiments, sequence adapters further comprise a barcode sequence. Detection sequences that can be used in the methods described herein are known in the art.

For example, sequencing adapters (e.g., MiSeq adapters) (available from Illumina) can be used as detection sequences (e.g., i5, i7).

Double-Stranded Oligonucleotides

As described herein, genomic DNA can include a double-stranded oligonucleotide. In some embodiments, a cell or tissue (from which a genomic DNA sample is obtained) is contacted with a double-stranded oligonucleotide and a nuclease (e.g., a site specific nuclease and/or an RNA-guided nuclease), e.g., under conditions favorable for cleavage of the genomic DNA by the nuclease. When a double-stranded oligonucleotide is used, the double-stranded oligonucleotide may be integrated into one or more nuclease cleavage sites within the genomic DNA. For example, a nuclease may induce one or more double-stranded breaks in the genomic DNA, and the double-stranded oligonucleotide may integrate into at least one of the one or more double-stranded breaks.

When genomic DNA includes a double-stranded oligonucleotide, methods described herein include using a fixed primer comprising a nucleotide sequence complementary to at least a portion of the double-stranded oligonucleotide, e.g., in an amplifying step.

Methods of designing suitable double-stranded oligonucleotides and integrating such oligonucleotides are known in the art, and are described, e.g., in WO 2015/200378A1, the entire contents of which are herein incorporated by reference.

In some embodiments, both strands of the double-stranded oligonucleotide are orthologous to the genomic DNA. For example, in embodiments in which the genomic DNA is human genomic DNA, both strands of the double-stranded oligonucleotide, if present, may be orthologous to human genomic DNA.

In some embodiments, the double-stranded oligonucleotide comprises a chemical modification. For example, each 5' end of the double-stranded oligonucleotide can comprise a phosphate group. Alternatively or additionally, the double-stranded oligonucleotide can contain phosphorothioate linkages. For example, each 3' end and/or each 5' end of the double-stranded oligonucleotide can comprise a phosphorothioate linkage.

In some embodiments, the double-stranded oligonucleotide is phosphorylated at both 5' ends, contains phosphorothioate linkages on both 5' ends, and contains phosphorothioate linkages on both 3' ends.

In some embodiments, the double stranded oligonucleotide comprises 30-35 nucleotides or 60-65 nucleotides.

Ends of the double-stranded oligonucleotide may be blunt or comprise an overhang (e.g., comprising a 5' end having 1, 2, 3, or 4 overhanging nucleotides), or one end may be blunt while the other comprises an overhang.

In some embodiments in which a double stranded oligonucleotide is used in a method comprising an amplifying step, the amplification step comprises performing a rolling circle PCR using a fixed primer that comprises a nucleotide sequence complementary to a predetermined sequence in the double-stranded oligonucleotide.

Detectable Labels

In some embodiments, a transposon, double-stranded oligonucleotide, and/or primer described herein is labeled with a detectable label. Such a label may be useful, for example, to capture, purify, and/or enrich for nucleic acids containing the transposon, double-stranded oligonucleotide, and/or primer. Any of a wide variety of detectable labels may be suitable for this purpose, including, for example, biotin, a fluorescent label, an antibody label, an antibody fragment label, and/or other detectable labels mentioned herein.

Unique Molecular Identifiers

In some embodiments, a nucleic acid template, transposon, and/or primer described herein can include a unique molecular identifiers (abbreviated as "UMIs" herein). UMIs refer to sequences that can be used to retrieve information about a nucleic acid template, a, or a portion thereof. For example, in methods of the disclosure involving multiple primers, each UMI may be associated with a particular primer, e.g., a primer that binds to a specific target sequence. In some embodiments, UMIs are referred to as UMI barcodes.

In some embodiments, detection of the detection sequence can be used to identify a particular UMI and, e.g., to identify the target, transposon, or primer associated with the particular UMI.

In some embodiments, the UMI is a randomly generated sequence. In some embodiments, the UMI is between eight and 20 nucleotides in length, for example, between 10 and 16 nucleotides in length, such as 10, 11, 12, 13, 14, 15, and 16 nucleotides in length. The production and use of UMIs in various contexts are known in the art.

Nucleases

Methods of the present disclosure are suitable for assessing the cleavage profiles of a variety of nucleases, including both well-known nucleases and less characterized nucleases. Generally, the nuclease is site-specific in that it is known or expected to cleave only at a specific sequence or set of sequences, referred to herein as the nuclease's "target site".

In methods presently disclosed herein, incubation step(s) with the nuclease are generally carried under out under conditions favorable for the cleavage by the nuclease. That is, even though a given candidate target site or variant target site might not actually be cleaved by the nuclease, the incubation conditions are such that the nuclease would have cleaved at least a significant portion (e.g., at least 10%, at least 20%, at least 30%, at least 40%, at least 50%, at least 60%, at least 70%, at least 80%, at least 90%, or at least 95%) of templates containing its known target site. For known and generally well-characterized nucleases, such conditions are generally known in the art and/or can easily be discovered or optimized. For newly discovered nucleases, such conditions can generally be approximated using information about related nucleases that are better characterized (e.g., homologs and orthologs).

In some embodiments, the nuclease is an endonuclease. In some embodiments, the nuclease is a site-specific endonuclease (e.g., a restriction endonuclease, a meganuclease, a transcription activator-like effector nucleases (TALEN), a zinc finger nuclease, etc.).

In some embodiments, the site specificity of a site-specific nuclease is conferred by an accessory molecule. For example, the CRISPR-associated (Cas) nucleases are guided to specific sites by "guide RNAs" or gRNAs as described herein. In some embodiments, the nuclease is an RNA-guided nuclease. In some embodiments, the nuclease is a CRISPR-associated nuclease.

In some embodiments, the nuclease is a homolog or an ortholog of a previously known nuclease, for example, a newly discovered homolog or ortholog.

RNA-Guided Nucleases

RNA-guided nucleases according to the present disclosure include, but are not limited to, naturally-occurring Class 2 CRISPR nucleases such as Cas9, and Cpf1, as well as other nucleases derived or obtained therefrom. In functional terms, RNA-guided nucleases are defined as those nucleases that: (a) interact with (e.g., complex with) a gRNA; and (b) together with the gRNA, associate with, and optionally cleave or modify, a target region of a DNA that includes (i) a sequence complementary to the targeting domain of the gRNA and, optionally, (ii) an additional sequence referred to as a "protospacer adjacent motif," or "PAM," which is described in greater detail below. As the following examples will illustrate, RNA-guided nucleases can be defined, in broad terms, by their PAM specificity and cleavage activity, even though variations may exist between individual RNA-guided nucleases that share the same PAM specificity or cleavage activity. Skilled artisans will appreciate that some aspects of the present disclosure relate to systems, methods and compositions that can be implemented using any suitable RNA-guided nuclease having a certain PAM specificity and/or cleavage activity. For this reason, unless otherwise specified, the term RNA-guided nuclease should be understood as a generic term, and not limited to any particular type (e.g., Cas9 vs. Cpf1), species (e.g., S. pyogenes vs. S. aureus) or variation (e.g., full-length vs. truncated or split; naturally-occurring PAM specificity vs. engineered PAM specificity, etc.) of RNA-guided nuclease.

The PAM sequence takes its name from its sequential relationship to the "protospacer" sequence that is complementary to gRNA targeting domains (or "spacers"). Together with protospacer sequences, PAM sequences define target regions or sequences for specific RNA-guided nuclease/gRNA combinations.

Various RNA-guided nucleases may require different sequential relationships between PAMs and protospacers. In general, Cas9s recognize PAM sequences that are 3' of the protospacer as visualized relative to the guide RNA targeting domain. Cpf1, on the other hand, generally recognizes PAM sequences that are 5' of the protospacer.

In addition to recognizing specific sequential orientations of PAMs and protospacers, RNA-guided nucleases can also recognize specific PAM sequences. S. aureus Cas9, for instance, recognizes a PAM sequence of NNGRRT or NNGRRV, wherein the N residues are immediately 3' of the region recognized by the gRNA targeting domain. S. pyogenes Cas9 recognizes NGG PAM sequences. And F. novicida Cpf1 recognizes a TTN PAM sequence. PAM sequences have been identified for a variety of RNA-guided nucleases, and a strategy for identifying novel PAM sequences has been described by Shmakov et al., 2015, Molecular Cell 60, 385-397, Nov. 5, 2015. It should also be noted that engineered RNA-guided nucleases can have PAM specificities that differ from the PAM specificities of reference molecules (for instance, in the case of an engineered RNA-guided nuclease, the reference molecule may be the naturally occurring variant from which the RNA-guided nuclease is derived, or the naturally occurring variant having the greatest amino acid sequence homology to the engineered RNA-guided nuclease).

In addition to their PAM specificity, RNA-guided nucleases can be characterized by their DNA cleavage activity: naturally-occurring RNA-guided nucleases typically form DSBs in target nucleic acids, but engineered variants have been produced that generate only SSBs (discussed above) Ran & Hsu, et al., Cell 154(6), 1380-1389, Sep. 12, 2013 ("Ran"), incorporated by reference herein), or that that do not cut at all.

Cas9

Crystal structures have been determined for S. pyogenes Cas9 (Jinek et al., Science 343(6176), 1247997, 2014 ("Jinek 2014"), and for S. aureus Cas9 in complex with a unimolecular guide RNA and a target DNA (Nishimasu 2014; Anders et al., Nature. 2014 Sep. 25; 513(7519):569-73 ("Anders 2014"); and Nishimasu 2015).

A naturally occurring Cas9 protein comprises two lobes: a recognition (REC) lobe and a nuclease (NUC) lobe; each of which comprise particular structural and/or functional domains. The REC lobe comprises an arginine-rich bridge helix (BH) domain, and at least one REC domain (e.g., a REC1 domain and, optionally, a REC2 domain). The REC lobe does not share structural similarity with other known proteins, indicating that it is a unique functional domain. While not wishing to be bound by any theory, mutational analyses suggest specific functional roles for the BH and REC domains: the BH domain appears to play a role in gRNA:DNA recognition, while the REC domain is thought to interact with the repeat:anti-repeat duplex of the gRNA and to mediate the formation of the Cas9/gRNA complex.

The NUC lobe comprises a RuvC domain, an HNH domain, and a PAM-interacting (PI) domain. The RuvC domain shares structural similarity to retroviral integrase superfamily members and cleaves the non-complementary (i.e., bottom) strand of the target nucleic acid. It may be formed from two or more split RuvC motifs (such as RuvC I, RuvCII, and RuvCIII in S. pyogenes and S. aureus). The HNH domain, meanwhile, is structurally similar to HNN endonuclease motifs, and cleaves the complementary (i.e., top) strand of the target nucleic acid. The PI domain, as its name suggests, contributes to PAM specificity.

While certain functions of Cas9 are linked to (but not necessarily fully determined by) the specific domains set forth above, these and other functions may be mediated or influenced by other Cas9 domains, or by multiple domains on either lobe. For instance, in S. pyogenes Cas9, as described in Nishimasu 2014, the repeat:antirepeat duplex of the gRNA falls into a groove between the REC and NUC lobes, and nucleotides in the duplex interact with amino acids in the BH, PI, and REC domains. Some nucleotides in the first stem loop structure also interact with amino acids in multiple domains (PI, BH and REC1), as do some nucleotides in the second and third stem loops (RuvC and PI domains).

CPf1

The crystal structure of Acidaminococcus sp. Cpf1 in complex with crRNA and a double-stranded (ds) DNA target including a TTTN PAM sequence has been solved by Yamano et al. (Cell. 2016 May 5; 165(4): 949-962 ("Yamano"), incorporated by reference herein). Cpf1, like Cas9, has two lobes: a REC (recognition) lobe, and a NUC (nuclease) lobe. The REC lobe includes REC1 and REC2 domains, which lack similarity to any known protein structures. The NUC lobe, meanwhile, includes three RuvC domains (RuvC-I, -II and -III) and a BH domain. However, in contrast to Cas9, the Cpf1 REC lobe lacks an HNH domain, and includes other domains that also lack similarity to known protein structures: a structurally unique PI domain, three Wedge (WED) domains (WED-I, -II and -III), and a nuclease (Nuc) domain.

While Cas9 and Cpf1 share similarities in structure and function, it should be appreciated that certain Cpf1 activities are mediated by structural domains that are not analogous to any Cas9 domains. For instance, cleavage of the complementary strand of the target DNA appears to be mediated by the Nuc domain, which differs sequentially and spatially from the HNH domain of Cas9. Additionally, the non-targeting portion of Cpf1 gRNA (the handle) adopts a pseudoknot structure, rather than a stem loop structure formed by the repeat:antirepeat duplex in Cas9 gRNAs.

Nucleic Acids Encoding RNA-Guided Nucleases

Nucleic acids encoding RNA-guided nucleases, e.g., Cas9, Cpf1 or functional fragments thereof, are provided herein. Exemplary nucleic acids encoding RNA-guided nucleases have been described previously (see, e.g., Cong et al., Science. 2013 Feb. 15; 339(6121):819-23 ("Cong 2013"); Wang et al., PLoS One. 2013 Dec. 31; 8(12):e85650 ("Wang 2013"); Mali 2013; Jinek 2012).

In some cases, a nucleic acid encoding an RNA-guided nuclease can be a synthetic nucleic acid sequence. For example, the synthetic nucleic acid molecule can be chemically modified. In certain embodiments, an mRNA encoding an RNA-guided nuclease will have one or more (e.g., all) of the following properties: it can be capped; polyadenylated; and substituted with 5-methylcytidine and/or pseudouridine.

Synthetic nucleic acid sequences can also be codon optimized, e.g., at least one non-common codon or less-common codon has been replaced by a common codon. For example, the synthetic nucleic acid can direct the synthesis of an optimized messenger mRNA, e.g., optimized for expression in a mammalian expression system, e.g., described herein. Examples of codon optimized Cas9 coding sequences are presented in WO 2016/073990 ("Cotta-Ramusino").

In addition, or alternatively, a nucleic acid encoding an RNA-guided nuclease may comprise a nuclear localization sequence (NLS). Nuclear localization sequences are known in the art.

Guide RNA (gRNA) Molecules

The terms "guide RNA" and "gRNA" refer to any nucleic acid that promotes the specific association (or "targeting") of an RNA-guided nuclease such as a Cas9 or a Cpf1 to a target sequence such as a genomic or episomal sequence in a cell. gRNAs can be unimolecular (comprising a single RNA molecule, and referred to alternatively as chimeric), or modular (comprising more than one, and typically two, separate RNA molecules, such as a crRNA and a tracrRNA, which are usually associated with one another, for instance by duplexing). gRNAs and their component parts are described throughout the literature, for instance in Briner et al. (Molecular Cell 56(2), 333-339, Oct. 23, 2014 ("Briner"), which is incorporated by reference), and in Cotta-Ramusino.

In bacteria and archea, type II CRISPR systems generally comprise an RNA-guided nuclease protein such as Cas9, a CRISPR RNA (crRNA) that includes a 5' region that is complementary to a foreign sequence, and a trans-activating crRNA (tracrRNA) that includes a 5' region that is complementary to, and forms a duplex with, a 3' region of the crRNA. While not intending to be bound by any theory, it is thought that this duplex facilitates the formation of—and is necessary for the activity of—the Cas9/gRNA complex. As type II CRISPR systems were adapted for use in gene editing, it was discovered that the crRNA and tracrRNA could be joined into a single unimolecular or chimeric guide RNA, in one non-limiting example, by means of a four nucleotide (e.g., GAAA) "tetraloop" or "linker" sequence bridging complementary regions of the crRNA (at its 3' end) and the tracrRNA (at its 5' end). (Mali et al. Science. 2013 Feb. 15; 339(6121): 823-826 ("Mali 2013"); Jiang et al. Nat Biotechnol. 2013 March; 31(3): 233-239 ("Jiang"); and Jinek et al., 2012 Science August 17; 337(6096): 816-821 ("Jinek 2012"), all of which are incorporated by reference herein.)

Guide RNAs, whether unimolecular or modular, include a "targeting domain" that is fully or partially complementary to a target domain within a target sequence, such as a DNA sequence in the genome of a cell where editing is desired. Targeting domains are referred to by various names in the literature, including without limitation "guide sequences" (Hsu et al., Nat Biotechnol. 2013 September; 31(9): 827-832, ("Hsu"), incorporated by reference herein), "complementarity regions" (Cotta-Ramusino), "spacers" (Briner) and generically as "crRNAs" (Jiang). Irrespective of the names they are given, targeting domains are typically 10-30 nucleotides in length, and in certain embodiments are 16-24 nucleotides in length (for instance, 16, 17, 18, 19, 20, 21, 22, 23 or 24 nucleotides in length), and are at or near the 5' terminus of in the case of a Cas9 gRNA, and at or near the 3' terminus in the case of a Cpf1 gRNA.

In addition to the targeting domains, gRNAs typically (but not necessarily, as discussed below) include a plurality of domains that may influence the formation or activity of gRNA/Cas9 complexes. For instance, as mentioned above, the duplexed structure formed by first and secondary complementarity domains of a gRNA (also referred to as a repeat:anti-repeat duplex) interacts with the recognition (REC) lobe of Cas9 and can mediate the formation of Cas9/gRNA complexes. (Nishimasu et al., Cell 156, 935-949, Feb. 27, 2014 ("Nishimasu 2014") and Nishimasu et al., Cell 162, 1113-1126, Aug. 27, 2015 ("Nishimasu 2015"), both incorporated by reference herein). It should be noted that the first and/or second complementarity domains may contain one or more poly-A tracts, which can be recognized by RNA polymerases as a termination signal. The sequence of the first and second complementarity domains are, therefore, optionally modified to eliminate these tracts and promote the complete in vitro transcription of gRNAs, for instance through the use of A-G swaps as described in Briner, or A-U swaps. These and other similar modifications to the first and second complementarity domains are within the scope of the present disclosure.

Along with the first and second complementarity domains, Cas9 gRNAs typically include two or more additional duplexed regions that are involved in nuclease activity in vivo but not necessarily in vitro. (Nishimasu 2015). A first stem-loop one near the 3' portion of the second complementarity domain is referred to variously as the "proximal domain," (Cotta-Ramusino) "stem loop 1" (Nishimasu 2014 and 2015) and the "nexus" (Briner). One or more additional stem loop structures are generally present near the 3' end of the gRNA, with the number varying by species: S. pyogenes gRNAs typically include two 3' stem loops (for a total of four stem loop structures including the repeat:anti-repeat duplex), while S. aureus and other species have only one (for a total of three stem loop structures). A description of conserved stem loop structures (and gRNA structures more generally) organized by species is provided in Briner.

While the foregoing description has focused on gRNAs for use with Cas9, it should be appreciated that other RNA-guided nucleases have been (or may in the future be) discovered or invented which utilize gRNAs that differ in some ways from those described to this point. For instance, Cpf1 ("CRISPR from Prevotella and Franciscella 1") is a recently discovered RNA-guided nuclease that does not require a tracrRNA to function. (Zetsche et al., 2015, Cell 163, 759-771 Oct. 22, 2015 ("Zetsche I"), incorporated by reference herein). A gRNA for use in a Cpf1 genome editing system generally includes a targeting domain and a complementarity domain (alternately referred to as a "handle"). It should also be noted that, in gRNAs for use with Cpf1, the targeting domain is usually present at or near the 3' end, rather than the 5' end as described above in connection with Cas9 gRNAs (the handle is at or near the 5' end of a Cpf1 gRNA).

Those of skill in the art will appreciate, however, that although structural differences may exist between gRNAs from different prokaryotic species, or between Cpf1 and Cas9 gRNAs, the principles by which gRNAs operate are generally consistent. Because of this consistency of operation, gRNAs can be defined, in broad terms, by their targeting domain sequences, and skilled artisans will appreciate that a given targeting domain sequence can be incorporated in any suitable gRNA, including a unimolecular or chimeric gRNA, or a gRNA that includes one or more chemical modifications and/or sequential modifications (substitutions, additional nucleotides, truncations, etc.). Thus, for economy of presentation in this disclosure, gRNAs may be described solely in terms of their targeting domain sequences.

More generally, skilled artisans will appreciate that some aspects of the present disclosure relate to systems, methods and compositions that can be implemented using multiple RNA-guided nucleases. For this reason, unless otherwise specified, the term gRNA should be understood to encompass any suitable gRNA that can be used with any RNA-guided nuclease, and not only those gRNAs that are compatible with a particular species of Cas9 or Cpf1. By way of illustration, the term gRNA can, in certain embodiments, include a gRNA for use with any RNA-guided nuclease occurring in a Class 2 CRISPR system, such as a type II or type V or CRISPR system, or an RNA-guided nuclease derived or adapted therefrom.

Ligating

Some embodiments of presently disclosed methods comprise a step of ligating nucleic acid sequences, e.g., cleaved ends of a nucleic acid template with an oligonucleotide capture probe or a mixture thereof. In some embodiments, the step of ligating is accomplished using a ligase enzyme that acts on nucleic acids, e.g., a DNA and/or RNA ligase. A variety of such ligases are known in the art, many of which are commercially available.

Examples of ligases that may be used in various embodiments of the presently disclosed methods include, but are not limited to, T4 DNA ligase, T3 DNA ligase, T7 DNA ligase, and *E. coli* ligase.

The type of ligase chosen may depend on the type of cleaved ends present in the cleavage composition and/or the capture end of oligonucleotide capture probe.

For example, if the cleaved ends in the cleavage composition comprise blunt ends, or comprise cleaved ends that are blunted before ligation (e.g., during an additional step of blunting, as described herein), a ligase suitable for ligating blunt ends may be chosen.

For example, if the cleaved ends in the cleavage composition comprise overhangs ("cohesive ends") that will not be blunted before ligation (e.g., during an additional step of blunting, as described herein), a ligase suitable for ligating sticky ends may be chosen.

Some ligases work well for both blunt ends and ends with overhangs, and any of these ligases may be used in methods of the present disclosure. Furthermore, any combination of two or more ligases may also be used during a ligating step.

Analysis of Ligation Products

In some embodiments, a plurality of ligation products described herein is analyzed. In some embodiments, a plurality of ligation products is amplified. In some embodiments in which the plurality of ligation products comprises one or more detection sequences, amplification primers that recognize one or more of the detection sequences can be used.

In some such embodiments, amplification products are analyzed. For example, in some embodiments, methods further comprise a step of determining the levels of ligation products. The levels that are determined can be absolute and/or relative.

In some embodiments, methods further comprise a step of calculating a relative abundance of a ligation product. The analysis may comprise nucleic acid sequencing of the ligation product and/or amplification product thereof. As a non-limiting example, next generation (also known as high throughput sequencing) can be performed.

In some embodiments, deep sequencing is performed, meaning that each nucleotide is read several times during the sequencing process, for example at a depth of greater than at least 7, at least 10, at least 15, at least 20, or ever greater, wherein depth (D) is calculated as $$D = N \times L / G \quad \text{(Equation 1)},$$

wherein N is the number of reads, L is the length of the original genome, and G is length of the polynucleotide being sequenced.

In some embodiments, Sanger sequencing is used to analyze at least some of the ligation products and/or amplification products thereof.

Figure 12:
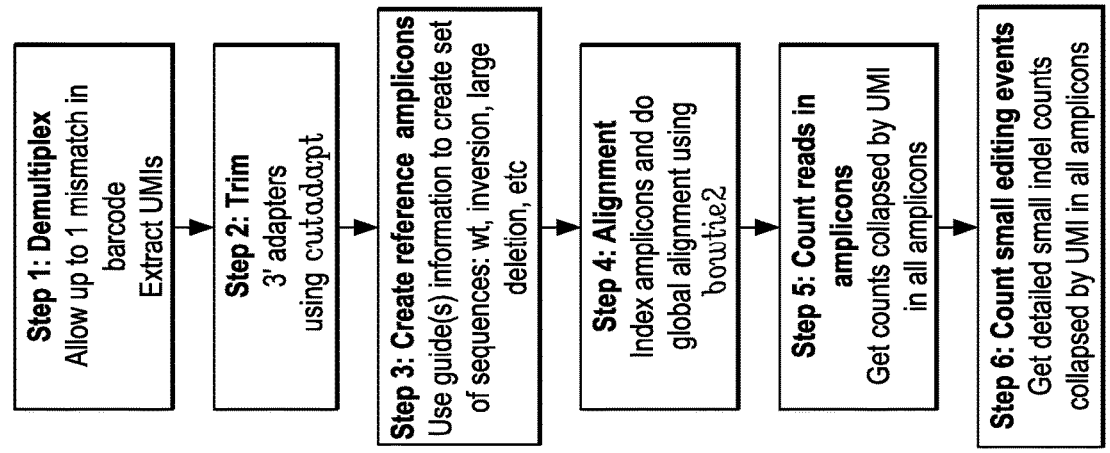
FIG. 12 is a schematic of an exemplary bioinformatics pipeline for certain methods of the disclosure.

In some embodiments, sequencing data is processed using bioinformatics, e.g., one or more steps depicted in FIG. 12. For example, sequencing reads can first be demultiplexed into different experiments in the run using appropriate sequencing barcodes. In some instances, up to 1, 2, or 3 mismatches are allowed in each barcode. UMIs for each read can then be extracted for further downstream analysis. In some methods, adapters (e.g., 3' adapters) can then be trimmed from sequencing reads using known methods, such as cutadapt (as described in, e.g., Martin, EMBnet.journal 17:10-12 (2011)). In some instances, one or more reference amplicons are created. For example, expected cut sites can be used to build reference amplicons with the expected chromosomal rearrangements (e.g., wild type, large deletion, inversion, translocation, etc.). A reference amplicon may comprise any predicted gene editing events as well as "off-target" events. In some embodiments, reference amplicons may include vector or plasmid sequence. Reference amplicons which include sequence from vectors or plasmids may also comprise any predicted gene editing events and/or any "off-target" events.

In some methods, paired reads can then be globally aligned to all or nearly all the reference amplicons using, e.g., a sequence aligner. One exemplary sequence aligner is bowtie2 (as described in, e.g., Langmead et al., Nat. Methods 9:357-9 (2012)). Additionally or alternatively, sorted bam files can be created and/or indexed using suitable tools, such as SAMtools (as described in, e.g., Li et al., Bioinformatics 25:2078-9 (2009)). In some methods, sequence reads completely covering a window around predicted junctions (e.g., 10, 11, 12, 13, 14, 15, 16, 17, 18, 19, or 20 bp) can be extracted and the total number of unique UMIs counted. In some methods, sequence reads that are unable to be mapped to a reference amplicon can be extracted and mapped globally using, e.g., bowtie2 to an appropriate background reference genome.

At least part of the example process described herein for assessing nuclease cleavage, may be implemented using one or more computer systems comprising hardware or a combination of hardware and software. For example, computer systems may include various controllers and/or processing devices located at various points to control operation of automated elements. A central computer may coordinate operation among the various controllers or processing devices. The central computer, controllers, and processing devices may execute various software routines to implement control and coordination of the various automated elements.

The example process can be implemented, at least in part, using one or more computer program products, e.g., one or more computer program tangibly embodied in one or more information carriers, such as one or more non-transitory machine-readable media, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing all or part of the example process can be performed by one or more programmable processors executing one or more computer programs to perform the functions described herein. All or part of the example process can be implemented using special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks. Machine-readable storage media suitable for embodying computer program instructions and data include all forms of non-volatile storage area, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks.

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

The disclosure is further illustrated by the following examples. The examples are provided for illustrative purposes only. They are not to be construed as limiting the scope or content of the disclosure in any way.

EXAMPLES

Example 1: Analysis of Target Gene Cleavage Using UDiTaS

Figure 4:
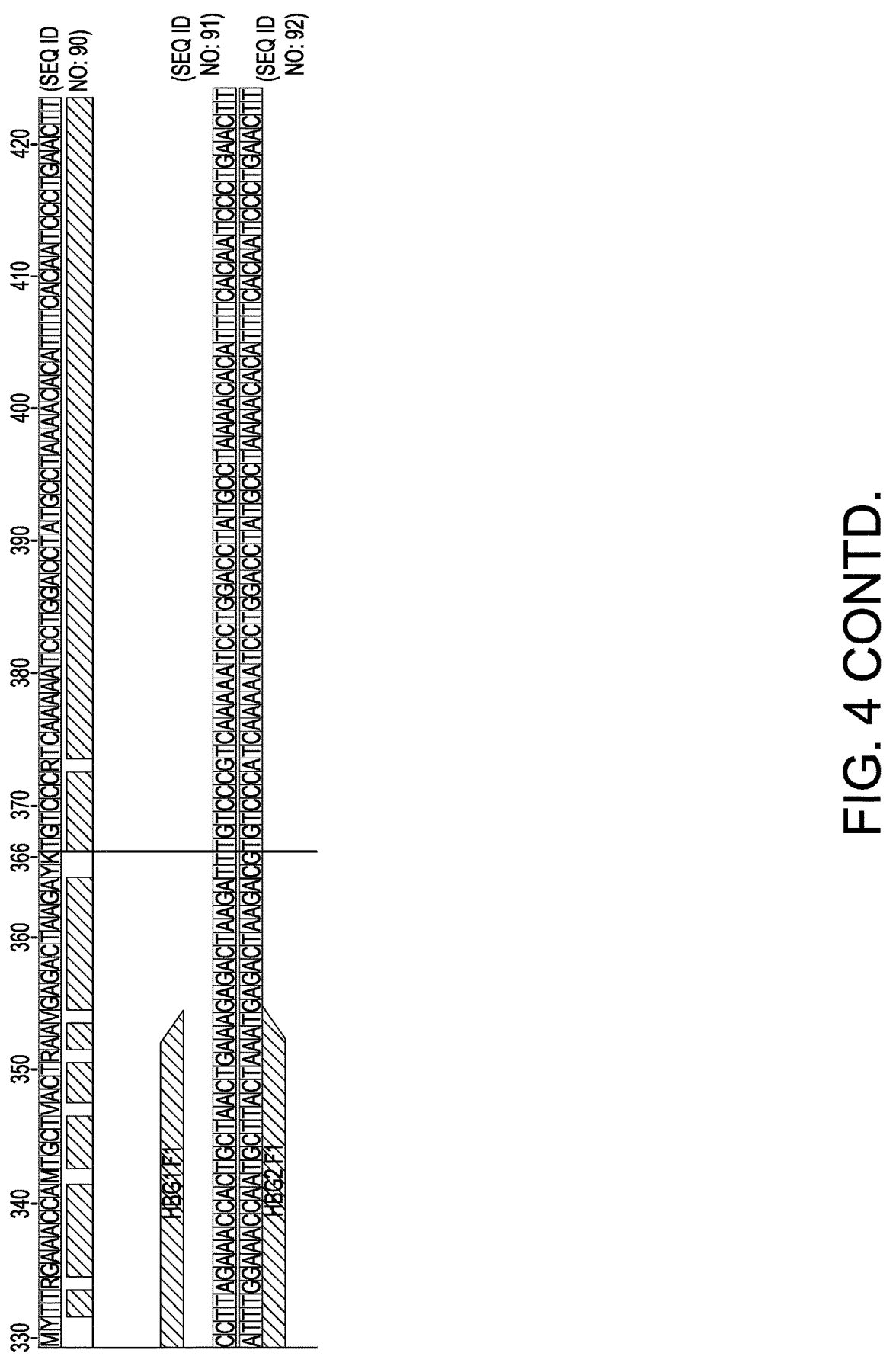

A transposon was used in a method of the disclosure to sequence a genomic DNA sample from K562 cells treated with a site-specific nuclease and various guide RNAs. In a first experiment, a primer pair was used that included (1) a first fixed primer comprising a complementary sequence to a portion of the G1 gene, and (2) a selective primer comprising a nucleotide sequence complementary to the transposon. In a second experiment, a primer pair was used that included (1) a first fixed primer comprising a complementary sequence to a portion of the G2 gene, and (2) a selective primer comprising a nucleotide sequence complementary to the transposon. The primers are depicted in FIG. 4 (fixed primers "G1_F1" and "G2_F1"; selective primers "Seq15_G1_F_UDITASdev" and "Seq16_G2_F_UDITASdev"). DNA fragments were subsequently amplified and sequenced.

Figure 6:
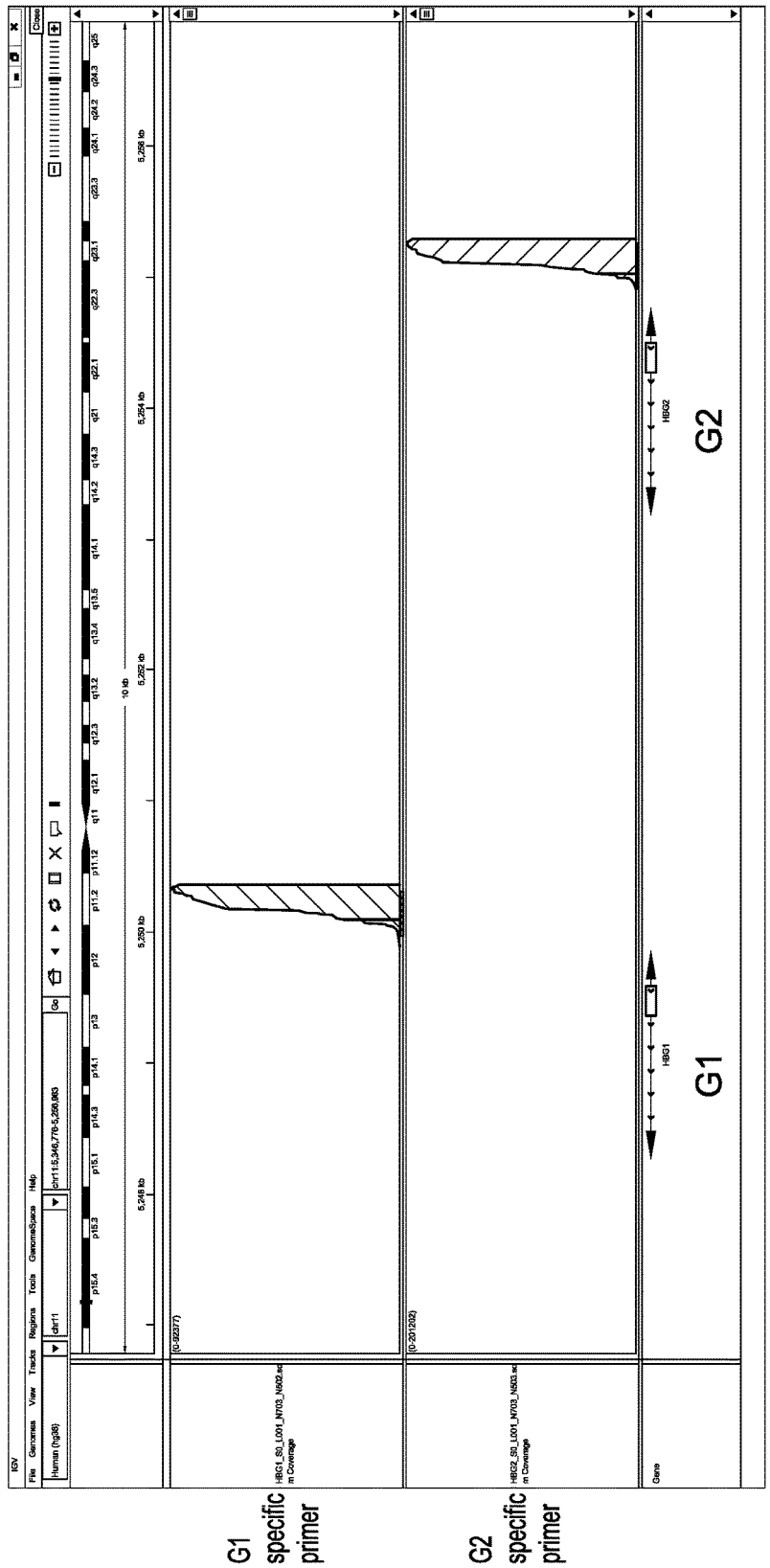
FIG. 6 depicts read coverage plots of G1 and G2 genes using G1 fixed primer and G2 fixed primer in UDiTaS.

FIG. 5 depicts the % sequence reads that were on either G1 or G2 target. As shown in FIG. 5, 78-93% of MiSeq reads correctly sequenced G1 or G2 targets. This demonstrates that a target gene can be successfully sequenced using only one fixed primer specific for the target gene. FIG. 6 depicts the sequence reads in GenomeView.

Example 2: Using UDiTaS to Detect Indels

Figure 7:
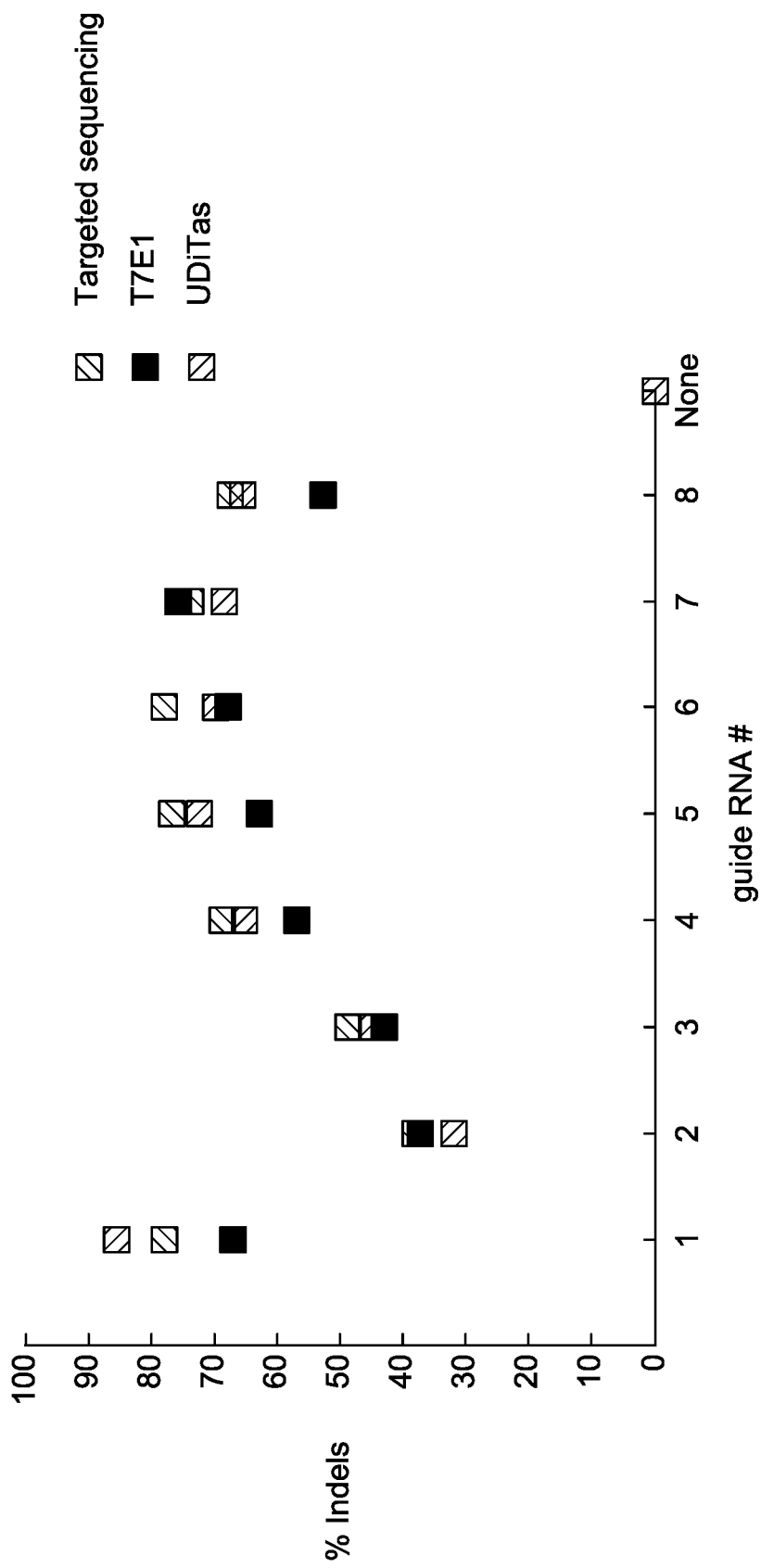
FIG. 7 depicts results of detection of indels using UDiTaS.

The ability of UDiTaS to identify small indel rates for a model genome target was assayed. After contacting the model genome target with a transposon, DNA fragments were amplified using a primer pair included (1) a first fixed primer comprising a complementary sequence to a portion of the model genome target, and (2) a selective primer comprising a nucleotide sequence complementary to the transposon. The UDiTaS method was compared to two known methods—amplicon sequencing and T7E1 sequencing. As shown in FIG. 7, the ability of UDiTaS to detect indels correlated well with targeted sequencing and T7E1 assays.

Example 3: Using UDiTaS to Detect Intra-Chromosomal Rearrangement

Figure 8:
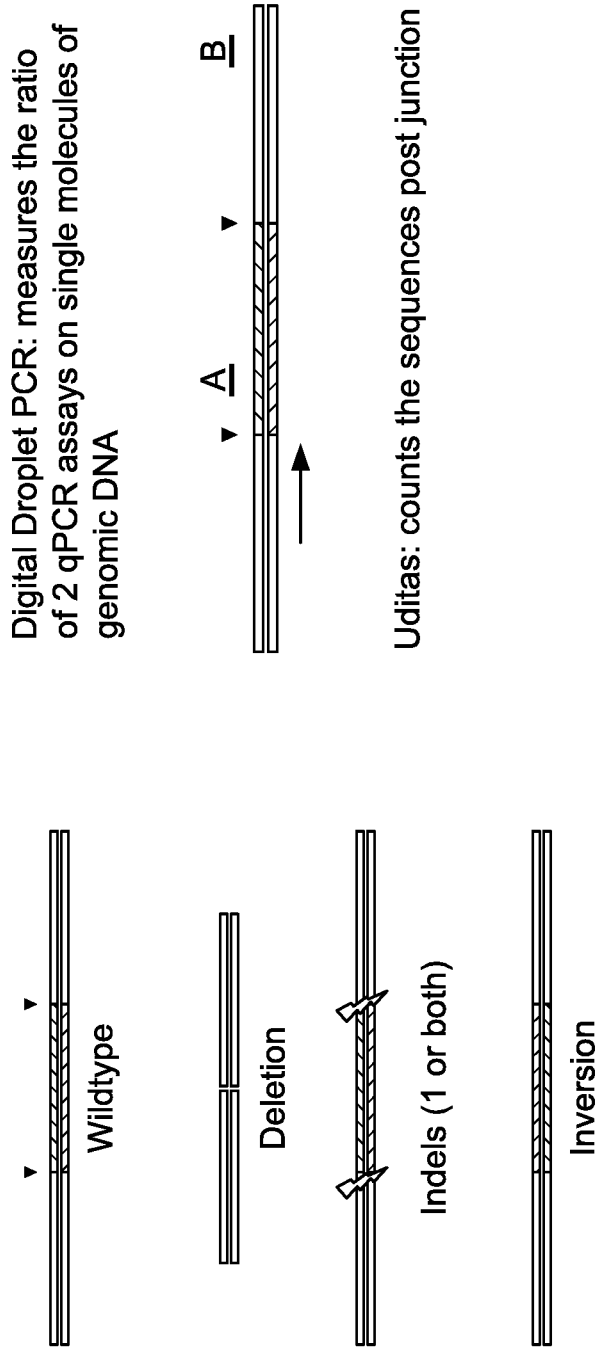
FIG. 8 is a schematic of possible intra-chromosomal rearrangements by dual guide edits.

Treating genomic DNA with a site-specific nuclease and dual guides can have multiple possible outcomes. As shown in FIG. 8, dual guides can result in deletions, indels in one or both strands, and inversions. To determine whether a UDiTaS method can be used to detect such intra-chromosomal rearrangements, genomic DNA from wild type HEK293T cells or from a stable HEK293T clone were used. The genomic DNA of the stable clone includes a deletion in 66% of its genomic DNA and an inversion in 33% of its genomic DNA (see FIG. 9, left side). The genomic DNA from the wild type and the clone were mixed in various ratios and subjected to sequencing by UDiTaS as described herein. The sequencing results were compared to ddPCR sequencing.

Figure 9:
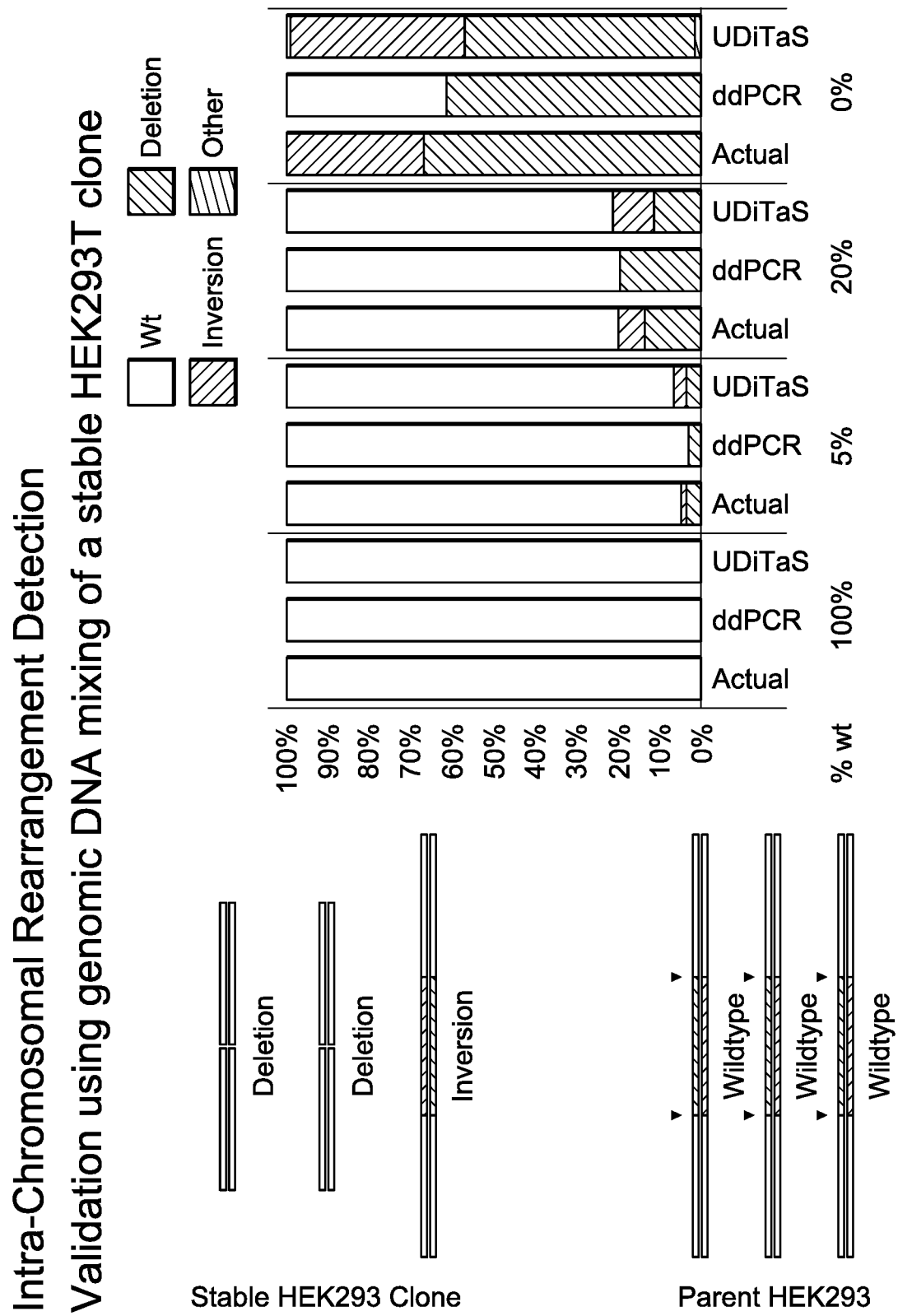
FIG. 9 depicts validation of detection of intra-chromosomal rearrangements using genomic DNA mixing of a stable HEK293T clone.

As shown in FIG. 9 (right side), as the % of wild type genomic DNA in the mixture was reduced from 100% to 0%, UDiTaS was able to detect the reduced frequencies of wild type genomic DNA and increased frequencies of genomic DNA having deletions and inversions in the mixture. In contrast, while ddPCR detected wild type and genomic DNA having deletions, this method was unable to detect genomic DNA having inversions.

Figure 10:
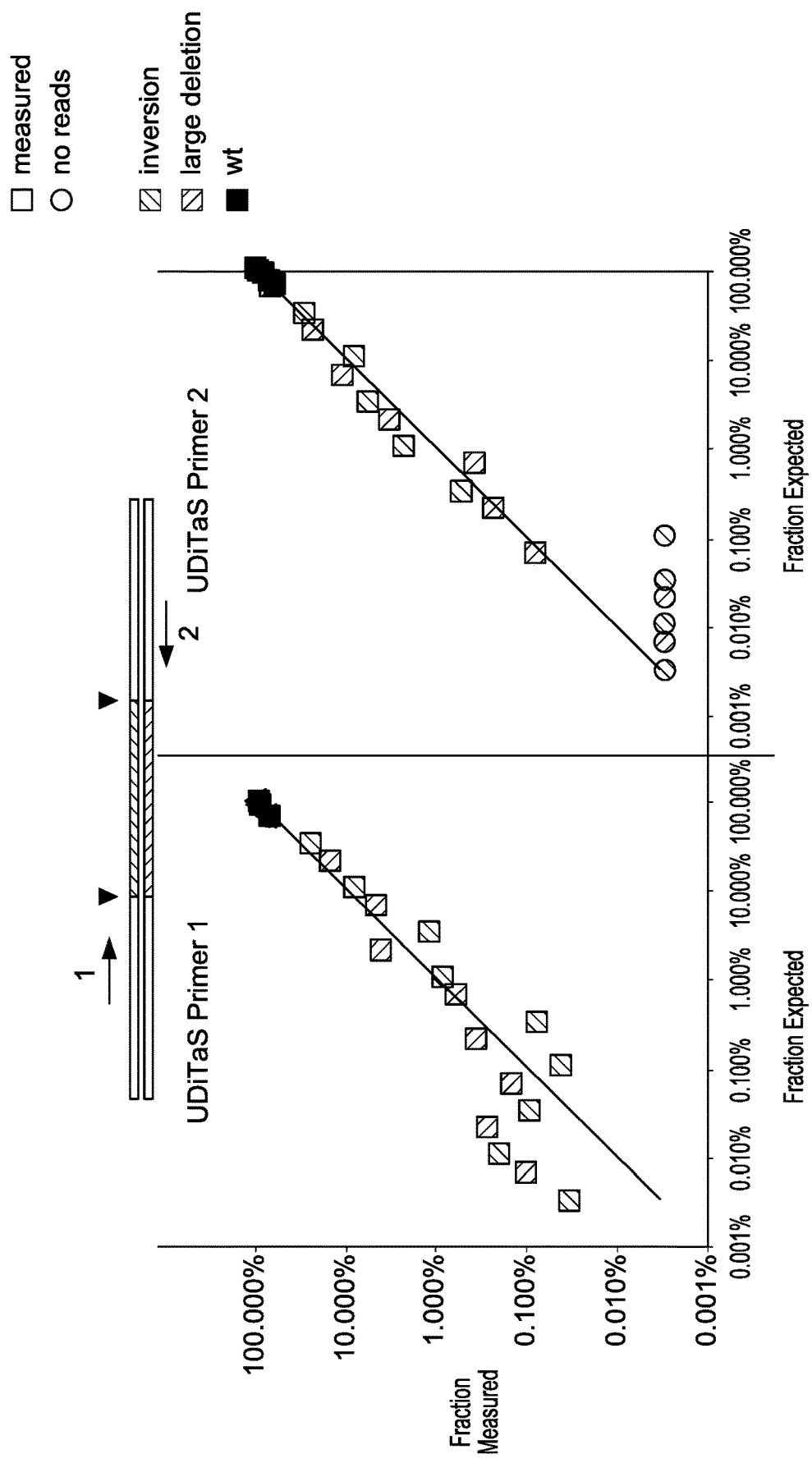
FIG. 10 depicts additional validation of detection of intra-chromosomal rearrangements using genomic DNA mixing.
Figure 11:
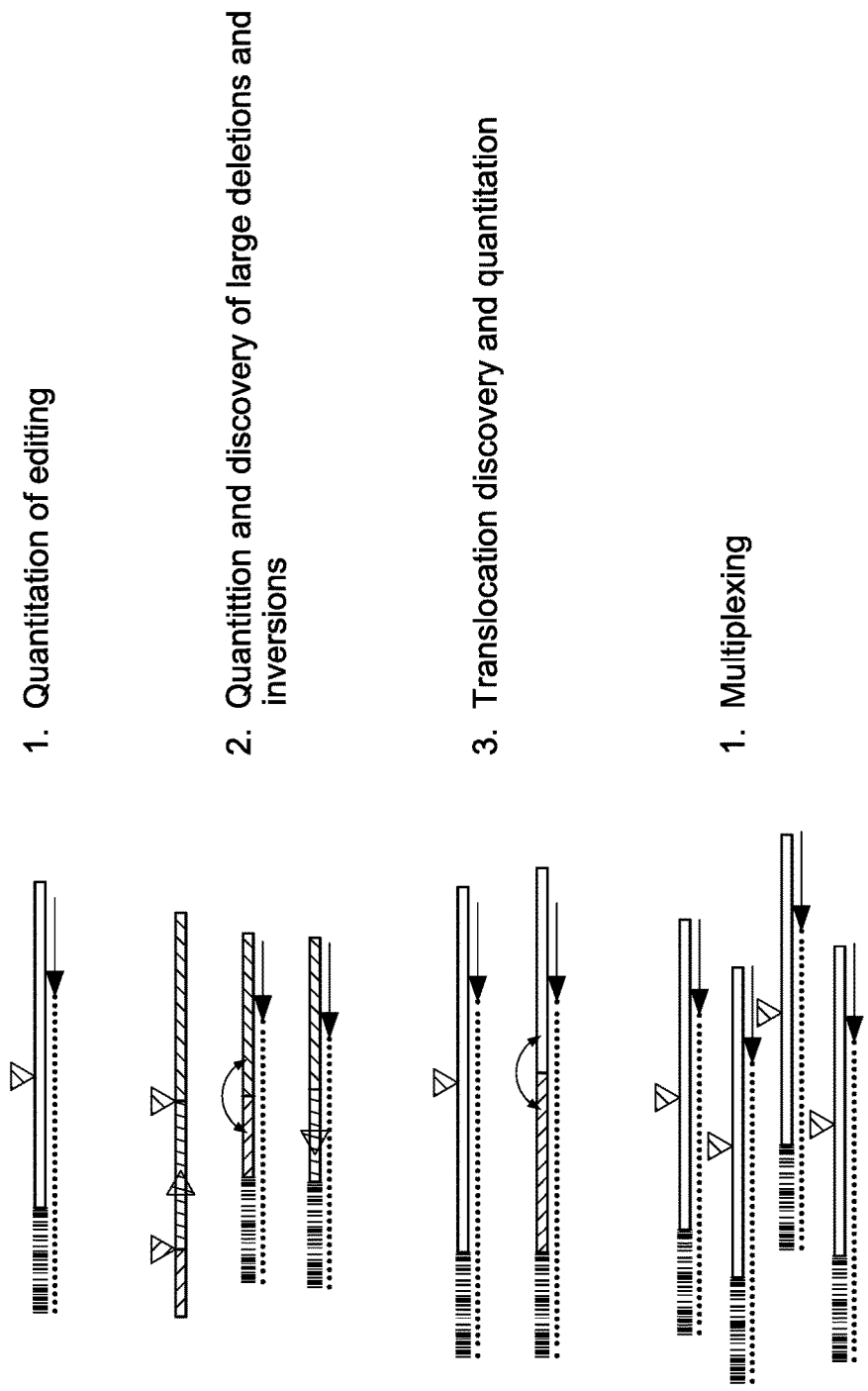
FIG. 11 is a schematic of exemplary methods of the disclosure.

The ability of UDiTaS to detect intra-chromosomal rearrangements was also assessed using genomic DNA samples that included various fractions of wild type genomic DNA, genomic DNA that included an inversion, and genomic DNA that included a large deletion, using two different primers (see FIG. 10). As shown in FIG. 10, UDiTaS was able to accurately determine percentages of particular types of rearrangements in samples having 1) as low as 0.1% large deletions or 2) substantially less than 1% inversions. (See right side of FIG. 10). Using a different primer, UDiTaS was able to detect even lower levels of inversions and deletions, though with less accuracy for lower levels of the relevant alleles. (See left side of FIG. 10.)

Example 4: Bioinformatics Pipeline

In one exemplary method, sequencing data was processed using a bioinformatics pipeline. The analysis pipeline was built using python code that called additional software for specialized steps. The bioinformatics pipeline is schematically depicted in FIG. 12 and consisted of the following steps.

Demultiplexing

Sequencing reads were first demultiplexed into the different experiments in the run using the appropriate sequencing barcodes, allowing up to one mismatch in each barcode. UMIs for each read were extracted for further downstream analysis.

Trimming

3' adapters were trimmed using cutadapt (Martin, EMBnet.journal 17:10-12 (2011)), version 1.9.1.

Creating Reference Amplicons

The expected cut sites were used to build reference amplicons with the expected chromosomal rearrangements: wild type, large deletion, duplication, inversion, translocation, small indel, etc. A reference amplicon may comprise any predicted gene editing events, e.g., "off-target" events. In some embodiments, reference amplicons may include vector or plasmid sequence. Reference amplicons which include sequence from vectors or plasmids may also comprise one or more predicted gene editing events, e.g., "off-target" events.

Alignment

Paired reads were then globally aligned to all the reference amplicons using bowtie2 (Langmead et al., Nat. Methods 9:357-9 (2012)), version 2.1.0. Finally, SAMtools (Li et al., Bioinformatics 25:2078-9 (2009)), version 1.3-5-g664cc5f, was used to create and index sorted bam files.

Alignment Analysis

Reads completely covering a window around the predicted junctions (15 bp) were extracted and the total number of unique UMIs counted.

Final Genome Wide Analysis

Finally, reads that could not be mapped to the reference amplicons were extracted and mapped globally using bowtie2 to the appropriate background reference genome.

Example 5: Analysis of Target Gene Cleavage Using UDiTaS

In one exemplary method, of assessment of complex gene editing events, a pair of *S. aureus* Cas9 (SaCas9) sgRNA were used to target a region within an intron of Gene 3. Reduction of Gene 3 expression leads to several human diseases. Removal of the deleterious intron splice donor site is predicted to restore function of Gene 3. A single guide RNA pair, Gene 3-guide 1 and Gene 3-guide 2, that cuts ~1000 base pairs around the splice donor was selected from an internal screen for characterization.

U-2 OS cells were transfected with linear DNA fragments expressing sgRNA Gene 3-guide 1 and Gene 3-guide 2 along with a plasmid expressing SaCas9. After three days genomic DNA was isolated and UDiTaS sequencing libraries were created. The libraries were sequenced on a MiSeq and the data was processed through a bioinformatics pipeline (FIG. 12).

Figure 13:
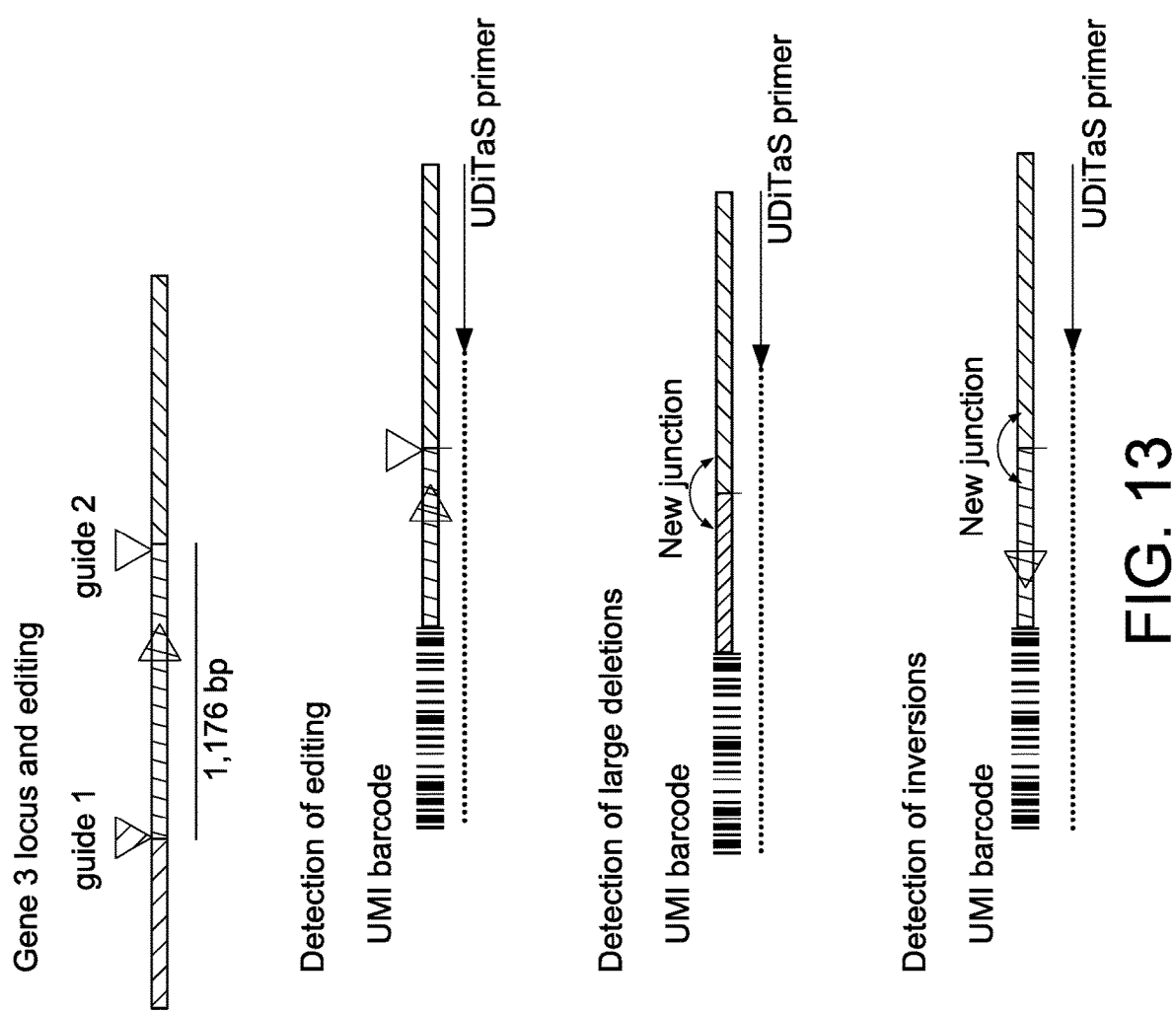
FIG. 13 depicts a schematic showing detection of gene editing events including small indels, large deletions (greater than >100 bp), and inversions.
Figures 14A, 14B:
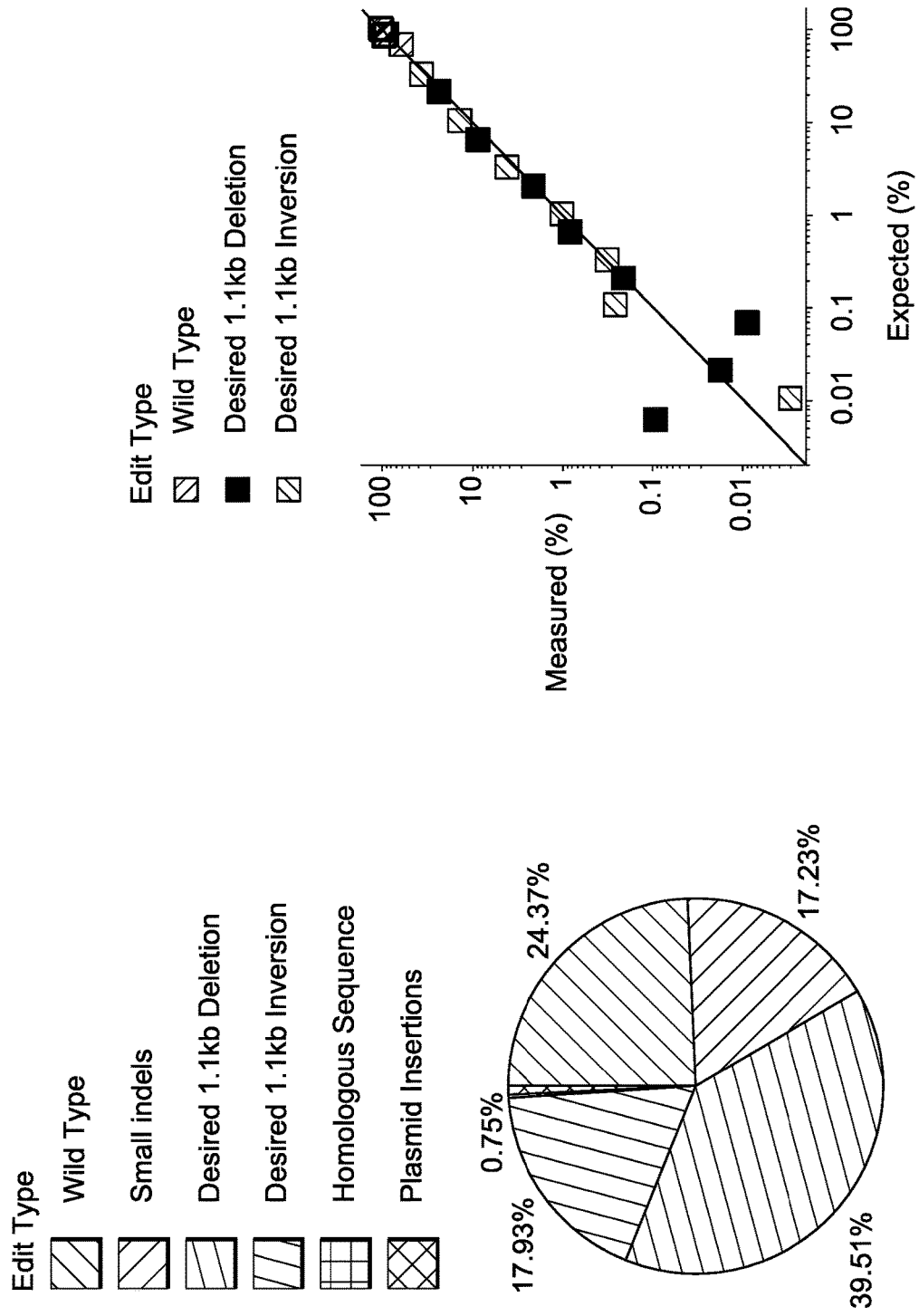
FIG. 14A depicts exemplary edit types following editing of U-2 OS cells at Gene 3 IVS locus with two SaCas9 guides ~1.1 kb apart.
FIG. 14B depicts exemplary linearity and Lower Limit of Detection (LLoD) of a HEK293 cell line, mixed at various ratios with the unmodified parental line.
Figure 15A:
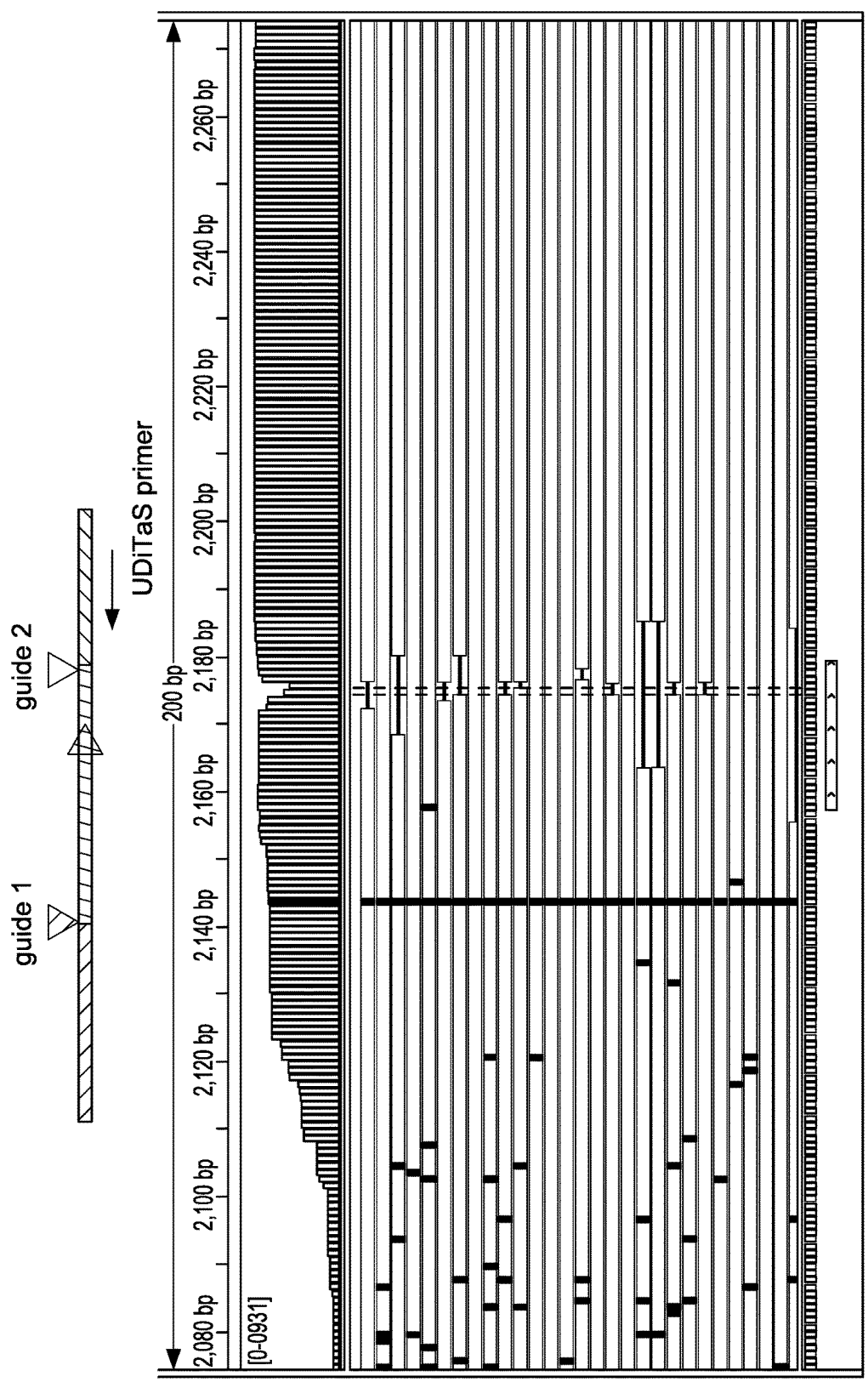
FIGS. 15A-15D depict exemplary editing events in U-2 OS editing studies as shown in an Integrated Genome Viewer (IGV) (Thorvaldsdottir et al. Brief. Bioinform. 2013; 14:178-192; Robinson et al. Nat. Biotechnol. 2011; 29:24-26). A schematic at the top of each view depicts an observed editing event. Reads colored in red/blue were aligned to the top/bottom genomic reference DNA sequence.
Figure 15B:
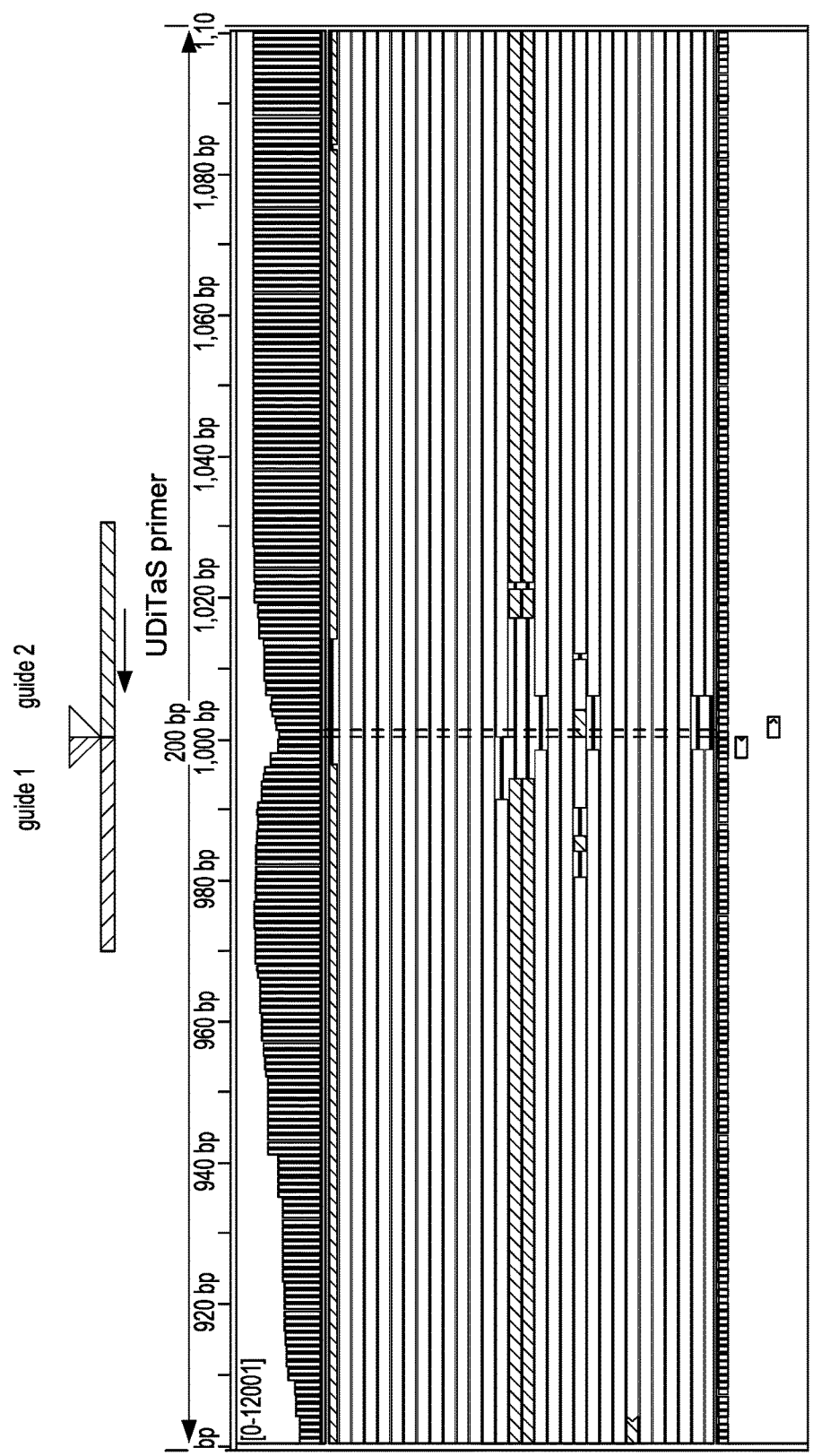
Figure 15C:
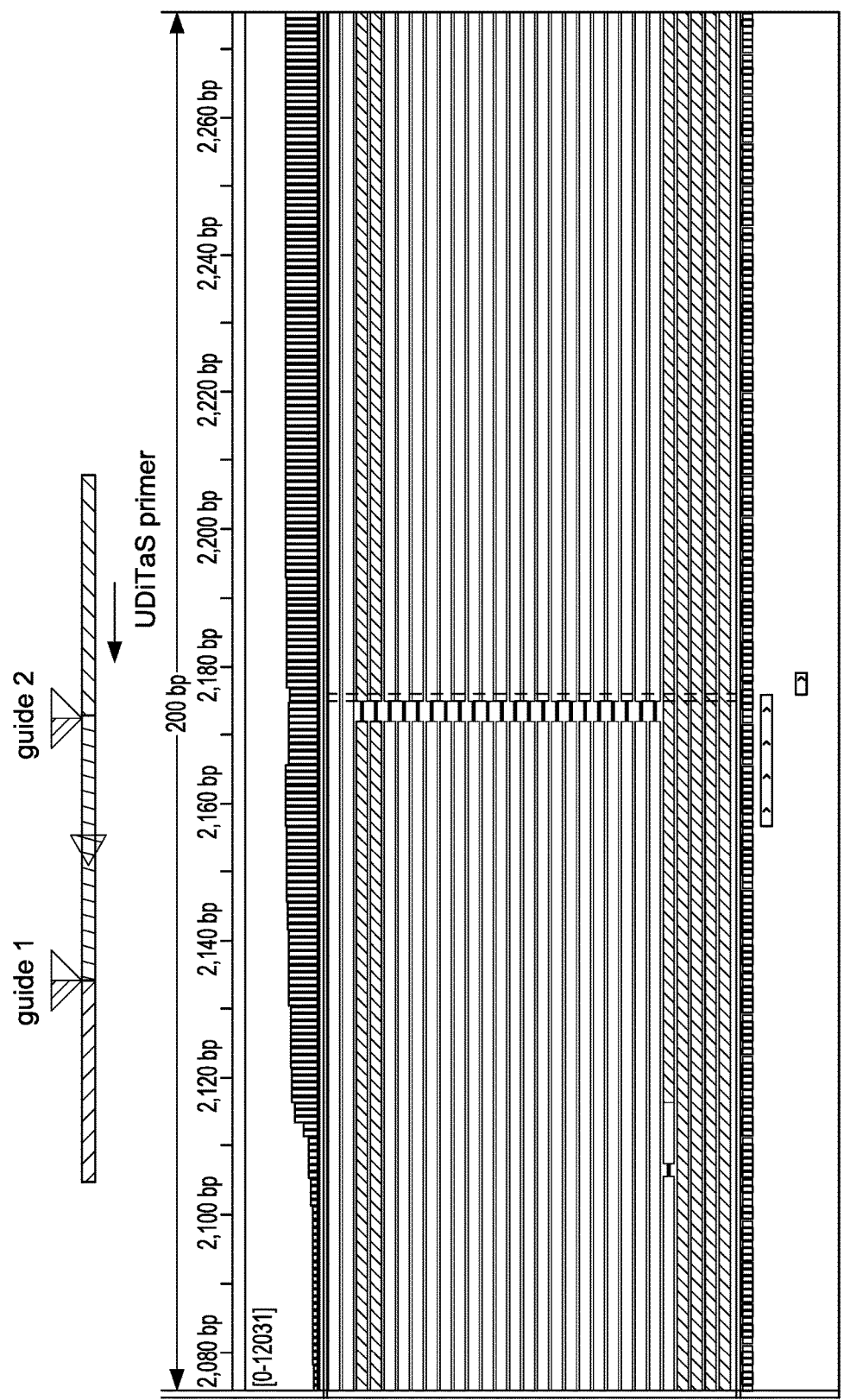
Figure 15D:
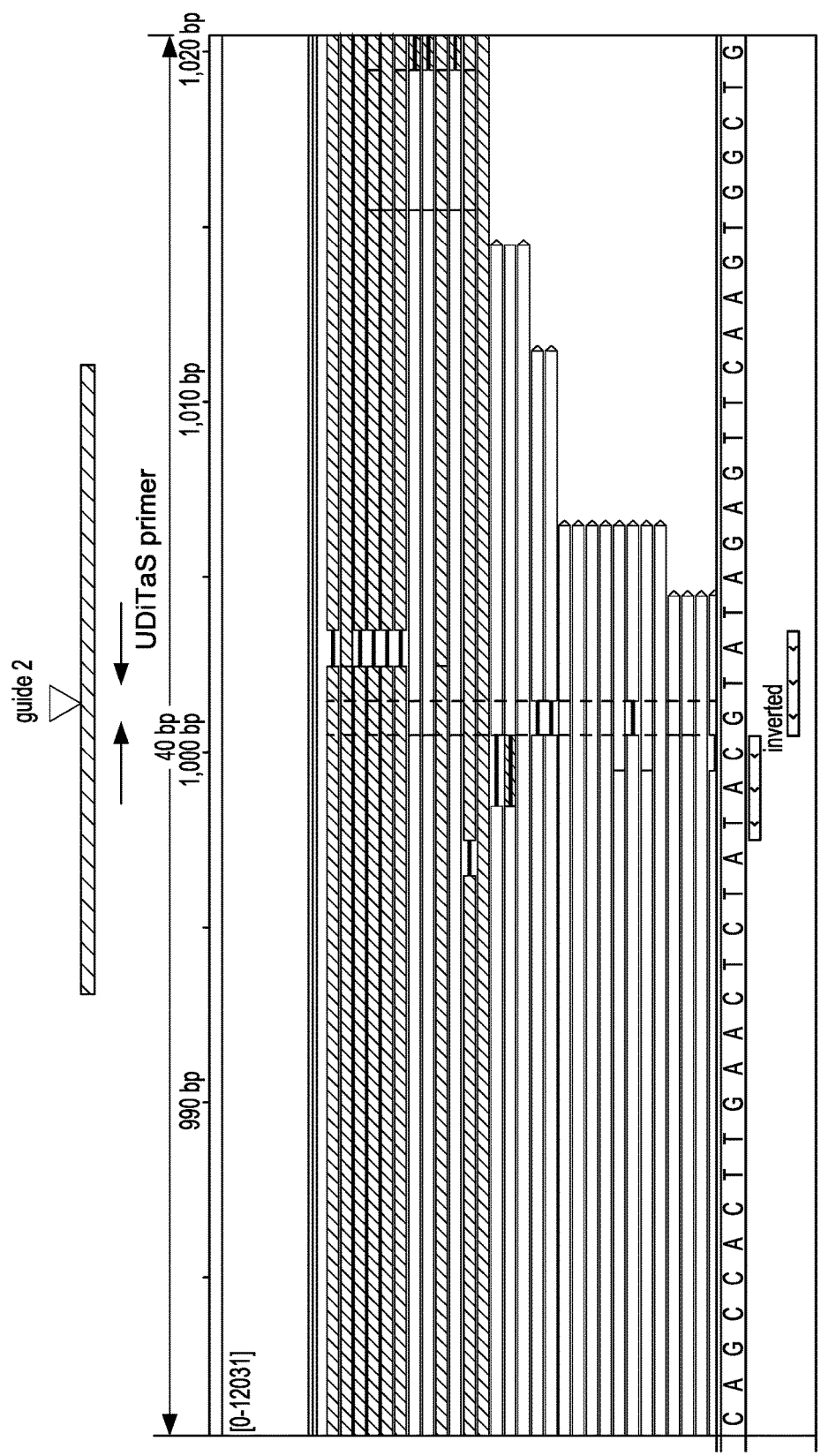

Using a targeted primer flanking the Gene 3-guide 2 cut site (FIG. 13), a range of edits and rearrangements around the expected cut sites were observed (FIGS. 15A-15D), automatically classified, and tallied (FIG. 14A). Editing that resulted in small indel events was observed, as expected, at a rate of ~17%. The indels likely arose due to repair pathway activity prior to rearrangement. In addition, junctions from the desired ~1.1 kb deletion were also present at ~40%. Notably, inversion of the ~1.1 kb fragment between the two cut sites was also observed at ~18%, comparable to the deletion. Other lower frequency junctions were also observed at ~0.75%, including translocations between homologous or sister chromosomes at the identical cut sites (FIG. 15D).

Linearity, Accuracy and LLoD

Figure 16:
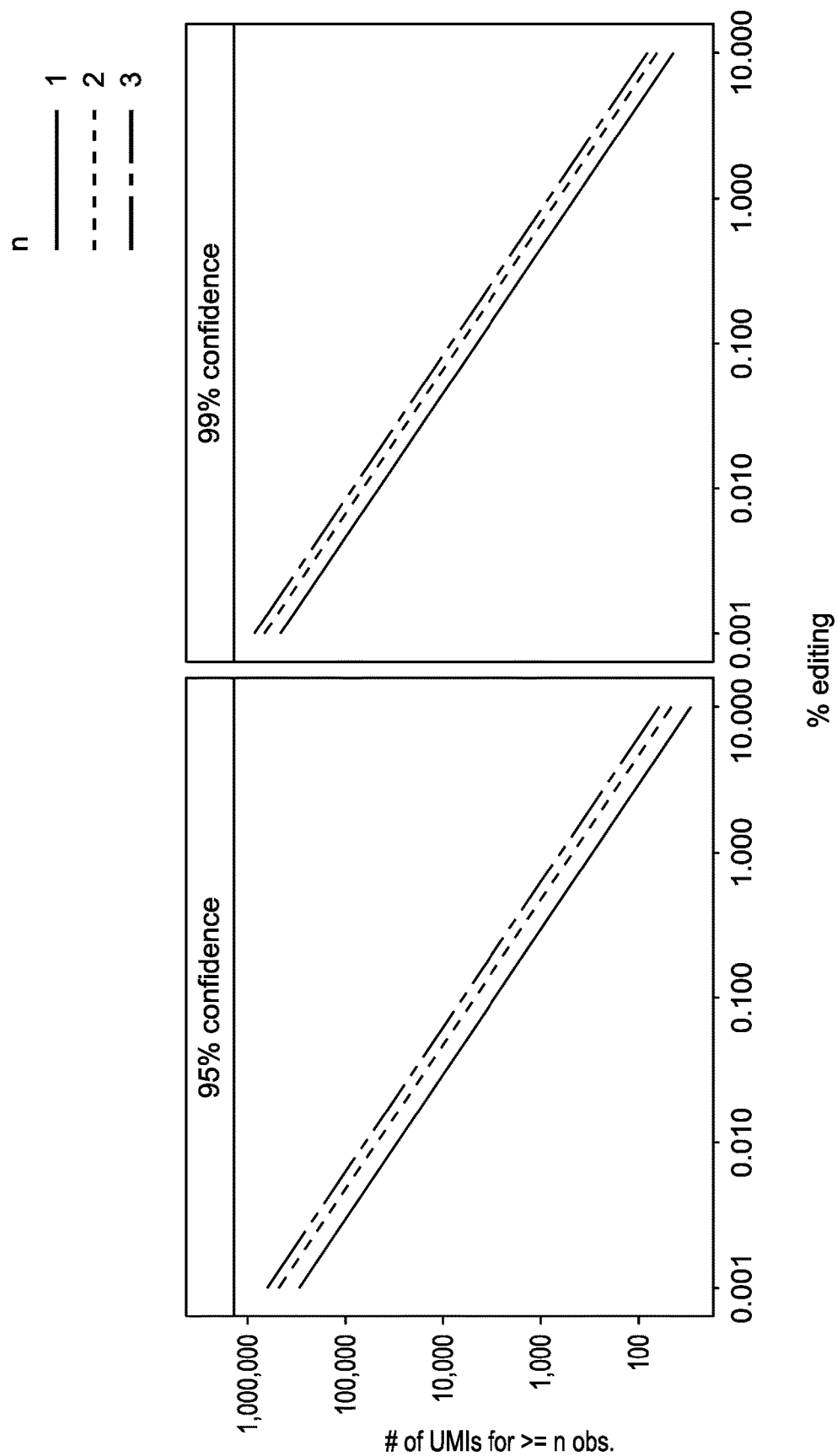
FIG. 16 depicts an exemplary binomial power calculation applied to UDiTaS. A simulated binomial distribution, plotting editing frequency (e.g.: probability of success) vs. number of unique molecular identifiers (e.g.: trials) for a given number of expected observations (1, 2, or 3). Graph on the left shows 95% confidence and graph on the right shows 99% confidence.
Figure 17:
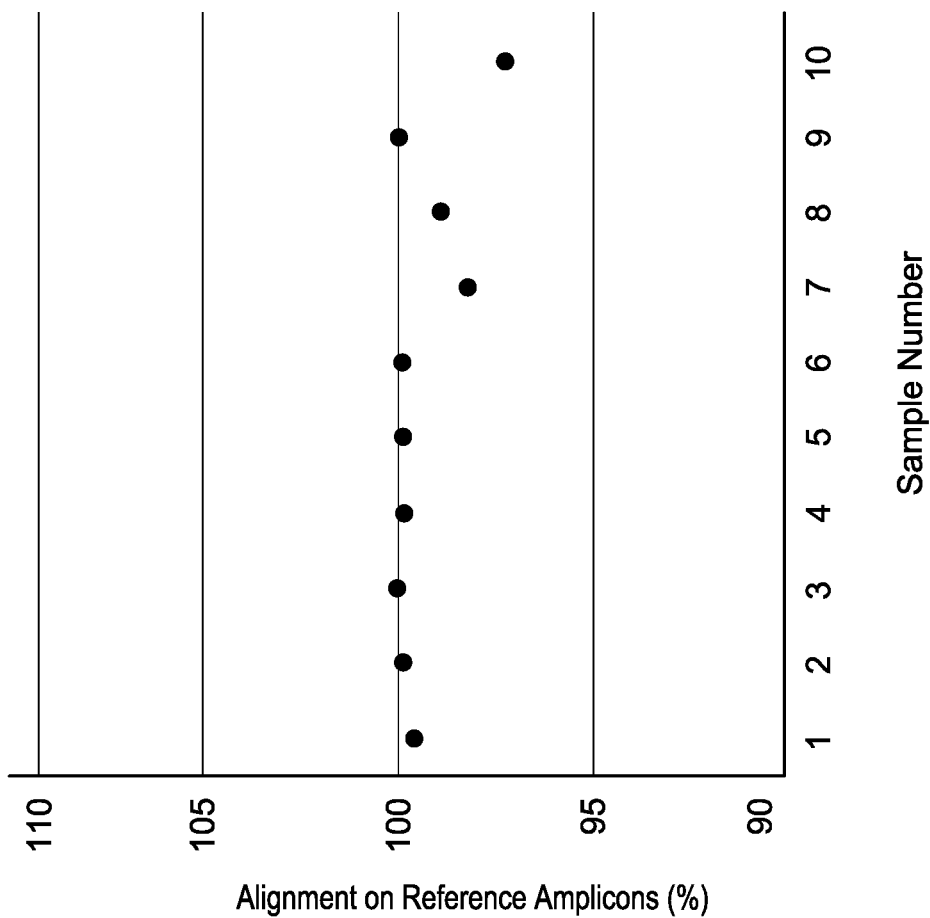
FIG. 17 depicts exemplary genome mapping rates for UDiTaS. Ten distinct samples analyzed using a gene specific primer for Gene 3 guide 2 (OLI6062) were plotted on the x axis. The y axis shows the percentage or reads that mapped to the expected reference amplicon for each sample.

To characterize the method's linearity, accuracy, and Lower Level of Detection (LLoD) for the desired large editing events, a stable cell line and plasmids that contained the Gene 3 intron wild type locus, the deletion, and the inversion were constructed. The HEK293 cells had three copies of the Gene 3 locus and the clone had two deletions and one inversion. Genomic DNA (gDNA) from the edited HEK293 cell line was mixed with parental, non-edited genomic DNA to generate a titration of the ~1.1 kb deletion and inversion across a five-log range. Plotting expected versus UDiTaS measured editing rates for the deletion and inversion showed excellent correlation down to approximately 0.1% (FIG. 14B). The UDiTaS protocol used 50 ng of input DNA, which is equivalent to approximately 14,300 human haplomes. Assuming a binomial sampling distribution and ~20% process yield, 2-3 observations at 0.1% were expected (95% confidence) in the UDiTaS library. This was consistent with the observed rate (FIG. 16). Sensitivity was increased by increasing input DNA along and increasing sequencing read depth, as both are needed to increase the number of unique UMIs in the analysis. On-target mapping rates to the genome were >95%, demonstrating that the process was robust and productive (FIG. 17).

To further demonstrate the linearity of UDiTaS and to compare it to AMP-Seq, reference plasmids synthesized to contain the intron wild type locus, large deletion, and inversion, were analyzed.

TABLE 1

| Plasmids used in this example | |
|---|---|
| Plasmid Name | Description |
| PLA380 | IVT PCR template for Gene 1 and Gene 2 Spy guides |
| PLA379 | pUC57_Amp_Gene3_SNPs1 |
| PLA370 | pUC57_Amp_Gene3_large_inversion_SNPs_1 |
| PLA367 | pUC57_Amp_Gene3_large_deletion_SNPs_1 |
| PLA371 | pUC57_Amp_Gene3_large_inversion_SNPs_2 |
| PLA368 | pUC57_Amp_Gene3_large_deletion_SNPs_2 |
| PLA372 | pUC57_Amp_Gene3_large_inversion_SNPs_3 |
| PLA369 | pUC57_Amp_Gene3_large_deletion_SNPs_3 |

TABLE 1-continued

Plasmids used in this example

| Plasmid Name | Description |
|---|---|
| PLA377 | pUC57_Amp_Gene2_SNPs1 |
| PLA378 | pUC57_Amp_Gene1_SNPs1 |
| PLA361 | pUC57_Amp_Gene2_Gene_1_SNPs_1 |
| PLA362 | pUC57_Amp_Gene2_Gene1_SNPs_2 |
| PLA363 | pUC57_Amp_Gene2_Gene1_SNPs_3 |
| PLA364 | pUC57_Amp_Gene2_Gene1_SNPs_4 |
| PLA365 | pUC57_Amp_Gene2_Gene1_SNPs_5 |
| PLA366 | pUC57_Amp_Gene2_Gene1_SNPs_6 |
| PLA13 | pAF003 STITCHR backbone plasmid |

TABLE 2

Oligos used in this example

| Oligo Name | Description | Sequence |
|---|---|---|
| OLI7076 | Forward primer for Gene2 IVT | CACCGCTAGCTAATACGACTCACTATAGGCCACGGAGCGAGACATCTGTTTTAGAGCTAGAAATA (SEQ ID NO: 1) |
| OLI7077 | Forward primer for Gene1 IVT | CACCGCTAGCTAATACGACTCACTATAGCTGGTACACGGCAGGGTCAGTTTTAGAGCTAGAAATA (SEQ ID NO: 2) |
| OLI7078 | Common reverse primer for IVT template | TTTTTTTTTTTTTTTTTTTGCACCGACTCGGTGCCACTTTTTCAAGTTGATA (SEQ ID NO: 3) |
| OLI6062 | UDiTaS and AMP-seq gene specific primer for Gene3 guide 2 | GTGACTGGAGTTCAGACGTGTGCTCTTCCGATCTGGACCATGGATGCACTCTGTAAATTCTCAT (SEQ ID NO: 4) |
| OLI6256 | UDiTaS and AMP-seq gene specific primer for Gene2 | GTGACTGGAGTTCAGACGTGTGCTCTTCCGATCTGCATGCCTTCTTAAACATCACGAGACTCTAA (SEQ ID NO: 5) |
| OLI6259 | UDiTaS and AMP-seq gene specific primer for Gene1 | GTGACTGGAGTTCAGACGTGTGCTCTTCCGATCTGCACTGTTGCTCTTGAAGTCCATAGACCTC (SEQ ID NO: 6) |
| OLI6380 | UDiTaS adapter top oligo i5_N501_UMI_Tn5-A | AATGATACGGCGACCACCGAGATCTACACTAGATCGCNNNNNNNNTCGTCGGCAGCGTCAGATGTGTATAAGAGACAG (SEQ ID NO: 7) |
| OLI6381 | UDiTaS adapter top oligo i5_N502_UMI_Tn5-A | AATGATACGGCGACCACCGAGATCTACACCTCTCTATNNNNNNNNNTCGTCGGCAGCGTCAGATGTGTATAAGAGACAG (SEQ ID NO: 8) |
| OLI6382 | UDiTaS adapter top oligo i5_N503_UMI_Tn5-A | AATGATACGGCGACCACCGAGATCTACACTATCCTCNNNNNNNNNTCGTCGGCAGCGTCAGATGTGTATAAGAGACAG (SEQ ID NO: 9) |
| OLI6383 | UDiTaS adapter top oligo i5_N504_UMI_Tn5-A | AATGATACGGCGACCACCGAGATCTACACAGAGTAGANNNNNNNNNTCGTCGGCAGCGTCAGATGTGTATAAGAGACAG (SEQ ID NO: 10) |
| OLI6384 | UDiTaS adapter top oligo i5_N505_UMI-Tn5-A | AATGATACGGCGACCACCGAGATCTACACGTAAGGAGNNNNNNNNNTCGTCGGCAGCGTCAGATGTGTATAAGAGACAG (SEQ ID NO: 11) |
| OLI6385 | UDiTaS adapter top oligo i5_N506_UMI_Tn5-A | AATGATACGGCGACCACCGAGATCTACACACTGCATANNNNNNNNNTCGTCGGCAGCGTCAGATGTGTATAAGAGACAG (SEQ ID NO: 12) |

TABLE 2-continued

Oligos used in this example

| Oligo Name | Description | Sequence |
| --- | --- | --- |
| OLI6386 | UDiTaS adapter top oligo i5_N507_UMI_Tn5-A | AATGATACGGCGACCACCGAGATCT ACACAAGGAGTANNNNNNNNNNNTC GTCGGCAGCGTCAGATGTGTATAAG AGACAG(SEQ ID NO: 13) |
| OLI6387 | UDiTaS adapter top oligo | AATGATACGGCGACCACCGAGATCT ACACCTAAGCCTNNNNNNNNNNNTCG TCGGCAGCGTCAGATGTGTATAAGA GACAG(SEQ ID NO: 14) |
| Tn5-A bottom | UDiTaS adapter bottom oligo | [Phos]CTGTCTCTTATACA[ddC] (SEQ ID NO: 15) |
| OLI5589 | UDiTaS and AMP-seq round 1 and 2 PCR primer P5/i5 | AATGATACGGCGACCACCGAGATCT ACAC(SEQ ID NO: 16) |
| OLI5639 | UDiTaS and AMP-seq round 2 PCR primer_i7_N701_SBS12 | CAAGCAGAAGACGGCATACGAGAT AGCGGAATGTGACTGGAGTTCAGAC GTGT(SEQ ID NO: 17) |
| OLI5640 | UDiTaS and AMP-seq round 2 PCR primer_i7_N702_SBS12 | CAAGCAGAAGACGGCATACGAGAT GATCATGCGTGACTGGAGTTCAGAC GTGT(SEQ ID NO: 18) |
| OLI5641 | UDiTaS and AMP-seq round 2 PCR primer_i7_N703_SBS12 | CAAGCAGAAGACGGCATACGAGAT AAGACGGAGTGACTGGAGTTCAGAC GTGT(SEQ ID NO: 19) |
| OLI5642 | UDiTaS and AMP-seq round 2 PCR primer_i7_N704_SBS12 | CAAGCAGAAGACGGCATACGAGAT CGAGTCCTGTGACTGGAGTTCAGAC GTGT(SEQ ID NO: 20) |
| OLI5643 | UDiTaS and AMP-seq round 2 PCR primer_i7_N705_SBS12 | CAAGCAGAAGACGGCATACGAGATT CCTCAGGGTGACTGGAGTTCAGACG TGT(SEQ ID NO: 21) |
| OLI5644 | UDiTaS and AMP-seq round 2 PCR primer_i7_N706_SBS12 | CAAGCAGAAGACGGCATACGAGAT GTACGGATGTGACTGGAGTTCAGAC GTGT(SEQ ID NO: 22) |
| OLI5645 | UDiTaS and AMP-seq round 2 PCR primer_i7_N707_SBS12 | CAAGCAGAAGACGGCATACGAGAT CATCTCTCGTGACTGGAGTTCAGAC GTGT(SEQ ID NO: 23) |
| OLI5646 | UDiTaS and AMP-seq round 2 PCR primer_i7_N710_SBS12 | CAAGCAGAAGACGGCATACGAGAT GTCGGAGCGTGACTGGAGTTCAGAC GTGT(SEQ ID NO: 24) |
| OLI5647 | UDiTaS and AMP-seq round 2 PCR primer_i7_N711_SBS12 | CAAGCAGAAGACGGCATACGAGAT ACGGAGAAGTGACTGGAGTTCAGAC GTGT(SEQ ID NO: 25) |
| OLI5648 | UDiTaS and AMP-seq round 2 PCR primer_i7_N712_SBS12 | CAAGCAGAAGACGGCATACGAGAT AGGAGATGGTGACTGGAGTTCAGAC GTGT(SEQ ID NO: 26) |
| OLI5649 | UDiTaS and AMP-seq round 2 PCR primer_i7_N714_SBS12 | CAAGCAGAAGACGGCATACGAGAT AGTACTCGGTGACTGGAGTTCAGAC GTGT(SEQ ID NO: 27) |
| OLI5650 | UDiTaS and AMP-seq round 2 PCR primer_i7_N715_SBS12 | CAAGCAGAAGACGGCATACGAGAT GGACTCTAGTGACTGGAGTTCAGAC GTGT(SEQ ID NO: 28) |
| OLI2909 | Index 1-AMP-seq top adapter | AATGATACGGCGACCACCGAGATCT ACACACTGCATANNWNNWNNACAC TCTTTCCCTACACGACGCTCTTCCGA TC*T(SEQ ID NO: 29) |
| OLI2910 | Index 1-AMP-seq top adapter | AATGATACGGCGACCACCGAGATCT ACACAAGGAGTANNWNNWNNACAC TCTTTCCCTACACGACGCTCTTCCGA TC*T(SEQ ID NO: 30) |

TABLE 2-continued

Oligos used in this example

| Oligo Name | Description | Sequence |
|---|---|---|
| AMP-seq bottom adapter | AMP-seq bottom adapter | [Phos]GATCGGAAGAGC*C*A (SEQ ID NO: 31) |

Figures 18A, 18B:
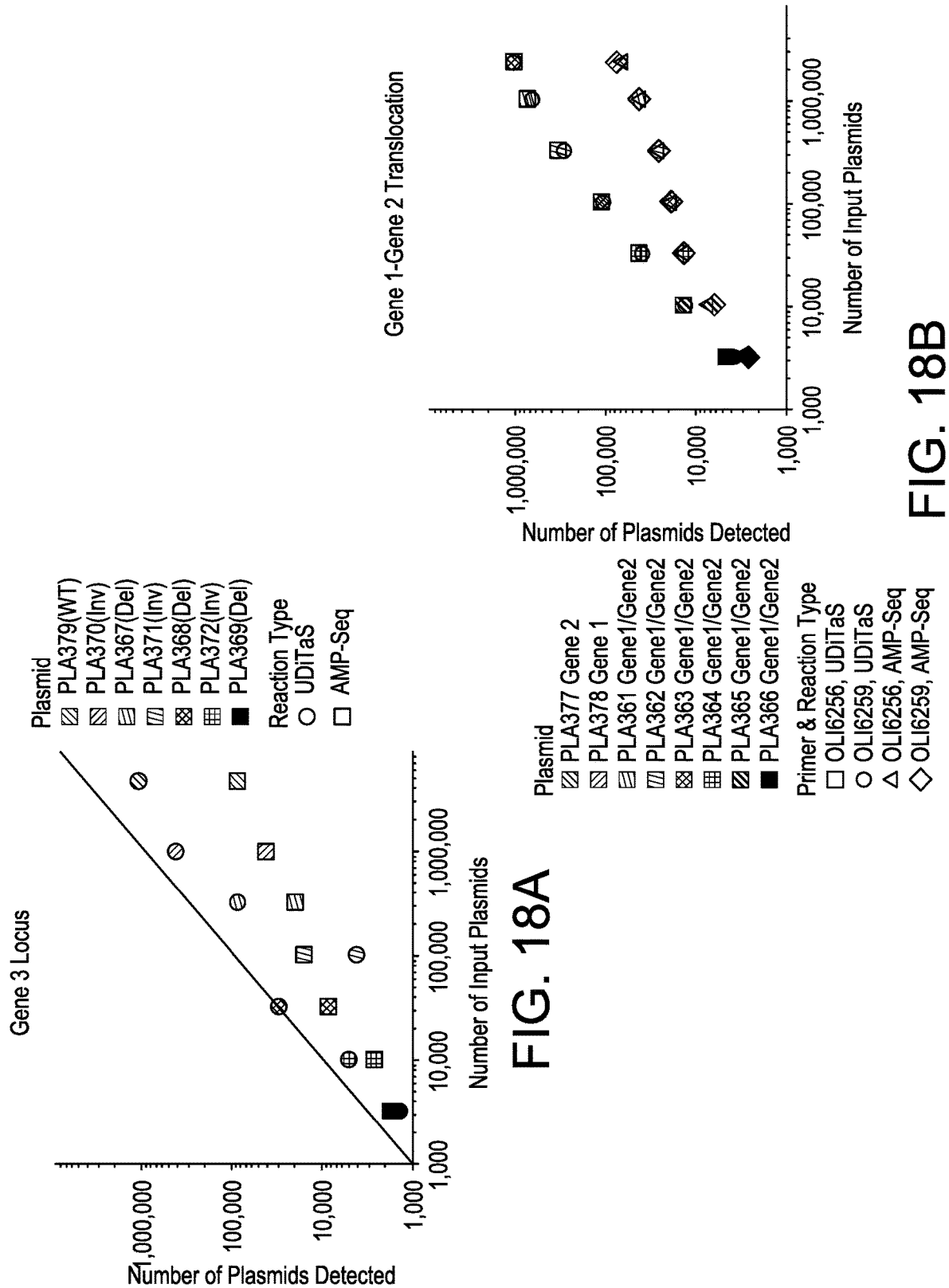
FIGS. 18A and 18B depict exemplary UDiTaS characterization and comparison to AMP-Seq using plasmid standards containing the Gene 3 structural variants (FIG. 18A) or the Gene 1/Gene 2 balanced translocation (FIG. 18B).

Plasmids containing either the Gene 1/Gene 2 balanced translocation or Gene 3 structural variants were synthesized and contained engineered unique SNPs in the insert to identify the plasmid after sequencing. The plasmids ranging from ~2,200 to ~714,000 genome equivalents, were spiked into mouse genomic DNA and processed through the UDiTaS and AMP-Seq methods. The number of input plasmids versus the number of plasmids detected was plotted for both UDiTaS and AMP-Seq. UDiTaS showed excellent linearity down to the lowest dilution (FIGS. 18A and 18B). UDiTaS showed greater accuracy and linearity when compared to AMP-Seq (FIGS. 18A and 18B).

UDiTaS libraries were more linear and had higher dynamic range as compared to AMP-Seq given the same DNA input material. This was attributed to the more efficient tagmentation process, as compared to shearing and adapter ligation of AMP-Seq. Also UDiTas required fewer and more streamlined processing steps that increased the overall yield as compared to AMP-Seq.

To ensure that the carrier mouse genomic DNA was not influencing the UDiTaS reaction, additional sets of UDiTaS reactions were run with plasmids in the absence of any carrier DNA. FIG. 19A shows Gene 3 plasmids containing wild type, large deletion, or large insertion sequence (PLA379, PLA367, and PLA370). FIG. 19B shows Gene 1/Gene 2 plasmids containing balanced translocations (PLA377, PLA378, PLA365, and PLA366). Plasmids were diluted and plasmids mixtures were processed through UDiTaS and the analysis pipeline. The expected frequency for a given structural variant vs. measured frequency for a structural variant was plotted (when x=y is shown by the plotted line). Accuracy and linearity were excellent for both loci with all four primers, with an LLOD of ~0.01%-0.1% further demonstrating the robustness of the process.

Inter-Chromosomal Translocations Rates

Figure 14C:
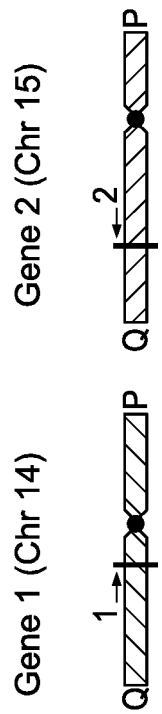
FIG. 14C depicts exemplary inter-chromosomal translocations in T-cells measured after nucleofection with two SpCas9 RNPs, one targeting Gene 1 and another Gene 2. The schematic and table shows all possible outcomes and the measured result when applicable. Vertical lines indicate editing sites and arrows indicate primers (1=OLI6259 and 2=OLI6256).

UDiTaS also measured inter-chromosomal translocation rates. To demonstrate this, two S. pyogenes Cas9 (SpCas9) ribonucleoprotein (RNP) complexes with sgRNAs targeting Gene1 and Gene2 genes were nucleofected into activated human CD4+ T-cells. UDiTaS libraries from these cells were prepared using primers that flanked each guide site. Of 10 possible end joining outcomes, it was possible to measure 7 using two targeting primers. All 7 outcomes were detected and quantified. These included NHEJ (non-homologous end joining) editing at the cut sites as well as balanced, acentric, and dicentric fusions between homologous or sister chromosomes as well as between distinct unrelated chromosomes (FIG. 14C). Although several studies have been published characterizing translocations in the context of gene editing, none have measured all events (Hu et al., Nat. Protoc. 2016; 11:853-71; Jiang et al., Sci. Rep. 2016; 6:21918; Ghezraoui et al. Mol. Cell. 2014; 55:829-42; Frock et al., Nat. Biotechnol. 2015; 33:179-186). Instead, these studies relied on translocation assays that necessitated piecing of translocations together and were not able to contextualize smaller indels rates. This example demonstrated quantification of double gene editing translocation rates with indels. This example also demonstrated inter-chromosomal translocation rates of ~2.5% with on-target indel editing of ~82% and ~91% (FIG. 14C) respectively for each guide RNA. Linearity and an LLoD of ~0.01% of the assay at Gene 1 and Gene 2 translocation loci were characterized with plasmids in a similar fashion as for the Gene 3 locus (FIG. 18A and FIG. 19B), to demonstrate the high sensitivity of UDiTaS to detect translocation events.

This example demonstrated that UDiTaS is a sequencing and analysis methodology that enabled simultaneous measurement of small indels and larger structural rearrangements, such as large deletions, inversions, and translocations. The UDiTaS method was robust, scalable and amenable to multiplexing of anchor primers when using low (50 ng) input DNA. This enabled monitoring of panels of candidate off-target editing sites when a sample was limited. In addition, the custom transposon described here, has potential to improve methods that utilize DNA shearing along with an anchor primer, such as GUIDE-Seq. The UDiTas method was also accurate and linear. UDiTaS is an important sequencing methodology enabling accurate quantification of intended, or unintended large structural changes, important for assessment of the efficacy of gene-editing technologies.

Methods of the Example

U-2 OS Bulk Editing Transfection Experiment

U-2 OS cells (ATCC) were maintained in DMEM, high glucose with Glutamax and sodium pyruvate (ThermoFisher), 10% Fetal Bovine Serum, and supplemented with 1% penicillin/streptomycin. Cells were transfected by Lonza nucleofection using the 4D nucleofector system. Briefly, 250,000 cells were transfected with 1.5 ug plasmid pAF003 expressing SaCas9 driven by a CMV promoter and 500 ng of linear DNA fragment expressing gRNAs driven by U6 promoter (250 ng each guide). Cells were nucleofected using the SE kit and pulse code DN-100 and plated in 6-well plates. Cells were cultured for 3 days post-nucleofection and 3 transfection technical replicates were pooled together. Genomic DNA was isolated using the Agencourt DNAdvance kit (Beckman Coulter) according to manufacturer's instructions.

HEK293 Cell Line Creation at the Gene 3 Locus

HEK293 cells (ATCC) were maintained in DMEM, high glucose with Glutamax and sodium pyruvate (ThermoFisher), 10% Fetal Bovine Serum and supplemented with 1% penicillin/streptomycin. Cells were transfected using the Mirus TransIT 293 kit, according to manufacturer's instructions. Briefly, 120,000 cells were seeded in a well of a 24-well plate 24 hours pre-transfection. Cells were transfected with 750 ng plasmid pAF003 expressing SaCas9 driven by a CMV promoter and 250 ng of linear DNA fragment expressing gRNAs driven by a U6 promoter (125 ng each guide). Following expansion, cells were trypsinized, diluted and re-plated in 96-well plates at a dilution of approximately 1 cell per every 3 wells. Cells were visually monitored to ensure single cell colonies and expanded into 24-well plates. To determine editing, genomic DNA was isolated from clones using the Agencourt DNAdvance kit (Beckman Coulter) according to manufacturer's instructions. Clones were screened by ddPCR and verified by Sanger sequencing.

T Cell—Gene 1/Gene 2

S. pyogenes guide RNAs targeting the Gene 1 and Gene 2 loci were generated by in vitro transcription of a PCR product using the T7-Scribe™ Standard RNA IVT Kit (CELLSCRIPT) following the manufacturer's protocol. The PCR product for the in vitro transcription reaction was generated using plasmid PLA380 as a template and the indicated forward primers (OLI7076 for Gene 2, and OLI7077 for Gene 1) with a common reverse primer (OLI7078).

The in vitro transcribed guide RNAs were complexed to wild type Cas9 protein at a molar ratio of 2:1 to generate ribonucleoprotein (RNP). The complexation integrity was evaluated by differential scanning fluorimetry (DSF). In brief, 5 μL of complexed RNP was diluted in 5 μL 2× Dye Mix. The 2× Dye Mix was generated from the 5000× stock SYPRO Orange Protein Gel Stain dye (Life Technologies, S6651) in 10×HEPES-Saline solution with $MgCl_2$ (Boston Bio Products, C-6767) diluted to 1× in nuclease-free water. The complexed samples and uncomplexed protein controls were placed in a 384-well plate and placed in a BioRad thermocycler using the following protocol: 1 minute at 20° C., Melt Curve from 20° C. to 95° C. with increment changes of 1° C., 1 minute at 4° C. Successful complexation is defined as a clear temperature shift between uncomplexed control samples and complexed RNP.

Human T cells were isolated from buffy coats using Miltenyi CD4 microbeads following the manufacturer's protocol. On day 0, T-cells were activated using Dynabeads® Human T-Activator CD3/CD28 for T Cell Expansion and Activation (ThermoFisher Scientific). Beads were removed on day 2. On day 4, cells were counted using Trypan Blue (ThermoFisher Scientific) and TC20™ Automated Cell Counter (Bio-Rad) according to manufacturer's protocol. For each condition 500,000 T cells were resuspended in 22 μL of Primary Cell Nucleofector Solution P2 (Lonza) containing 2 μM of total RNP. Samples were transferred to 16-well Nucleocuvette™ Strips (Lonza) and electroporated using program DS130 of the 4D-Nucleofector™ System (Lonza). Cells were subsequently transferred to untreated 96-well round bottom plates and cultured in 200 μL of X-Vivo 15 media (Lonza) containing 5% Human AB Serum (Gemini BioProduct), 1.6 mg/mL N-acetylcysteine (Sigma), 2 mM L-alanyl-L-glutamine (Thermo Scientific), 50 IU/mL IL-2 (Peprotech), 5 ng/mL IL-7 (Peprotech) and 0.5 ng/mL IL-15 (Peprotech).

Four days post nucleofection, samples were pelleted and genomic DNA purified using the Agencourt DNAdvance kit (Beckman Coulter) according to the manufacturer's protocol. UDiTaS was performed with the following modification. After tagmentation, the enzyme was inactivated with the addition of 1 μL of 0.2% SDS, pipette mixing and 5 min room temperature incubation. The tagmented DNA was added directly into round 1 PCR using primers OLI6259 and OLI6256 (FIG. 14C).

Plasmid Sensitivity Experiments

For Gene 3 plasmid-based sensitivity experiments PLA370, PLA367, and PLA379 were used (FIG. 19A). For the Gene 1/Gene 2 translocation plasmid-based sensitivity experiments PLA365, PLA366, PLA377, and PLA378 were used (FIG. 19B). Plasmid concentrations were determined using a NanoDrop2000 Spectrophotometer and working dilutions of 10 ng/μl were generated for all plasmids. In brief, for Gene 2 sensitivity experiments the first sample consists of a 50% mix of PLA370 (Inversion) and PLA367 (Large Deletion) and contains no control plasmid (PLA379). Subsequently, 10 dilutions were generated by serially diluting the PLA370/PLA367 mix (sqrt10 dilution factor) into control plasmids (PLA379) maintaining a total plasmid concentration of 10 ng/μL throughout the different dilutions. The last sample consisted of only control plasmids (PLA379). For Gene 1/Gene 2 sensitivity experiments the first sample consists of a 50% mix of PLA365 and PLA366 and contains no control plasmids (PLA377/PLA378). Subsequently, 10 dilutions were generated by serially diluting PLA366 (sqrt10 dilution factor) into an equal mix of control plasmids PLA377/PLA378 maintaining a total plasmid concentration of 10 ng/μL throughout the different dilutions. The last sample consisted of only control plasmids (equal mix between PLA377/PLA378). All samples were subsequently subjected to UDiTaS: Gene 1/Gene 2 translocation samples were amplified with OLI6256 and OLI6259, while Gene 3 plasmids were amplified with OLI6062. The UDiTaS protocol was applied with the following modifications: 6 cycles for first and second round PCR.

For plasmids spiked into mouse DNA, different amounts of unique plasmids were mixed into mouse gDNA. For Gene 3 plasmid spike in experiments, plasmids with the estimated copy number shown in Table 3 were spiked into 10 ng/μL mouse gDNA.

TABLE 3

Plasmids and amount used in Gene 3 spike-in experiment.

| Plasmid Name | Expected Plasmid Copy Number (per 50 ng reaction) |
|---|---|
| PLA370 | 1,032,035 |
| PLA367 | 326,363 |
| PLA371 | 103,204 |
| PLA368 | 32,636 |
| PLA372 | 10,320 |
| PLA369 | 3,264 |
| PLA379 | 4,684,365 |

For Gene 1/Gene 2 plasmid spike in experiments, plasmids were spiked into 10 ng/μL mouse gDNA as described in Table 4.

TABLE 4

Plasmids and amount used in Gene 1/Gene 2 spike-in experiments.

| Plasmid Name | Expected Plasmid Copy Number (per 50 ng reaction) |
|---|---|
| PLA361 | 1,031,968 |
| PLA362 | |
| PLA363 | |
| PLA364 | |
| PLA365 | |
| PLA366 | |
| PLA377/PLA378 (equal mix) | |
| PLA361 | |

TABLE 4-continued

Plasmids and amount used in Gene 1/Gene 2 spike-in experiments.

| Plasmid Name | Expected Plasmid Copy Number (per 50 ng reaction) |
|---|---|
| PLA362 | 326,339 |
| PLA363 | 103,197 |
| PLA364 | 32,634 |
| PLA365 | 10,320 |
| PLA366 | 3,263 |
| PLA377/PLA378 (Equal mix) | 4,695,992 |

TABLE 5

Adapter oligo sequences used for annealing step and complexing with the Tn5: Oligos. The mosaic end sequence is underlined.

| Oligo Name | sequence 5'-3' |
|---|---|
| Tn5-A bottom | [Phos]CTGTCTCTTATACA[ddC] (SEQ ID NO: 32) |
| i5_N501_UMI_Tn5-A | AATGATACGGCGACCACCGAGATCTACACTAGATCGCNNNNNNNNNTCGTCGGCAGCGTC<u>AGATGTGTATAAGAGACAG</u> (SEQ ID NO: 33) |
| i5_N502_UMI_Tn5-A | AATGATACGGCGACCACCGAGATCTACACCTCTCTATNNNNNNNNNTCGTCGGCAGCGTC<u>AGATGTGTATAAGAGACAG</u> (SEQ ID NO: 34) |
| i5_N503_UMI_Tn5-A | AATGATACGGCGACCACCGAGATCTACACTATCCTCTNNNNNNNNNTCGTCGGCAGCGTC<u>AGATGTGTATAAGAGACAG</u> (SEQ ID NO: 35) |
| i5_N504_UMI_Tn5-A | AATGATACGGCGACCACCGAGATCTACACAGAGTAAGANNNNNNNNNTCGTCGGCAGCGTC<u>AGATGTGTATAAGAGACAG</u> (SEQ ID NO: 36) |
| i5_N505_UMI_Tn5-A | AATGATACGGCGACCACCGAGATCTACACGTAAGGAGNNNNNNNNNTCGTCGGCAGCGTC<u>AGATGTGTATAAGAGACAG</u> (SEQ ID NO: 37) |
| i5_N506_UMI_Tn5-A | AATGATACGGCGACCACCGAGATCTACACACTGCATANNNNNNNNNTCGTCGGCAGCGTC<u>AGATGTGTATAAGAGACAG</u> (SEQ ID NO: 38) |
| i5_N507_UMI_Tn5-A | AATGATACGGCGACCACCGAGATCTACACAAGGAGTANNNNNNNNNTCGTCGGCAGCGTC<u>AGATGTGTATAAGAGACAG</u> (SEQ ID NO: 39) |
| i5_N508_UMI_Tn5-A | AATGATACGGCGACCACCGAGATCTACACCTAAGCCTNNNNNNNNNTCGTCGGCAGCGTC<u>AGATGTGTATAAGAGACAG</u> (SEQ ID NO: 40) |

TABLE 6

| Oligo Name | i5 Barcode Sequence | i5 Barcode READ (Tx10 for UMI) |
|---|---|---|
| i5_N501_UMI_Tn5-A | TAGATCGC | TAGATCGCTTTTTTTTTT (SEQ ID NO: 41) |
| i5_N502_UMI_Tn5-A | CTCTCTAT | CTCTCTATTTTTTTTTTT (SEQ ID NO: 42) |
| i5_N503_UMI_Tn5-A | TATCCTCT | TATCCTCTTTTTTTTTTT (SEQ ID NO: 43) |
| i5_N504_UMI_Tn5-A | AGAGTAGA | AGAGTAGATTTTTTTTTT (SEQ ID NO: 44) |
| i5_N505_UMI_Tn5-A | GTAAGGAG | GTAAGGAGTTTTTTTTTT (SEQ ID NO: 45) |
| i5_N506_UMI_Tn5-A | ACTGCATA | ACTGCATATTTTTTTTTT (SEQ ID NO: 46) |
| i5_N507_UMI_Tn5-A | AAGGAGTA | AAGGAGTATTTTTTTTTT (SEQ ID NO: 47) |
| i5_N508_UMI_Tn5-A | CTAAGCCT | CTAAGCCTTTTTTTTTTT (SEQ ID NO: 48) |

TABLE 7

P5 /i5 oligo sequence for Round 1 and 2 PCR:

| Oligo Name | Sequence 5'-3' |
|---|---|
| i5 | AATGATACGGCGACCACCGAGATCTACAC (SEQ ID NO: 49) |

TABLE 8 i7 Barcoded oligo sequences for Round 2 PCR:

| Oligo Name | Sequence (5'-3') | i7 BC Seq | i7 BC READ |
|---|---|---|---|
| i7_N701_SBS12 | CAAGCAGAAGACGGCATAAGCGGAATCGAGATAGCGGAATGTGACTGGAGTTCAGACGTGT (SEQ ID NO: 50) | AGCGGAAT (SEQ ID NO: 62) | ATTCCGCT (SEQ ID NO: 74) |
| i7_N702_SBS12 | CAAGCAGAAGACGGCATAGATCATGCCGAGATGATCATGCGTGACTGGAGTTCAGACGTGT (SEQ ID NO: 51) | GATCATGC (SEQ ID NO: 63) | GCATGATG (SEQ ID NO: 75) |
| i7_N703_SBS12 | CAAGCAGAAGACGGCATAAAGACGGACGAGATAAGACGGAGTGACTGGAGTTCAGACGTGT (SEQ ID NO: 52) | AAGACGGA (SEQ ID NO: 64) | TCCGTCTT (SEQ ID NO: 76) |
| i7_N704_SBS12 | CAAGCAGAAGACGGCATACGAGTCCTCGAGATCGAGTCCTGTGACTGGAGTTCAGACGTGT (SEQ ID NO: 53) | CGAGTCCT (SEQ ID NO: 65) | AGGACTCG (SEQ ID NO: 77) |
| i7_N705_SBS12 | CAAGCAGAAGACGGCATATCCTCAGGCGAGATTCCTCAGGGTGACTGGAGTTCAGACGTGT (SEQ ID NO: 54) | TCCTCAGG (SEQ ID NO: 66) | CCTGAGGA (SEQ ID NO: 78) |
| i7_N706_SBS12 | CAAGCAGAAGACGGCATAGTACGGATCGAGATGTACGGATGTGACTGGAGTTC (SEQ ID NO: 55) | GTACGGAT (SEQ ID NO: 67) | ATCCGTAC (SEQ ID NO: 79) |
| i7_N707_SBS12 | CAAGCAGAAGACGGCATACATCTCTCGCAGATCATCTCTCGTGACTGGAGTTCAGACGTGT (SEQ ID NO: 56) | CATCTCTC (SEQ ID NO: 68) | GAGAGATG (SEQ ID NO: 80) |

TABLE 8-continued i7 Barcoded oligo sequences for Round 2 PCR:

| Oligo Name | Sequence (5'-3') | i7 BC Seq | i7 BC READ |
|---|---|---|---|
| i7_N710_SBS12 | CAAGCAGAAGACGGCATAGTCGGAGC CGAGATGTCGGAGCGTGA (SEQ ID CTGGAGTTCAGACGTGT NO: 69) (SEQ ID NO: 57) | GCTCCGAC (SEQ ID NO: 81) | |
| i7_N711_SBS12 | CAAGCAGAAGACGGCATAACGGAGAA CGAGATACGGAGAAGTGA (SEQ ID CTGGAGTTCAGACGTGT NO: 70) (SEQ ID NO: 58) | TTCTCCGT (SEQ ID NO: 82) | |
| i7_N712_SBS12 | CAAGCAGAAGACGGCATAAGGAGATG CGAGATAGGAGATGGTGA (SEQ ID CTGGAGTTCAGACGTGT NO: 71) (SEQ ID NO: 59) | CATCTCCT (SEQ ID NO: 83) | |
| i7_N714_SBS12 | CAAGCAGAAGACGGCATAAGTACTCG CGAGATAGTACTCGGTGA (SEQ ID CTGGAGTTCAGACGTGT NO: 72) (SEQ ID NO: 60) | CGAGTACT (SEQ ID NO: 84) | |
| i7_N715_SBS12 | CAAGCAGAAGACGGCATAGGACTCTA CGAGATGGACTCTAGTGA (SEQ ID CTGGAGTTCAGACGTGT NO: 73) (SEQ ID NO: 61) | TAGAGTCC (SEQ ID NO: 85) | |

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method for analyzing cleavage and/or repair events for a site specific nuclease, the method comprising:
   (a) contacting a cell or tissue with the site specific nuclease, wherein contacting the cell or tissue with the site specific nuclease results in cleavage and/or repair of genomic DNA in the cell or tissue;
   (b) obtaining a genomic DNA sample from the cell or tissue that has been contacted with the site specific nuclease;
   (c) contacting the genomic DNA sample with a transposase and a transposon comprising a first detection sequence at the 5' end of the transposon, under conditions whereby the transposon is inserted into the genomic DNA sample and the genomic DNA sample is fragmented into a plurality of tagmented double-stranded nucleic acid fragments comprising the transposon attached to the 5' end of the nucleic acid fragments;
   (d) amplifying the tagmented nucleic acid fragments using
      (i) a first fixed primer comprising a nucleotide sequence complementary to a predetermined location in the genomic DNA and comprising a second detection sequence at its 5' end, and
      (ii) a second selective primer comprising a nucleotide sequence complementary to at least a portion of the first detection sequence,
   to form amplified nucleic acid fragments comprising the first detection sequence, the transposon attached to the 5' end of the nucleic acid fragments, and the second detection sequence;
   (e) sequencing the amplified nucleic acid fragments to generate sequencing data; and
   (f) analyzing the sequencing data for the cleavage and/or repair events of the site specific nuclease.

2. The method of claim 1, wherein the first detection sequence comprises a first sequencing tag.

3. The method of claim 2, wherein step (e) comprises contacting the amplified nucleic acid fragments with a first sequencing primer that hybridizes to the first sequencing tag.

4. The method of claim 1, wherein the second detection sequence comprises a second sequencing tag.

5. The method of claim 4, wherein step (e) comprises contacting the amplified nucleic acid fragments with a second sequencing primer that hybridizes to the second sequencing tag.

6. The method of claim 1, wherein the genomic DNA sample is obtained from a single cell.

7. The method of claim 1, wherein step (d) comprises using a plurality of first fixed primers, wherein each comprises a nucleotide sequence complementary to a different predetermined location in the genomic DNA.

8. The method of claim 7, wherein step (d) comprises performing a plurality of amplification reactions, each reaction using a different first fixed primer.

9. The method of claim 7, wherein each of the plurality of first fixed primers comprises a detection sequence comprising (i) the same sequencing tag and (ii) a unique barcode.

10. The method of claim 1, wherein the double-stranded nucleic acid fragments comprise about 500 to about 5000 bps.

11. The method of claim 1, wherein the site-specific nuclease is Cas9.

* * * * *